US010160745B2

(12) United States Patent
Bousba et al.

(10) Patent No.: US 10,160,745 B2
(45) Date of Patent: *Dec. 25, 2018

(54) PIPERIDINE AND AZEPINE DERIVATIVES AS PROKINETICIN RECEPTOR MODULATORS

(71) Applicant: TAKEDA PHARMACEUTICAL COMPANY LIMITED, Osaka (JP)

(72) Inventors: Sarah Bousba, Cambridge (GB); Anne Goldby, Cambridge (GB); Kerry Jenkins, Cambridge (GB); Natasha Kinsella, Kampala (UG); Martin Teall, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/702,100

(22) Filed: Sep. 12, 2017

(65) Prior Publication Data
US 2018/0009780 A1   Jan. 11, 2018

Related U.S. Application Data

(63) Continuation of application No. 14/910,377, filed as application No. PCT/GB2014/052428 on Aug. 7, 2014, now Pat. No. 9,790,201.

(30) Foreign Application Priority Data

Aug. 8, 2013 (GB) .................. 1314286.4

(51) Int. Cl.
| *A61K 31/454* | (2006.01) |
| *A61K 31/4545* | (2006.01) |
| *C07D 401/06* | (2006.01) |
| *C07D 403/06* | (2006.01) |
| *A61K 31/501* | (2006.01) |
| *A61K 31/55* | (2006.01) |
| *C07D 401/14* | (2006.01) |

(52) U.S. Cl.
CPC .......... *C07D 401/06* (2013.01); *A61K 31/454* (2013.01); *A61K 31/4545* (2013.01); *A61K 31/501* (2013.01); *A61K 31/55* (2013.01); *C07D 401/14* (2013.01); *C07D 403/06* (2013.01)

(58) Field of Classification Search
CPC . A61K 31/454; A61K 31/4545; C07D 401/06
See application file for complete search history.

(56) References Cited

U.S. PATENT DOCUMENTS

| 9,359,330 | B2 | 5/2016 | Pinto |
| 2009/0197859 | A1 | 8/2009 | Collantes et al. |
| 2016/0145263 | A1 | 6/2016 | Tafesse |

FOREIGN PATENT DOCUMENTS

| CN | 101495464 A | 7/2009 |
| WO | WO 96/06098 A1 | 2/1996 |
| WO | WO 97/23466 A1 | 7/1997 |
| WO | WO 97/30998 A1 | 8/1997 |
| WO | WO 99/03859 A1 | 1/1999 |
| WO | WO 99/05134 A1 | 2/1999 |
| WO | WO 00/42044 A1 | 7/2000 |
| WO | WO 01/29034 A1 | 4/2001 |
| WO | WO 01/36417 A1 | 5/2001 |
| WO | WO 01/60821 A1 | 8/2001 |
| WO | WO 02/08212 A1 | 1/2002 |
| WO | WO 02/094794 A1 | 11/2002 |
| WO | WO 02/096912 A1 | 12/2002 |
| WO | WO 03/087102 A1 | 10/2003 |
| WO | WO 03/087103 A1 | 10/2003 |
| WO | WO 03/087104 A1 | 10/2003 |
| WO | WO 2004/016616 A1 | 2/2004 |
| WO | WO 2004/016617 A1 | 2/2004 |
| WO | WO 2004/019947 A1 | 3/2004 |
| WO | WO 2004/048334 A1 | 6/2004 |
| WO | WO 2005/115389 A2 | 12/2005 |
| WO | WO 2007/079163 A2 | 7/2007 |
| WO | WO 2007/079163 A3 | 7/2007 |
| WO | WO 2007/079214 A2 | 7/2007 |
| WO | WO 2010/077976 A2 | 7/2010 |
| WO | WO 2010/077976 A3 | 7/2010 |
| WO | 2012006004 A1 | 1/2012 |

(Continued)

OTHER PUBLICATIONS

JK Search Report issued on priority document, Application No. GB1314286 A, dated Feb. 10, 2014, 2 pages.
Chemical Abstracts Registry No. 958579-44-7.
Chemical Abstracts Registry No. 958573-72-3.
Chemical Abstracts Registry No. 1060531-60-3.
Chemical Abstracts Registry No. 1060938-40-0.
Chemical Abstracts Registry No. 1066932-65-7.
Chemical Abstracts Registry No. 1069480-79-0.
Chemical Abstracts Registry No. 1069844-92-3.
Chemical Abstracts Registry No. 1185568-86-8.
Chemical Abstracts Registry No. 1185671-22-0.
Chemical Abstracts Registry No. 1332132-31-6.
Chemical Abstracts Registry No. 1377991-39-3.
Chemical Abstracts Registry No. 1394350-35-6.
Chemical Abstracts Registry No. 1394353-59-3.

(Continued)

*Primary Examiner* — Brenda L Coleman
(74) *Attorney, Agent, or Firm* — Barnes & Thornburg LLP; Scott Rothenberger

(57) ABSTRACT

The present invention provides compounds of formula (I) and pharmaceutically acceptable salts thereof (Formula (I)) in which m, X, $R^1$, $R^2$, $R^3$ and $R^5$ are as defined in the specification, processes for their preparation, pharmaceutical compositions N containing them and their use in therapy.

(I)

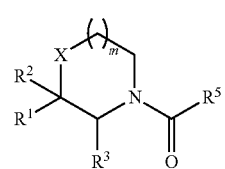

32 Claims, No Drawings

(56) References Cited

FOREIGN PATENT DOCUMENTS

WO    WO 2014/160668 A1    10/2014

OTHER PUBLICATIONS

Chemical Abstracts Registry No. 1394382-76-3.
Chemical Abstracts Registry No. 1394445-54-5.
Chemical Abstracts Registry No. 1394501-80-4.
Chemical Abstracts Registry No. 1394546-79-2.
Chemical Abstracts Registry No. 1394514-90-9.
Chemical Abstracts Registry No. 1394590-89-6.
Chemical Abstracts Registry No. 1394606-88-2.
Chemical Abstracts Registry No. 1394611-35-8.
Chemical Abstracts Registry No. 1394612-65-7.
Chemical Abstracts Registry No. 1413415-35-6.
Chemical Abstracts Registry No. 1413422-99-7.
Chemical Abstracts Registry No. 1413524-91-0.
Chemical Abstracts Registry No. 1413132-09-8.
Chemical Abstracts Registry No. 1422898-16-5.
Chemical Abstracts Registry No. 1434933-29-5.
International Search Report and Written Opinion from related International Application PCT/GB2014/052428, dated Oct. 2, 2014, 7 pages.
Miyaura, et al., "A new stereospecific cross-coupling by the palladium-catalyzed reaction of 1-alkenylboranes with 1-alkenyl or 1-alkynyl halides". Tetrahedron Letters 20 (36), 1979, pp. 3437-3440.
Miyaura, et al., "Stereoselective synthesis of arylated (E)-alkenes by the reaction of alk-1-enylboranes with aryl halides in the presence of palladium catalyst". Chem. Comm., No. 19, 1979, pp. 866-867.
Miyaura, et al., "Palladium-Catalyzed Cross-Coupling Reactions of Organoboron Compounds". Chemical Reviews, 95 (7), 1995, pp. 2457-2483.
Olofson, "A New Reagent for the Selective, High-Yield N-Dealkylation of Tertiary Amines: Improved Syntheses of Naltrexone and Nalbuphine". *J. Org. Chem.* 49, 1984, pp. 2081-2082.
Search Report for Great Brittain Application No. GB1314286.4, dated Feb. 10, 2014.

PIPERIDINE AND AZEPINE DERIVATIVES AS PROKINETICIN RECEPTOR MODULATORS

CROSS-REFERENCE TO RELATED APPLICATIONS

This application is a continuation of U.S. patent application Ser. No. 14/910,377, filed Feb. 5, 2016, which is a Section 371 National Stage Application of International No. PCT/GB2014/052428, filed Aug. 7, 2014, and published as WO/2015/019103 A1 on Feb. 12, 2015, which claims priority from GB Patent Application No. 1314286.4, filed Aug. 8, 2013, the contents of which are incorporated herein in their entirety for all purposes.

The present invention relates to the use of piperidine and azepine derivatives in therapy, particularly for the treatment or prevention of psychiatric and neurological conditions.

Prokineticins are cysteine-rich regulatory peptides that are thought to exert signaling activity via two highly conserved G protein-coupled receptors (GPCR), the prokineticin receptor 1 (PKR1 or PROKR1) and the prokineticin receptor 2 (PKR2 or PROKR2), that belong to the 7-transmembrane domain, G protein-coupled receptor (GPCR) superfamily.

Prokineticin receptor 1 (also known as GPR73) shows 87% homology to Prokineticin Receptor 2 (also known as GPR73L1). Prokineticins (PK1 and PK2) contain 86 and 81 amino acids respectively, sharing 45% amino acid identity. Both prokineticins activate the two prokineticin receptors, PKR1 and PKR2, with similar potency.

PKR1 receptors couple to $G_q/G_{11}$ proteins leading to phospholipase C activation, inositol phosphate production and calcium mobilization. In addition, activation of the mitogen-activated protein kinase (MAPK) pathways has also been described.

PKR1 is broadly distributed throughout peripheral tissues including the intestinal tract, testis, uterus, lung, mouse dorsal root ganglia, macrophage, bone, heart, rectum, white adipose and peripheral blood leukocytes. In addition, the receptor is expressed in the brain particularly in olfactory regions as well as in dorsal root ganglion (DRG) neurons, mouse hippocampus, dentate gyrus, cerebellar cortex, cerebral cortex, human hippocampus, amygdala, medulla oblongata and spinal cord.

Prokineticins were originally identified as potent agents mediating gut motility, but were later shown to promote angiogenesis in steroidogenic glands (e.g. adrenal gland), heart and reproductive systems. They also modulate neurogenesis, circadian rhythms, nociception, haematopoiesis as well as the immune response. Prokineticins are thought to be associated with pathologies of the reproductive and nervous systems, myocardial infarction and tumorigenesis.

Consequently, antagonisim of the functions of the prokineticins may have utility in the treatment of, for example, gastrointestinal disorders or diseases including gastrointestinal motility; angiogenesis; hematopoiesis; diabetes (e.g. as described in International Patent Application Publication No. WO 2010/077976) and pain (e.g. as described in International Patent Application Publication No. WO 2007/079214).

Certain piperidine derivatives are known chemical library compounds with no known use that are available from commercial suppliers such as Chembridge Corporation, in particular the following compounds having Chemical Abstracts Registry Nos. 1413415-35-6, 1332132-31-6, 1377991-39-3, 1394611-35-8, 1422898-16-5, 1413524-91-0, 1413422-99-7, 1413132-09-8, 1394546-79-2, 1394514-90-9, 1394445-54-5, 1394350-35-6, 1185671-22-0, 1185568-86-8, 1060938-40-0, 958579-44-7 and 958573-72-3.

In addition, WO 2004/048334 and WO 2005/115389 describe certain phenyl substituted piperidine compounds for use as peroxisome proliferator activator receptor (PPAR) agonists and US 2009/0197859 describes certain piperidine and azepine derivatives as 5-HT ligands.

We have now discovered a new class of compounds that are prokineticin receptor modulators which have desirable activity profiles. The compounds of this invention have beneficial potency, selectivity and/or pharmacokinetic properties.

In accordance with the present invention, there is therefore provided a compound of formula

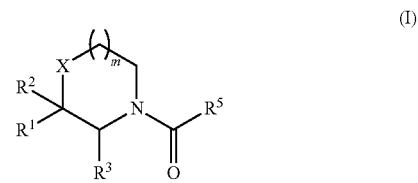

(I)

wherein $R^1$ represents a $C_5$-$C_{10}$ aryl group which is optionally substituted by at least one substituent selected from halogen, hydroxyl, cyano, oxo (=O), $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy. $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, —$NR^6R^7$, —$CONR^8R^9$, $C_3$-$C_6$ cycloalkyl, $C_3$-$C_6$ cycloalkyloxy or $C_3$-$C_6$ cycloalkylmethyl;

$R^2$ represents a hydrogen or fluorine atom or a hydroxyl or $C_1$-$C_3$ alkoxy group and $R^3$ represents a hydrogen atom, or $R^2$ and $R^3$ may together form a carbon-carbon bond;

X represents a group $CHR^4$;

$R^4$ to represents a hydrogen atom or, when $R^3$ represents a hydrogen atom. $R^4$ may together with $R^2$ form a carbon-carbon bond;

m is 1 or 2;

$R^5$ represents a 5- to 6-membered heteroaryl group having one or more ring nitrogen atoms as the only ring heteroatoms, the heteroaryl group being optionally substituted by at least one substituent selected from halogen, cyano, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, —$NR^{10}R^{11}$, —$CONR^{12}R^{13}$, $C_3$-$C_6$ cycloalkyl, $C_3$-$C_6$ cycloalkyloxy or $C_3$-$C_6$ cycloalkylmethyl;

$R^6$ and $R^7$ each independently represent a hydrogen atom or a $C_1$-$C_6$ alkyl or $C_3$-$C_6$ cycloalkyl group, or $R^6$ and $R^7$ may together with the nitrogen atom to which they are attached form a 4- to 7-membered saturated heterocyclic ring optionally substituted by halogen or hydroxy;

$R^8$ and $R^9$ each independently represent a hydrogen atom or a $C_1$-$C_6$ alkyl group, or $R^8$ and $R^9$ may together with the nitrogen atom to which they are attached form a 4- to 7-membered saturated heterocyclic ring;

$R^{10}$ and $R^{11}$ each independently represent a hydrogen atom or a $C_1$-$C_6$ alkyl or $C_3$-$C_6$ cycloalkyl group, or $R^{10}$ and $R^{11}$ may together with the nitrogen atom to which they are attached form a 4- to 7-membered saturated heterocyclic ring optionally substituted by halogen or hydroxy; and $R^{12}$ and $R^{13}$ each independently represent a hydrogen atom or a $C_1$-$C_6$ alkyl group, or $R^{12}$ and $R^{13}$ may together with the nitrogen atom to which they are attached form a 4- to 7-membered saturated heterocyclic ring;

provided that the compound of formula (I) is not:
(3-(4-chlorophenyl)-1-piperidinyl)(1-methyl-3-propyl-1H-pyrazol-5-yl)methanone,
(2-(ethylamino)-5-pyrimidinyl)(3-phenyl-1-piperidinyl)methanone,
(6-amino-3-pyridinyl)(3-(2-methylphenyl)-1-piperidinyl)methanone,
(2-amino-4-pyridinyl)(3-(2-methylphenyl)-1-piperidinyl)methanone,
[1-ethyl-3-(1-methyethyl)-1H-pyrazol-5-yl][3-(2-methylphenyl)-1-piperidinyl]methanone,
[4-methyl-2-(1-methyethyl)-5-pyrimidinyl][3-(2-methylphenyl)-1-piperidinyl]methanone,
[3-(2-methylphenyl)-1-piperidinyl][2-(4-morpholinyl)-5-pyrimidinyl]methanone,
[3-(3-methylphenyl)-1-piperidinyl](1-methyl-3-propyl-1H-pyrazol-5-yl)methanone,
[3-(3-methylphenyl)-1-piperidinyl]-2-pyridinyl-methanone,
5-[[3-(2-methylphenyl)-1-piperidinyl]carbonyl]-2-pyridinecarbonitrile,
(2-methoxy-3-pyridinyl)[3-(3-methylphenyl)-1-piperidinyl]methanone,
[3-(2-methylphenyl)-1-piperidinyl](3-propyl-1H-pyrazol-4-yl)methanone,
(1-ethyl-1H-pyrazol-4-yl)[3-(3-methylphenyl)-1-piperidinyl]methanone,
[1-(1-methylethyl)-1H-pyrazol-4-yl](3-phenyl-1-piperidinyl)methanone,
(5-methyl-1H-imidazol-2-yl)[3-(2-methylphenyl)-1-piperidinyl]methanone,
[2-(1,1-dimethylethyl)-5-pyrimidinyl][3-hydroxy-3-(2-methoxyphenyl)-1-piperidinyl]methanone, or
[3-hydroxy-3-(2-methoxyphenyl)-1-piperidinyl][1-(1-methylethyl)-1H-pyrazol-5-yl]methanone;

or a pharmaceutically acceptable salt thereof.

In the context of the present specification, unless otherwise stated, an alkyl, alkenyl or alkynyl substituent group or an alkyl, alkenyl or alkynyl moiety in a substituent group may be linear or branched. Examples of $C_1$-$C_6$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl neopentyl and n-hexyl. Examples of $C_2$-$C_6$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl. Examples of $C_2$-$C_6$ alkynyl groups/moieties include ethynyl, propynyl, 1-butynyl, 2-butynyl, 1-pentynyl and 1-hexynyl.

A $C_1$-$C_6$ haloalkyl or $C_1$-$C_6$ haloalkoxy substituent group/moiety will comprise at least one halogen atom, e.g. one, two, three, four or five halogen atoms, examples of which include trifluoromethyl, trifluoromethoxy or pentafluoroethyl.

A $C_1$-$C_6$ hydroxyalkyl substituent group/moiety will comprise at least one hydroxyl group. e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

A $C_5$-$C_{10}$ aryl group refers to a group derived from an aromatic hydrocarbon containing from five to ten carbon atoms. The aryl group may be monocyclic or polycyclic (e.g. bicyclic) in which the two or more rings are fused, examples of which include phenyl, 1-naphthyl and 2-naphthyl. Also included within the scope of the term "aryl", as it is used herein, is a group in which an aromatic ring is fused to one or more non-aromatic rings as exemplified by indanyl and tetrahydronaphthyl, where the point of attachment to the nitrogen-containing ring in formula (I) is on the aromatic ring.

A $C_3$-$C_6$ cycloalkyl group or moiety in a substituent group represents a saturated monocyclic hydrocarbon ring structure containing from three to six carbon atoms.

A 4- to 7-membered saturated heterocyclic ring will contain at least one ring nitrogen atom and may contain one or more (e.g. one or two) further ring heteroatoms independently selected from nitrogen, oxygen and sulphur atoms. It will be understood that the definition is not intended to include unstable structures or any O—O, O—S or S—S bonds and that a substituent, if present, may be attached to any suitable ring atom. Examples of heterocyclic rings include azetidinyl, pyrrolidinyl, piperidinyl, morpholinyl, piperazinyl, 1,4-azathianyl, azepanyl and 1,4-oxaazepanyl.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

$R^1$ represents a $C_5$-$C_{10}$, e.g. $C_6$-$C_{10}$, aryl group which is optionally substituted by at least one substituent (e.g. one, two, three or four substituents) independently selected from halogen (e.g. fluorine, chlorine or bromine), hydroxyl, cyano, oxo (=O), $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl, $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylthio, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy. $C_1$-$C_6$, or $C_1$-$C_4$, or $C_1$-$C_2$ alkoxycarbonyl, —$NR^6R^7$, —$CONR^8R^9$, $C_3$-$C_6$ cycloalkyl, $C_3$-$C_6$ cycloalkyloxy or $C_3$-$C_6$ cycloalkylmethyl.

In an embodiment of the invention. $R^1$ represents a $C_5$-, $C_6$- or $C_7$- to $C_8$-, $C_9$- or $C_{10}$-aryl, advantageously $C_6$-aryl, group which is optionally substituted by at least one substituent (e.g. one, two, three or four substituents) independently selected from halogen (e.g. fluorine, chlorine or bromine), hydroxyl, cyano, oxo (=O), $C_1$-$C_2$ alkyl, $C_2$-$C_4$ alkenyl, $C_2$-$C_4$ alkynyl, $C_1$-$C_2$ haloalkyl, $C_1$-$C_2$ hydroxyalkyl, $C_1$-$C_2$ alkoxy, $C_1$-$C_2$ haloalkoxy, $C_1$-$C_2$ alkylthio, $C_1$-$C_2$ alkylsulphinyl, $C_1$-$C_2$ alkylsulphonyl, $C_1$-$C_2$ alkylcarbonyl, $C_1$-$C_2$ alkylcarbonyloxy, $C_1$-$C_2$ alkoxycarbonyl, —$NR^6R^7$, —$CONR^8R^9$, $C_3$-$C_6$ or $C_3$-$C_5$ or $C_5$-$C_6$ cycloalkyl. $C_3$-$C_6$ or $C_3$-$C_5$ or $C_5$-$C_6$ cycloalkyloxy or $C_3$-$C_6$ or $C_3$-$C_5$ or $C_5$-$C_6$ cycloalkylmethyl.

In another embodiment of the invention, $R^1$ represents a $C_5$-, $C_6$- or $C_7$- to $C_8$-, $C_9$- or $C_{10}$-aryl, advantageously phenyl, group which is optionally substituted by at least one substituent, advantageously one, two or three substituents, independently selected from halogen (particularly fluorine or chlorine), cyano, $C_1$-$C_2$ alkyl, $C_1$-$C_2$ haloalkyl (e.g. trifluoromethyl), $C_1$-$C_2$ alkoxy and $C_1$-$C_2$ haloalkoxy (e.g. difluoromethoxy or trifluoromethoxy).

If $R^1$ represents an optionally substituted phenyl group, the optionally substituent(s) is/are preferably attached at the ortho and/or para positions of the phenyl group, as shown by the asterisks in the following structural formula:

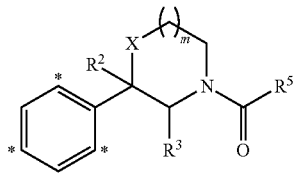

In a preferred embodiment, $R^1$ represents any one of the following moieties or is selected from a group containing two or more of such moieties in any combination:
(i) phenyl,
(ii) 2-fluorophenyl,
(iii) 4-fluorophenyl,
(iv) 2-chlorophenyl,
(v) 4-chlorophenyl,
(vi) 2,4-dichlorophenyl,
(vii) 2-methylphenyl,
(viii) 3-methylphenyl,
(ix) 4-methylphenyl,
(x) 2-trifluoromethylphenyl,
(xi) 4-trifluoromethylphenyl,
(xii) 2-methyl-4-chlorophenyl,
(xiii) 2-trifluoromethyl-4-chlorophenyl,
(xiv) 2-fluoro-4-chlorophenyl,
(xv) 2-chloro-4-fluorophenyl,
(xvi) 2-methoxyphenyl,
(xvii) 3-methoxyphenyl,
(xviii) 4-methoxyphenyl,
(xix) 2-trifluoromethoxyphenyl,
(xx) 2-ethoxy-4-chlorophenyl,
(xxi) 2-trifluoromethyl-4-methoxyphenyl,
(xxii) 2-methyl-4-methoxyphenyl,
(xxiii) 2-difluoromethoxyphenyl,
(xxiv) 2-cyanophenyl,
(xxv) 4-chloro-2,6-dimethylphenyl, and
(xxvi) 2-methoxy-4-(trifluoromethyl)phenyl.

In one embodiment of the invention, $R^2$ represents a hydrogen atom and $R^3$ represents a hydrogen atom.

In another embodiment, $R^2$ represents a fluorine atom and $R^3$ represents a hydrogen atom.

In yet another embodiment, $R^2$ represents a hydroxyl group and $R^3$ represents a hydrogen atom.

In a further embodiment, $R^2$ represents a $C_1$-$C_3$ alkoxy (particularly methoxy) group and $R^3$ represents a hydrogen atom.

Alternatively, $R^2$ and $R^3$ may together form a carbon-carbon bond such that the nitrogen-containing ring in formula (I) contains a carbon-carbon double bond as illustrated below:

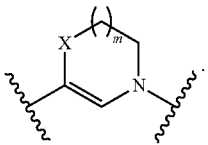

Preferred compounds of formula (I) are those in which $R^2$ and $R^3$ both represent a hydrogen atom.

In a preferred embodiment, $R^4$ represents a hydrogen atom.

In a preferred embodiment of the invention, m is 1.

$R^5$ represents a 5- to 6-membered heteroaryl group having one or more (e.g. one, two or three) ring nitrogen atoms as the only ring heteroatoms, the heteroaryl group being optionally substituted by at least one substituent (e.g. one, two, three or four substituents) independently selected from halogen (e.g. fluorine, chlorine or bromine), cyano, $C_1$-$C_6$, or $C_1$-$C_4$, or $C_1$-$C_2$ alkyl, $C_2$-$C_6$ or $C_2$-$C_4$ alkenyl, $C_2$-$C_6$ or $C_2$-$C_4$ alkynyl. $C_1$-$C_6$, or $C_1$-$C_4$, or $C_1$-$C_2$ haloalkyl, $C_1$-$C_6$, or $C_1$-$C_4$, or $C_1$-$C_2$ hydroxyalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, $C_1$-$C_6$, or $C_1$-$C_4$, or $C_1$-$C_2$ alkylsulphinyl, $C_1$-$C_6$, or $C_1$-$C_4$, or $C_1$-$C_2$ alkylsulphonyl, $C_1$-$C_6$, or $C_1$-$C_4$, or $C_1$-$C_2$ alkylcarbonyl, $C_1$-$C_6$, or $C_1$-$C_4$, or $C_1$-$C_2$ alkylcarbonyloxy, $C_1$-$C_6$, or $C_1$-$C_4$, or $C_1$-$C_2$ alkoxycarbonyl, —$NR^{10}R^{11}$, —$CONR^{12}R^{13}$, $C_3$-$C_6$ cycloalkyl, $C_3$-$C_6$ cycloalkyloxy or $C_3$-$C_6$ cycloalkylmethyl.

The term "heteroaryl", as used herein, refers to an aromatic monocyclic heterocyclic group having a total of from 5 to 6 ring atoms, of which one to four ring atoms are heteroatoms selected from nitrogen atoms only. Examples of heteroaryl groups include pyrrolyl, imidazolyl, pyrazolyl, triazolyl, tetrazolyl, pyridinyl, pyrazinyl, pyrimidinyl, pyridazinyl and triazinyl. Preferred heteroaryl groups include pyridinyl, pyridazinyl and pyrazolyl, especially 4-pyridinyl, 4-pyridazinyl and 4-pyrazolyl.

In one embodiment, $R^5$ represents a 5- and/or 6-membered heteroaryl group having one or more (e.g. one, two or three) ring nitrogen atoms, the heteroaryl group being optionally substituted by at least one substituent (e.g. one, two, three or four substituents) independently selected from halogen (e.g. fluorine, chlorine or bromine), cyano. $C_1$-$C_4$, or $C_1$-$C_3$, or $C_1$-$C_2$ alkyl, $C_1$-$C_2$ haloalkyl, $C_1$-$C_2$ hydroxyalkyl, $C_1$-$C_4$, or $C_1$-$C_3$, or $C_1$-$C_2$ alkoxy, $C_1$-$C_2$ haloalkoxy, $C_1$-$C_2$ alkylsulphinyl, $C_1$-$C_2$ alkylsulphonyl, $C_1$-$C_2$ alkylcarbonyl, $C_1$-$C_2$ alkylcarbonyloxy, $C_1$-$C_2$ alkoxycarbonyl, —$NR^{10}R^{11}$. $CONR^{12}R^{13}$, $C_3$-$C_6$ or $C_3$-$C_5$ or $C_5$-$C_6$ cycloalkyl, $C_3$-$C_6$ or $C_3$-$C_5$ or $C_5$-$C_6$ cycloalkyloxy or $C_3$-$C_6$ or $C_3$-$C_5$ or $C_5$-$C_6$ cycloalkylmethyl.

In a further embodiment, $R^5$ represents a 5- and/or 6-membered heteroaryl group having one or more (e.g. one, two or three) ring nitrogen atoms, the heteroaryl group being optionally substituted by at least one substituent (e.g. one, two, three or four substituents) independently selected from halogen (e.g. fluorine, chlorine or bromine), $C_1$-$C_4$, or $C_1$-$C_3$, or $C_1$-$C_2$ alkyl, $C_1$-$C_4$, or $C_1$-$C_3$, or $C_1$-$C_2$ alkoxy. —$NR^{10}R^{11}$ or $C_3$-$C_6$ or $C_3$-$C_5$ or $C_5$-$C_6$ cycloalkyl.

In a still further embodiment, $R^5$ represents a 5- and/or 6-membered heteroaryl group having one or more (e.g. one, two or three) ring nitrogen atoms such as pyridinyl (particularly 4-pyridinyl), pyridazinyl (particularly 4-pyridazinyl) or pyrazolyl (particularly 4-pyrazolyl), the heteroaryl group being optionally substituted by one, two or three substituents independently selected from halogen (particularly chlorine), $C_1$-$C_3$ alkyl, $C_1$-$C_2$ alkoxy, —$NR^{10}R^{11}$ and $C_3$-$C_6$ cycloalkyl (particularly cyclopropyl).

In a preferred embodiment, $R^5$ represents any one of the following moieties or is selected from a group containing two or more of such moieties in any combination:
 (i) 2-(methylamino)pyridin-4-yl
 (ii) 2-(dimethylamino)pyridin-4-yl,
 (iii) 2-(ethyl(methyl)amino)pyridin-4-yl,
 (iv) 2-(propyl(methyl)amino)pyridin-4-yl.
 (v) 2-(isopropyl(methyl)amino)pyridin-4-yl.
 (vi) 2-(cyclopropyl(methyl)amino)pyridin-4-yl,
 (vii) 2-(cyclopropyl)pyridin-4-yl,
 (viii) 2-methylpyridin-4-yl,
 (ix) 2,6-dimethylpyridin-4-yl.
 (x) 2-ethylpyridin-4-yl,
 (xi) 2-isopropylpyridin-4-yl,
 (xii) 2-(isopropylamino)pyridin-4-yl,
 (xiii) 2-methoxypyridin-4-yl,
 (xiv) 2-ethoxypyridin-4-yl,
 (xv) 2-(azetidin-1-yl)pyridin-4-yl,
 (xvi) 2-(3-hydroxyazetidin-1-yl)pyridin-4-yl.
 (xvii) 2-(3,3-difluoroazetidin-1-yl)pyridin-4-yl.
 (xviii) 2-(pyrrolidin-1-yl)pyridin-4-yl.
 (xix) 2-chloropyridin-4-yl,
 (xx) 6-(methylamino)pyridazin-4-yl,
 (xxi) 6-(dimethylamino)pyridazin-4-yl,
 (xxii) 6-methylpyridazin-4-yl,
 (xxiii) 6-methoxypyridazin-4-yl.
 (xxiv) 6-(azetidin-1-yl)pyridazin-4-yl,
 (xxv) pyrazol-4-yl,
 (xxvi) 1-methylpyrazol-4-yl.
 (xxvii) 1,3-dimethylpyrazol-4-yl,
 (xxviii) 1-ethylpyrazol-4-yl,
 (xxix) 1-isopropylpyrazol-4-yl,
 (xxx) 5-amino-1-methylpyrazol-4-yl, and
 (xxxi) 3-amino-1-methylpyrazol-4-yl.

$R^6$ and $R^7$ each independently represent a hydrogen atom or a $C_1$-$C_6$, or $C_1$-$C_4$, or $C_1$-$C_2$ alkyl or $C_3$-$C_6$ or $C_3$-$C_5$ or $C_5$-$C_6$ cycloalkyl group, or $R^6$ and $R^7$ may together with the nitrogen atom to which they are attached form a 4-, 5-, 6- or 7-membered saturated heterocyclic ring optionally substituted by one or more (e.g. one or two) substituents independently selected from halogen (e.g. fluorine, chlorine or bromine) and hydroxyl.

In one aspect, the saturated heterocyclic ring may contain a single ring heteroatom (being the nitrogen atom to which $R^6$ and $R^7$ are attached). In an alternative aspect, the saturated heterocyclic ring may contain a second ring heteroatom selected from a nitrogen or oxygen atom.

In a first embodiment, $R^6$ and $R^7$ each independently represent a hydrogen atom or a $C_1$-$C_4$, or $C_1$-$C_3$, or $C_1$-$C_2$ alkyl or $C_3$-$C_6$, particularly cyclopropyl, group, or $R^6$ and $R^7$ may together with the nitrogen atom to which they are attached form a 4- or 5-membered saturated heterocyclic ring (azetidinyl or pyrrolidinyl) optionally substituted by one or two substituents independently selected from halogen (e.g. fluorine, chlorine or bromine, in particular fluorine) and hydroxyl.

In a second embodiment, $R^6$ and $R^7$ each represent a hydrogen atom.

In a third embodiment, $R^6$ and $R^7$ each represent a $C_1$-$C_3$ alkyl group.

In a fourth embodiment, one of $R^6$ and $R^7$ represents a hydrogen atom and the other of $R^6$ and $R^7$ represents a $C_1$-$C_3$ alkyl group.

In a fifth embodiment, one of $R^6$ and $R^7$ represents a cyclopropyl group and the other of $R^6$ and $R^7$ represents a $C_1$-$C_3$ alkyl group.

In a sixth embodiment, $R^6$ and $R^7$ together with the nitrogen atom to which they are attached form an azetidinyl or pyrrolidinyl ring optionally substituted by one or two substituents independently selected from fluorine and hydroxyl.

$R^8$ and $R^9$ each independently represent a hydrogen atom or a $C_1$-$C_6$, or $C_1$-$C_4$, or $C_1$-$C_2$ alkyl group, or $R^8$ and $R^9$ may together with the nitrogen atom to which they are attached form a 4- to 7-membered saturated heterocyclic ring.

In an embodiment of the invention, $R^8$ and $R^9$ each independently represent a hydrogen atom or a methyl group.

$R^{10}$ and $R^{11}$ each independently represent a hydrogen atom or a $C_1$-$C_6$, or $C_1$-$C_4$, or $C_1$-$C_2$ alkyl or $C_3$-$C_6$ or $C_3$-$C_5$ or $C_5$-$C_6$ cycloalkyl group, or $R^{10}$ and $R^{11}$ may together with the nitrogen atom to which they are attached form a 4-, 5-, 6- or 7-membered saturated heterocyclic ring optionally substituted by one or more (e.g. one or two) substituents independently selected from halogen (e.g. fluorine, chlorine or bromine) and hydroxyl.

In one aspect, the saturated heterocyclic ring may contain a single ring heteroatom (being the nitrogen atom to which $R^{10}$ and $R^{11}$ are attached). In an alternative aspect, the saturated heterocyclic ring may contain a second ring heteroatom selected from a nitrogen or oxygen atom.

In a first embodiment, $R^{10}$ and $R^{11}$ each independently represent a hydrogen atom or a $C_1$-$C_4$, or $C_1$-$C_3$, or $C_1$-$C_2$ alkyl or $C_3$-$C_6$, particularly cyclopropyl, group, or $R^{10}$ and $R^{11}$ may together with the nitrogen atom to which they are attached form a 4- or 5-membered saturated heterocyclic ring (azetidinyl or pyrrolidinyl) optionally substituted by one or two substituents independently selected from halogen (e.g. fluorine, chlorine or bromine, in particular fluorine) and hydroxyl.

In a second embodiment, $R^{10}$ and $R^{11}$ each represent a hydrogen atom. In this embodiment, $R^5$ preferably represents a 5-membered heteroaryl ring and not a 6-membered heteroaryl ring.

In a third embodiment, $R^{10}$ and $R^{11}$ each represent a $C_1$-$C_3$ alkyl group.

In a fourth embodiment, one of $R^{10}$ and $R^{11}$ represents a hydrogen atom and the other of $R^{10}$ and $R^{11}$ represents a $C_1$-$C_3$ alkyl group.

In a fifth embodiment, one of $R^{10}$ and $R^{11}$ represents a cyclopropyl group and the other of $R^{10}$ and $R^{11}$ represents a $C_1$-$C_3$ alkyl group.

In a sixth embodiment, $R^{10}$ and $R^{11}$ together with the nitrogen atom to which they are attached form an azetidinyl or pyrrolidinyl ring optionally substituted by one or two substituents independently selected from fluorine and hydroxyl.

$R^{12}$ and $R^{13}$ each independently represent a hydrogen atom or a $C_1$-$C_6$, or $C_1$-$C_4$, or $C_1$-$C_2$ alkyl group, or $R^{12}$ and $R^{13}$ may together with the nitrogen atom to which they are attached form a 4- to 7-membered saturated heterocyclic ring.

In an embodiment of the invention, $R^{12}$ and $R^{13}$ each independently represent a hydrogen atom or a methyl group.

Subject to the above provisos, preferred compounds of formula (I) are those in which:

$R^1$ represents a $C_5$-$C_{10}$ aryl group which is optionally substituted by at least one substituent independently selected from halogen, cyano, $C_1$-$C_6$ alkyl, $C_1$-$C_6$ haloalkyl, $C_1$-$C_6$ alkoxy or $C_1$-$C_6$ haloalkoxy;

R² represents a hydrogen atom or a hydroxyl group and R³ represents a hydrogen atom, or R² and R³ may together form a carbon-carbon bond;

X represents $CH_2$;

m is 1 or 2;

R⁵ represents a 5- to 6-membered heteroaryl group having one or more ring nitrogen atoms as the only ring heteroatoms (particularly 4-pyridinyl, 4-pyridazinyl or 4-pyrazolyl), the heteroaryl group being optionally substituted by at least one substituent independently selected from halogen, $C_1$-$C_6$ alkyl, $C_1$-$C_6$ alkoxy, —NR¹⁰R¹¹ or $C_3$-$C_6$ cycloalkyl; and R¹⁰ and R¹¹ each independently represent a hydrogen atom or a $C_1$-$C_6$ alkyl or $C_3$-$C_6$ cycloalkyl group, or R¹⁰ and R¹¹ may together with the nitrogen atom to which they are attached form a 4- to 7-membered saturated heterocyclic ring optionally substituted by halogen or hydroxyl.

Examples of preferred compounds of formula (I) according to the invention include:

4-{[3-(2-Fluorophenyl)piperidin-1-yl]carbonyl}-N,N-dimethylpyridin-2-amine,
4-{[3-(2,4-Dichlorophenyl)piperidin-1-yl]carbonyl}-N,N-dimethylpyridin-2-amine,
4-{[3-(4-Chlorophenyl)piperidin-1-yl]carbonyl}-2-cyclopropylpyridine,
4-{[3-(4-Chloro-2-methylphenyl)piperidin-1-yl]carbonyl}-2-ethylpyridine,
4-{[3-(4-Chloro-2-methylphenyl)piperidin-1-yl]carbonyl}-2-methylpyridine,
4-({3-[4-Chloro-2-(trifluoromethyl)phenyl]piperidin-1-yl}carbonyl)-2-ethylpyridine,
4-({3-[4-Chloro-2-(trifluoromethyl)phenyl]piperidin-1-yl}carbonyl)-N,N-dimethylpyridin-2-amine,
4-{[3-(4-Chlorophenyl)piperidin-1-yl]carbonyl}-N-(propan-2-yl)pyridin-2-amine,
4-({3-[4-Chloro-2-(trifluoromethyl)phenyl]piperidin-1-yl}carbonyl)-2-methoxypyridine,
4-({3-[4-Chloro-2-(trifluoromethyl)phenyl]piperidin-1-yl}carbonyl)-2-methylpyridine,
N-Methyl-4-{[3-(4-methylphenyl)piperidin-1-yl]carbonyl}pyridin-2-amine,
2-Methyl-4-{[3-(4-methylphenyl)piperidin-1-yl]carbonyl}pyridine,
N,N-Dimethyl-4-{[3-(3-methylphenyl)piperidin-1-yl]carbonyl}pyridin-2-amine,
N,N-Dimethyl-4-{[3-(2-methylphenyl)piperidin-1-yl]carbonyl}pyridin-2-amine,
N,N-Dimethyl-4-[(3-phenylpiperidin-1-yl)carbonyl]pyridin-2-amine,
4-{[3-(4-Chlorophenyl)piperidin-1-yl]carbonyl}-N,N-dimethylpyridin-2-amine,
4-{([3S)-3-(4-Chlorophenyl)piperidin-1-yl]carbonyl}-N,N-dimethylpyridin-2-amine,
4-{[(3R)-3-(4-Chlorophenyl)piperidin-1-yl]carbonyl}-N,N-dimethylpyridin-2-amine,
4-{[3-(4-Fluorophenyl)piperidin-1-yl]carbonyl}-N,N-dimethylpyridin-2-amine,
2-Ethyl-4-{[3-(4-methylphenyl)piperidin-1-yl]carbonyl}pyridine,
2-(Azetidin-1-yl)-4-{[3-(4-methylphenyl)piperidin-1-yl]carbonyl}pyridine,
2-(Azetidin-1-yl)-4-{[3-(4-chlorophenyl)piperidin-1-yl]carbonyl}pyridine,
2-(Azetidin-1-yl)-4-{[3-(2-methylphenyl)piperidin-1-yl]carbonyl}pyridine,
4-{[3-(4-Chloro-2-methylphenyl)piperidin-1-yl]carbonyl}-N,N-dimethylpyridin-2-amine,
4-{[3-(4-Chloro-2-fluorophenyl)piperidin-1-yl]carbonyl}-N,N-dimethylpyridin-2-amine,
4-{[3-(2-Chloro-4-fluorophenyl)piperidin-1-yl]carbonyl}-N,N-dimethylpyridin-2-amine,
4-{[3-(4-Chlorophenyl)piperidin-1-yl]carbonyl}-N-methylpyridin-2-amine,
4-{[3-(4-Chlorophenyl)piperidin-1-yl]carbonyl}-2,6-dimethylpyridin,
2-Chloro-4-{[3-(4-chlorophenyl)piperidin-1-yl]carbonyl}pyridine,
4-{[3-(4-Chlorophenyl)piperidin-1-yl]carbonyl}-2-(propan-2-yl)pyridine,
4-{[3-(4-Chloro-2-methylphenyl)piperidin-1-yl]carbonyl}-N-methylpyridin-2-amine,
4-{[3-(4-Chloro-2-methylphenyl)piperidin-1-yl]carbonyl}-2-methoxypyridine,
2-(Azetidin-1-yl)-4-{[3-(4-chloro-2-methylphenyl)piperidin-1-yl]carbonyl}pyridine,
2-Methoxy-4-{([3-(4-methylphenyl)piperidin-1-yl]carbonyl}pyridine,
4-{[3-(4-Methylphenyl)piperidin-1-yl]carbonyl}-2-(pyrrolidin-1-yl)pyridine,
4{[(3S)-3-(3-Methoxyphenyl)piperidin-1-yl]carbonyl}-N,N-dimethylpyridin-2-amine,
N-Ethyl-N-methyl-4-{[3-(4-methylphenyl)piperidin-1-yl]carbonyl}pyridin-2-amine,
2-(3,3-Difluoroazetidin-1-yl)-4-{[3-(4-methylphenyl)piperidin-1-yl]carbonyl}pyridine,
N-Methyl-4-{[3-(4-methylphenyl)piperidin-1-yl]carbonyl}-N-propylpyridin-2-amine,
N-Methyl-4-{[3-(4-methylphenyl)piperidin-1-yl]carbonyl}-N-(propan-2-yl)pyridin-2-amine,
1-(4-{[3-(4-Methylphenyl)piperidin-1-yl]carbonyl}pyridin-2-yl)azetidin-3-ol,
4-{[3-(4-Chlorophenyl)piperidin-1-yl]carbonyl}-2-ethoxypyridine,
N-Cyclopropyl-N-methyl-4-{[3-(4-methylphenyl)piperidin-1-yl]carbonyl}pyridin-2-amine,
N,N-Dimethyl-4-({3-[4-(trifluoromethyl)phenyl]piperidin-1-yl}carbonyl)pyridin-2-amine,
N,N-Dimethyl-4-({3-[2-(trifluoromethyl)phenyl]piperidin-1-yl}carbonyl)pyridin-2-amine,
4-{[3-(2-Chlorophenyl)piperidin-1-yl]carbonyl}-N,N-dimethylpyridin-2-amine,
4-{[3-(4-Methoxyphenyl)piperidin-1-yl]carbonyl}-N,N-dimethylpyridin-2-amine,
4-{[3-(2-Methoxyphenyl)piperidin-1-yl]carbonyl}-N,N-dimethylpyridin-2-amine,
N,N-Dimethyl-4-{[3-(4-methylphenyl)piperidin-1-yl]carbonyl}pyridin-2-amine,
N,N-Dimethyl-4-{[3-(4-methylphenyl)piperidin-1-yl]carbonyl}pyridin-2-amine (Enantiomer 1 substantially as described herein and with reference to Example 50),
N,N-Dimethyl-4-{[3-(4-methylphenyl)piperidin-1-yl]carbonyl}pyridin-2-amine (Enantiomer 2 substantially as described herein and with reference to Example 51),
4-{[3-(4-Chlorophenyl)piperidin-1-yl]carbonyl}-2-ethylpyridine,
N-Methyl-4-({3-[4-(trifluoromethyl)phenyl]piperidin-1-yl}carbonyl)pyridin-2-amine,
N-Methyl-4-({(3-[2-(trifluoromethyl)phenyl]piperidin-1-yl}carbonyl)pyridin-2-amine,
4-{[3-(4-Methoxyphenyl)piperidin-1-yl]carbonyl}-N-methylpyridin-2-amine, 4-{[3-(2-Methoxyphenyl)piperidin-1-yl]carbonyl}-N-methylpyridin-2-amine,
4-({3-[4-Chloro-2-(trifluoromethyl)phenyl]piperidin-1-yl}carbonyl)-N-methylpyridin-2-amine,
2-Ethyl-4-({3-[2-(trifluoromethyl)phenyl]piperidin-1-yl}carbonyl)pyridine,
2-Ethyl-4-{[3-(2-methoxyphenyl)piperidin-1-yl]carbonyl}pyridine,
N,N-Dimethyl-4-({3-[2-(trifluoromethoxy)phenyl]piperidin-1-yl}carbonyl)pyridin-2-amine,
4-{[3-(4-Chloro-2-ethoxyphenyl)piperidin-1-yl]carbonyl}-N,N-dimethylpyridin-2-amine,
4-({3-[4-Methoxy-2-(trifluoromethyl)phenyl]piperidin-1-yl}carbonyl)-N,N-dimethylpyridin-2-amine,
4-{[3-(4-Methoxy-2-methylphenyl)piperidin-1-yl]carbonyl}-N-methylpyridin-2-amine,
4-({3-[4-Methoxy-2-(trifluoromethyl)phenyl]piperidin-1-yl}carbonyl)-N-methylpyridin-2-amine,
4-{[3-(4-Chloro-2-ethoxyphenyl)piperidin-1-yl]carbonyl}-N-methylpyridin-2-amine,
4-({3-[2-(Difluoromethoxy)phenyl]piperidin-1-yl}carbonyl)-N,N-dimethylpyridin-2-amine,
2-(1-{[2-(Dimethylamino)pyridin-4-yl]carbonyl}piperidin-3-yl)benzonitrile,
4-{[3-(4-Chloro-2,6-dimethylphenyl)piperidin-1-yl]carbonyl}-N,N-dimethylpyridin-2-amine,
5-{[3-(4-Chlorophenyl)piperidin-1-yl]carbonyl}-N,N-dimethylpyridazin-3-amine,
5-{[3-(4-Chloro-2-methylphenyl)piperidin-1-yl]carbonyl}-N,N-dimethylpyridazin-3-amine,
5-{[3-(4-Chloro-2-methylphenyl)piperidin-1-yl]carbonyl}-N-methylpyridazin-3-amine,
5-{[(3R)-3-(4-Chloro-2-methylphenyl)piperidin-1-yl]carbonyl}-N-methylpyridazin-3-amine
5-{[(3S)-3-(4-Chloro-2-methylphenyl)piperidin-1-yl]carbonyl}-N-methylpyridazin-3-amine
5-{[3-(4-Chloro-2-methylphenyl)piperidin-1-yl]carbonyl}-3-methoxypyridazine,
5-({3-[4-Chloro-2-(trifluoromethyl)phenyl]piperidin-1-yl}carbonyl)-N,N-dimethylpyridazin-3-amine,
5-({3-[4-Chloro-2-(trifluoromethyl)phenyl]piperidin-1-yl}carbonyl)-N-methylpyridazin-3-amine,
3-(Azetidin-1-yl)-5-({3-[4-chloro-2-(trifluoromethyl)phenyl]piperidin-1-yl}carbonyl)pyridazine,
5-({3-[2-Methoxy-4-(trifluoromethyl)phenyl]piperidin-1-yl}carbonyl)-N,N-dimethylpyridazin-3-amine,
5-{[3-(4-Methoxy-2-methylphenyl)piperidin-1-yl]carbonyl}-N-methylpyridazin-3-amine,
5-{[3-(4-Methoxy-2-methylphenyl)piperidin-1-yl]carbonyl}-N,N-dimethylpyridazin-3-amine,
5-({3-[4-Methoxy-2-(trifluoromethyl)phenyl]piperidin-1-yl}carbonyl)-N-methylpyridazin-3-amine,
5-({3-[4-Methoxy-2-(trifluoromethyl)phenyl]piperidin-1-yl}carbonyl)-N,N-dimethylpyridazin-3-amine,
5-{[3-(4-Chloro-2-ethoxyphenyl)piperidin-1-yl]carbonyl}-N-methylpyridazin-3-amine,
5-{[3-(4-Chloro-2-ethoxyphenyl)piperidin-1-yl]carbonyl}-N,N-dimethylpyridazin-3-amine,
5-{[3-(4-Chloro-2-methylphenyl)piperidin-1-yl]carbonyl}-3-methylpyridazine,
5-{[3-(2-Methoxyphenyl)piperidin-1-yl]carbonyl}-N-methylpyridazin-3-amine,
3-(4-Chloro-2-methylphenyl)-1-[(1,3-dimethyl-1H-pyrazol-4-yl)carbonyl]piperidine,
3-(4-Chlorophenyl)-1-[(1,3-dimethyl-1H-pyrazol-4-yl)carbonyl]piperidine,
3-(4-Chlorophenyl)-1-[(1-methyl-1H-pyrazol-4-yl)carbonyl]piperidine,
3-(4-Chlorophenyl)-1-[(1-ethyl-1H-pyrazol-4-yl)carbonyl]piperidine,
3-(4-Chlorophenyl)-1-{[-(propan-2-yl)-1H-pyrazol-4-yl]carbonyl}piperidine,
3-(4-Chloro-2-methylphenyl)-1-[(1-ethyl-1H-pyrazol-4-yl)carbonyl]piperidine,
3-(4-Chloro-2-methylphenyl)-1-{[1-(propan-2-yl)-1H-pyrazol-4-yl]carbonyl}piperidine,
3-(4-Chloro-2-methylphenyl)-1-[(1-methyl-1H-pyrazol-4-yl)carbonyl]piperidine,
4-{[(3-(4-Chloro-2-methylphenyl)piperidin-1-yl]carbonyl}-1-methyl-1H-pyrazol-5-amine,
3-[4-Chloro-2-(trifluoromethyl)phenyl]-1-[(1H-pyrazol-4-yl)carbonyl]piperidine,
3-[4-Chloro-2-(trifluoromethyl)phenyl]-1-[(1-methyl-1H-pyrazol-4-yl)carbonyl]piperidine,
3-[4-Chloro-2-(trifluoromethyl)phenyl]-1-[(1-ethyl-1H-pyrazol-4-yl)carbonyl]piperidine,
3-[4-Chloro-2-(trifluoromethyl)phenyl]-1-{[1-(propan-2-yl)-1H-pyrazol-4-yl]carbonyl}piperidine,
4-({3-[4-Chloro-2-(trifluoromethyl)phenyl]piperidin-1-yl}carbonyl)-1-methyl-1H-pyrazol-3-amine,
1-[(1,3-Dimethyl-1H-pyrazol-4-yl)carbonyl]-3-(4-methoxy-2-methylphenyl)piperidine,
4-{[3-(4-Methoxy-2-methylphenyl)piperidin-1-yl]carbonyl}-1-methyl-1H-pyrazol-3-amine,
3-[4-Chloro-2-(trifluoromethyl)phenyl]-1-[(1,3-dimethyl-1H-pyrazol-4-yl)carbonyl]piperidine,
4-{([5-(4-Chlorophenyl)-1,2,3,4-tetrahydropyridin-1-yl]carbonyl}-N,N-dimethylpyridin-2-amine,
4-{[5-(4-Chloro-2-methylphenyl)-1,2,3,4-tetrahydropyridin-1-yl]carbonyl}-N,N-dimethylpyridin-2-amine,
4-{[5-(2,4-Dichlorophenyl)-1,2,3,4-tetrahydropyridin-1-yl]carbonyl}-N,N-dimethylpyridin-2-amine,
N,N-Dimethyl-4-[(3-phenylazepan-1-yl)carbonyl]pyridin-2-amine,
4-{[3-(4-Chlorophenyl)azepan-1-yl]carbonyl}-N,N-dimethylpyridin-2-amine,
4-{[3-(4-Methoxyphenyl)azepan-1-yl]carbonyl}-N,N-dimethylpyridin-2-amine,
4-{[3-(4-Methoxyphenyl)azepan-1-yl]carbonyl}-N-methylpyridin-2-amine,
4-{[3-(4-Chlorophenyl)azepan-1-yl]carbonyl}-N-methylpyridin-2-amine,
5-{[3-(4-Methoxyphenyl)azepan-1-yl]carbonyl}-N-methylpyridazin-3-amine,
5-{[3-(4-Chlorophenyl)azepan-1-yl]carbonyl}-N-methylpyridazin-3-amine,
5-{[3-(4-Methoxyphenyl)azepan-1-yl]carbonyl}-N,N-dimethylpyridazin-3-amine,
5-{[3-(4-Chlorophenyl)azepan-1-yl]carbonyl}-N,N-dimethylpyridazin-3-amine,
1-[3-(4-Chloro-2-methylphenyl)piperidin-1-yl]-2-(3,5-dimethyl-1H-pyrazol-4-yl)ethan-1-one,
1-{3-[4-Chloro-2-(trifluoromethyl)phenyl]piperidin-1-yl}-2-(trimethyl-1H-pyrazol-4-yl)ethan-1-one,
1-{3-[4-Chloro-2-(trifluoromethyl)phenyl]piperidin-1-yl}-2-(3,5-dimethyl-1H-pyrazol-4-yl)ethan-1-one,
3-(4-Chloro-2-methylphenyl)-1-{[2-(dimethylamino)pyridin-4-yl]carbonyl}piperidin-3-ol,
1-{[2-(Dimethylamino)pyridin-4-yl]carbonyl}-3-(4-fluorophenyl)piperidin-3-ol, 4-({3-[4-Chloro-2-(trifluoromethyl)phenyl]piperidin-1-yl}carbonyl)-1-methyl-1H-pyrazol-3-amine (Enantiomer 1 substantially as described herein and with reference to Example 118), 4-({3-[4-Chloro-2-(trifluoromethyl)phenyl]piperidin-1-yl}carbonyl)-1-methyl-1H-pyrazol-3-amine (Enantiomer 2 substantially as described herein and with reference to Example 119).

and pharmaceutically acceptable salts of any one thereof.

It should be noted that each of the chemical compounds listed above represents a particular and independent aspect of the invention.

Compounds of formula (I) and pharmaceutically acceptable salts thereof as defined above may be prepared by a process comprising (i) reacting a compound of formula

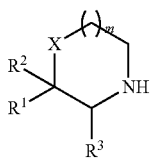

(II)

wherein m, X, $R^1$, $R^2$ and $R^3$ are as defined in formula (I) or a salt thereof (e.g. a hydrochloride salt), with a compound of formula

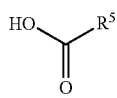

(III)

wherein $R^5$ is as defined in formula (I); or (ii) hydrogenating a compound of formula

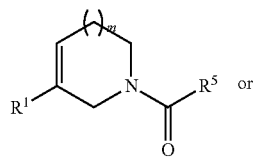

(IVa)

or

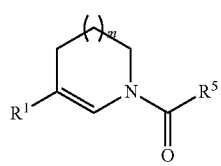

(IVb)

or a mixture thereof, in which m, $R^1$ and $R^5$ are as defined in formula (I); and optionally thereafter carrying out one or more of the following procedures:

removing any protecting groups converting a compound of formula (I) into another compound of formula (I)

forming a pharmaceutically acceptable salt.

Reaction conditions for process (i) above will typically require activation of the carboxylic acid of formula (III) which can be achieved by many of the widely known 'amide coupling' agents such as 1-ethyl-3-(3-dimethylaminopropyl) carbodiimide (EDC) or propylphosphonic anhydride (commercially available under the trade mark "T3P"). This can be carried out in a suitable solvent such as dichloromethane, in the presence of a base such as triethylamine. The compound of formula (II), or salt thereof, may be present during activation of the carboxylic acid of formula (III), or may be added a short while afterwards. The reactions will typically occur at ambient room temperature (20 to 25° C.).

As an alternative to carrying out the activation in situ, 'pre-activated' variants of the compound of formula (III) such as acid halides, acid anhydrides and esters (e.g. pentafluorophenyl esters) thereof can be used to react with the amine of formula (II) to form compounds of formula (I) under the appropriate conditions which will be known to the person skilled in the art.

Process (ii) above may be carried out according to methods known in the art, e.g by using hydrogen in the presence of a transition metal catalyst such as palladium on carbon.

Compounds of formula (II) in which $R^2$ is hydrogen. X is $CH_2$ and m is 1 may be prepared by reacting a compound of formula (V), $R^1$—$B(OR^{20})_2$, where $R^{20}$ represents a hydrogen atom, an alkyl group, or both groups $OR^{20}$ together with the boron atom to which they are attached form a dioxoborolane ring (such as a pinacol borane) or a N-methylimi-nodiacetic acid boronate ester (MIDA boronate ester), and $R^1$ is as defined in formula (II), with 3-iodopyridine or 3-bromopyridine in the presence of a palladium catalyst according to the Suzuki-Miyaura reaction (see, for example, the following references:

1. Miyaura, Norio; Yamada, Kinji; Suzuki, Akira (1979). "A new stereospecific cross-coupling by the palladium-catalyzed reaction of 1-alkenylboranes with 1-alkenyl or 1-alkynyl halides". *Tetrahedron Letters* 20 (36): 3437-3440.

2. Miyaura. Norio; Suzuki, Akira (1979). "Stereoselective synthesis of arylated (E)-alkenes by the reaction of alk-1-enylboranes with aryl halides in the presence of palladium catalyst". *Chem. Comm.* (19): 866-867.

3. Miyaura, Norio; Suzuki, Akira (1995). "Palladium-Catalyzed Cross-Coupling Reactions of Organoboron Compounds". *Chemical Reviews* 95 (7): 2457-2483.

followed by a reduction step using hydrogen gas and a platinum (IV) oxide catalyst.

Alternatively, compounds of formula (II) in which $R^2$ is hydrogen. X is $CH_2$ and m is 1 may be prepared as illustrated in Scheme 1 below:

Scheme 1

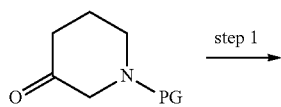

step 1

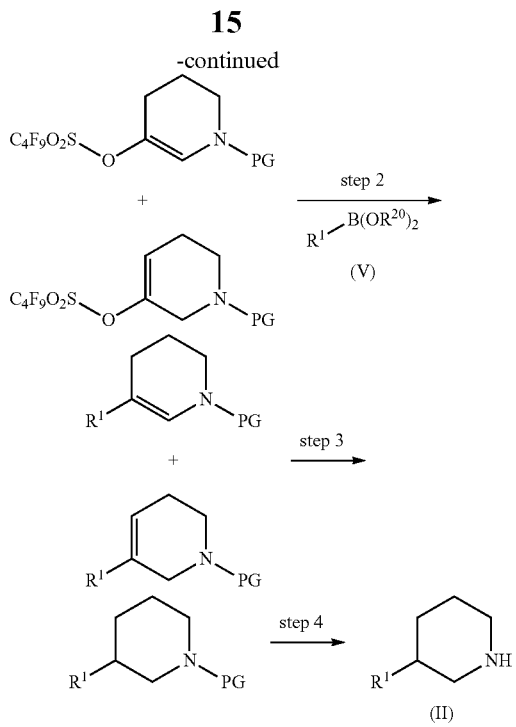

In Scheme 1, 'PG' denotes a nitrogen-protecting group. Step 1 is carried out in the presence of lithium bis(trimethylsilyl)amide and 1,1,2,2,3,3,4,4,4-nonafluorobutane-1-sulfonyl fluoride. The reaction product obtained can be a mixture of enol nonaflate isomers which, individually or taken as a mixture, is then reacted in step 2 with a compound of formula (IV) as described above under Suzuki-Miyaura reaction conditions. The product of step 2 is hydrogenated in step 3 using, for example, transition metal catalysed hydrogenation (e.g. palladium on carbon, Pd(OH)$_2$ on carbon, or platinum (IV) oxide) and, finally, the protecting group is removed in step 4, for example, using trifluoroacetic acid or hydrochloric acid in dichloromethane, when PG is tert-butoxycarbonyl (Boc) to give a compound of formula (II). Alternatively, where PG is benzyl or 4-methoxy benzyl, the deprotection may occur concomitantly with hydrogenation, or may proceed stepwise, typically effected by raising either the temperature and/or pressure of hydrogenation and/or by extending the reaction time of hydrogenation such that hydrogenolysis of the PG also occurs. Alternatively, where PG is benzyl or 4-methoxy benzyl, the deprotection may be effected by treatment with α-chloroethyl chloroformate (ACE-Cl) in a suitable solvent such as dichloromethane or dichloroethane followed by treatment with methanol according to the protocol of Olofson as described in the following reference: Olofson, Martz (1984). "A New Reagent for the Selective, High-Yield N-Dealkylation of Tertiary Amines: Improved Syntheses of Naltrexone and Nalbuphine". *J. Org. Chem.* 49: 2081-2082.

Compounds of formula (II) in which R$^2$ is hydrogen, X is CH$_2$ and m is 2 are commercially available or may be prepared using known techniques.

Compounds of formula (II) in which R$^2$ is other than hydrogen may be prepared as illustrated in Scheme 2 below:

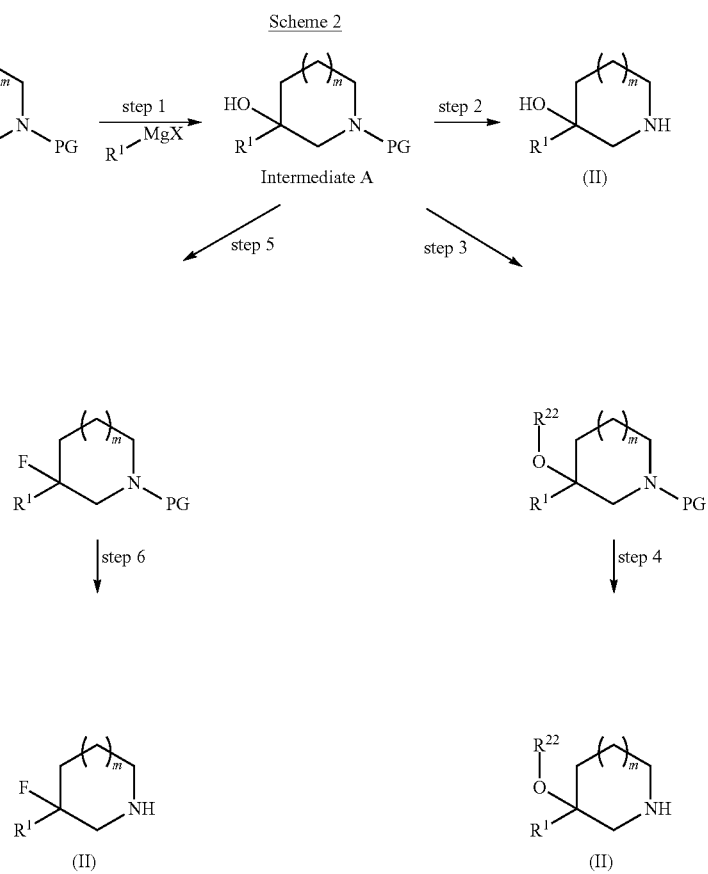

In Scheme 2, 'PG' denotes a nitrogen-protecting group, $R^{22}$ denotes a $C_1$-$C_3$ alkyl group and 'm' and '$R^1$' have the same meanings as in formula (I). Step 1 is carried out in the presence of an organometallic reagent (eg aryl Grignard. $R^1$-MgX) and then the protecting group is removed in step 2, for example, using trifluoroacetic acid or hydrochloric acid in dichloromethane when PG is tert-butoxycarbonyl (Boc) to give a compound of formula (II) in which $R^2$ represents hydroxyl. Alternatively the product from step 1 (Intermediate A) can be alkylated (e.g. using a $C_1$-$C_3$ alkyl halide and a strong base. e.g. sodium hydride) (step 3) and the protecting group removed in step 4 by a procedure analogous to step 2 to give compounds of formula (II) in which $R^2$ represents $C_1$-$C_3$ alkoxy. Intermediate A may also be treated with a fluorinating agent (e.g. diethylaminosulfur trifluoride) (step 5) followed by removal of the protecting group in step 6 using a procedure analogous to step 2 to give a compound of formula (II) in which $R^2$ represents fluorine.

Compounds of formula (II) in which either $R^2$ and $R^3$ form a carbon-carbon bond or $R^2$ and $R^4$ form a carbon-carbon bond can be prepared by treating the product obtained from step 2 of Scheme 1 above with ACE-Cl followed by methanol (vide supra) to remove the protecting group.

Compounds of formulae (IVa) and (IVb) may be prepared as illustrated in Scheme 3 below:

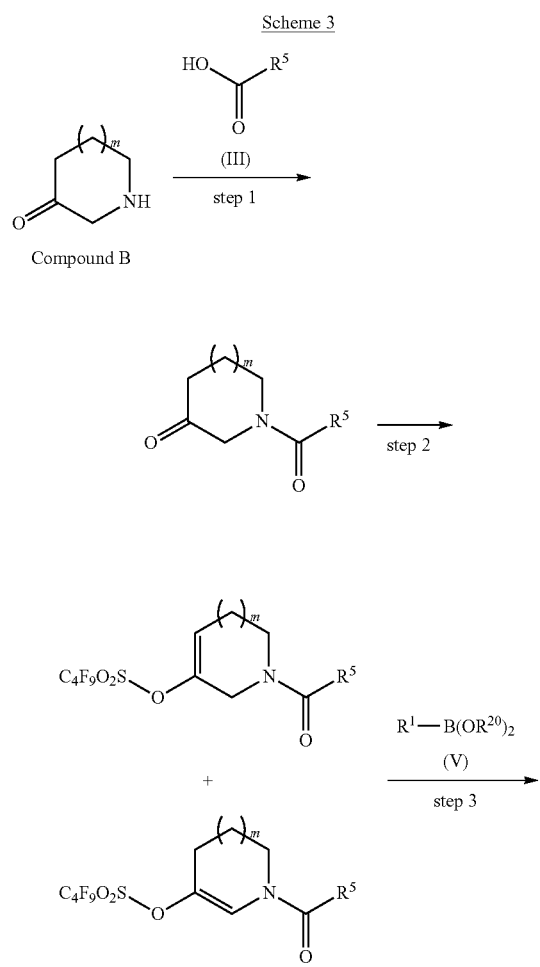

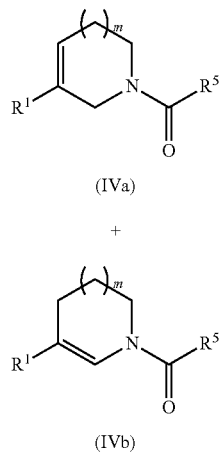

In Scheme 3, 'm', '$R^1$' and '$R^5$' have the same meanings as in formula (I). In step 1. Compound B, e.g. piperidine-3-one or a suitable salt thereof (e.g. hydrochloride), is reacted with a compound of formula (III) as defined above under suitable amide coupling conditions (e.g. EDC or T3P® vide supra). The resulting amide is converted in step 2 to the corresponding enol nonaflate isomers in the presence of, for example, lithium bis(trimethylsilyl)amide and 1,1,2,2,3,3,4,4,4-nonafluorobutane-1-sulfonyl fluoride. The isomers, individually or as a mixture, are then reacted in step 3 with a compound of formula (V) as defined above under Suzuki-Miyaura reaction conditions to give the corresponding compounds of formulae (IVa) and (IVb), individually, or as a mixture of isomers.

Compounds of formulae (III) and (V) are either commercially available, are well known in the literature or may be prepared using known techniques.

It will be appreciated by those skilled in the art that in the above processes certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J.W.F. McOmie, Plenum Press (1973) and 'Protective Groups in Organic Synthesis', 3$^{rd}$ edition, T. W. Greene and P.G.M. Wuts, Wiley-Interscience (1999).

The compounds of formula (I) above may be converted to a pharmaceutically acceptable salt thereof, preferably an acid addition salt such as a formate, hemi-formate, hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) defined above may bear one or more radiolabels. Such radiolabels may be introduced by using radiolabel-containing reagents in the synthesis of the compounds of formula (I) or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1H$, $^2H$ and $^3H$. Similarly carbon atoms are to be understood to include $^{12}C$, $^{13}C$ and $^{14}C$, nitrogen atoms are to be understood to include $^{14}N$ and $^{15}N$, and oxygen atoms are to be understood to include $^{16}O$, $^{17}O$ and $^{18}O$.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) above are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as prokineticin receptor modulators, and thus may be used in the treatment of schizophrenia and other psychotic disorders (e.g., schizophreniform disorder, schizoaffective disorder and psychosis): dementia (including behavioural and psychological symptoms of dementia, BPSD) and other cognitive disorders; anxiety disorders (e.g., generalized anxiety disorder, post-traumatic stress disorder and panic attack); mood disorders (e.g., depressive disorders, major depressive disorders, bipolar disorders including bipolar I and II, bipolar mania, bipolar depression); sleep disorders; disorders usually first diagnosed in infancy, childhood, or adolescence (e.g., attention-deficit disorder, autistic spectrum disorders, Rett syndrome, Fragile X syndrome, Asperger syndrome and disruptive behaviour disorders); pain (e.g. neuropathic pain including chemotherapy induced pain, or visceral pain, or gastrointestinal pain); inflammatory conditions such as inflammatory bowel disease (e.g. Crohn's disease, Coeliac disease, ileitis, ulcerative colitis, enteropathy associated with seronegative arthropathies, microscopic or collagenous colitis, eosinophilic gastroenteritis, or pouchitis resulting after proctocolectomy and ileoanal anastomosis), cholecystitis, cholangitis, Behcet's disease, pericholangitis, graft versus host disease, sarcoidosis and chronic gastritis (e.g., autoimmune gastritis); neurodegenerative disorders (e.g. Parkinson's or Alzheimer's disease or multiple sclerosis); gastrointestinal disorders (e.g. irritable bowel syndrome (IBS) and functional dyspepsia); autoimmune disorders (e.g. rheumatoid arthritis); and addiction (e.g. drug addiction, alcohol addiction and nicotine addiction).

Thus, the present invention provides a compound of formula (I) or a pharmaceutically acceptable salt thereof as hereinbefore defined for use in therapy, in particular for the treatment of conditions whose development or symptoms are linked to prokineticin receptor activity.

The present invention also provides the use of a compound of formula (I) or a pharmaceutically acceptable salt thereof as hereinbefore defined for the preparation of a medicament for the treatment of conditions whose development or symptoms are linked to prokineticin receptor activity.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of formula (I) and their pharmaceutically acceptable salts as defined above may be used in the treatment of the positive symptoms of schizophrenia, schizophreniform disorder or schizoaffective disorder (e.g. voices or hallucinations), cognitive disorders (such as dementia and impaired learning) and also pain (such as neuropathic pain).

The invention also provides a method of treating at least one symptom or condition associated with schizophrenia and other psychotic disorders (e.g., schizophreniform disorder, schizoaffective disorder and psychosis); dementia (including behavioural and psychological symptoms of dementia. BPSD) and other cognitive disorders; anxiety disorders (e.g., generalized anxiety disorder, post-traumatic stress disorder and panic attack); mood disorders (e.g., depressive disorders, major depressive disorders, bipolar disorders including bipolar I and II, bipolar mania, bipolar depression); sleep disorders; disorders usually first diagnosed in infancy, childhood, or adolescence (e.g., attention-deficit disorder, autistic spectrum disorders. Rett syndrome, Fragile X syndrome, Asperger syndrome and disruptive behaviour disorders); pain (e.g. neuropathic pain including chemotherapy induced pain, or visceral pain, or gastrointestinal pain); inflammatory conditions such as inflammatory bowel disease (e.g. Crohn's disease. Coeliac disease, ileitis, ulcerative colitis, enteropathy associated with seronegative arthropathies, microscopic or collagenous colitis, eosinophilic gastroenteritis, or pouchitis resulting after proctocolectomy and ileoanal anastomosis), cholecystitis, cholangitis, Behcet's disease, pericholangitis, graft versus host disease, sarcoidosis and chronic gastritis (e.g., autoimmune gastritis); neurodegenerative disorders (e.g. Parkinson's or Alzheimer's disease or multiple sclerosis); gastrointestinal disorders (e.g. irritable bowel syndrome (IBS) and functional dyspepsia); autoimmune disorders (e.g. rheumatoid arthritis); and addiction (e.g. drug addiction, alcohol addiction and nicotine addiction) which comprises administering to a patient in need thereof a therapeutically effective amount of a compound of formula (I) or a pharmaceutically acceptable salt thereof as hereinbefore defined. Such symptoms and conditions include, but are not limited to, anxiety, agitation, hostility, panic, an eating disorder, an affective symptom, a mood symptom, a negative and positive psychotic symptom commonly associated with psychosis and neurodegenerative disorder.

For the above-mentioned therapeutic uses the dosage administered will, of course, vary with the compound employed, the mode of administration, the treatment desired and the disorder indicated. For example, the daily dosage of a compound according to the invention (i.e. a compound of formula (I) or a pharmaceutically acceptable salt thereof), if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of formula (I) and pharmaceutically acceptable salts thereof as defined above may also be administered in conjunction with other compounds used for the treatment of the above conditions.

The invention therefore further relates to combination therapies wherein a compound of formula (I) or a pharmaceutically acceptable salt thereof as previously defined or a pharmaceutical composition or formulation comprising a compound of formula (I) or a pharmaceutically acceptable salt thereof as previously defined is administered with another therapeutic agent or agents, for the treatment of one or more of the conditions previously indicated. Such therapeutic agents may be selected from the following:

(i) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, and equivalents and pharmaceutically active isomer(s) and/or metabolite(s) thereof;

(ii) atypical antipsychotics including, for example, quetiapine and pharmaceutically active isomer(s) and/or metabolite(s) thereof;

(iii) antipsychotics including, for example, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone, and equivalents and pharmaceutically active isomer(s) and/or metabolite(s) thereof;

(iv) anxiolytics including, for example, alnespirone, azapirones, benzodiazepines, barbiturates, and equivalents and pharmaceutically active isomer(s) and/or metabolite(s) thereof, Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or to metabolite(s) thereof:

(v) anticonvulsants including, for example, carbamazepine, valproate, lamotrigine, and gabapentin, and equivalents and pharmaceutically active isomer(s) and/or metabolite(s) thereof;

(vi) Alzheimer's therapies including, for example, donepezil, memantine, tacrine, and equivalents and pharmaceutically active isomer(s) and/or metabolite(s) thereof:

(vii) Parkinson's therapies including, for example, deprenyl, L-dopa, Requip, Mirapex, monoamine oxidase type B (MAO-B) inhibitors such as selegiline and rasagiline, catechol-O-methyl transferase (COMT) inhibitors such as Tasmar, A-2 inhibitors, dopamine re-uptake inhibitors, NMDA antagonists, Nicotine agonists, and Dopamine agonists and inhibitors of neuronal nitric oxide synthase, and equivalents and pharmaceutically active isomer(s) and/or metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof:

(ix) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;

(x) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof:

(xi) neuropathic pain therapies including, for example, gabapentin, lidoderm, and pregablin, and equivalents and pharmaceutically active isomer(s) and/or metabolite(s) thereof;

(xii) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, and Zolpidem, and equivalents and pharmaceutically active isomer(s) and/or metabolite(s) thereof;

(xiv) mood stabilizers including, for example, carbamazepine, divalproex, gabapentin, lamotrigine, lithium, olanzapine, quetiapine, valproate, valproic acid, and verapamil, and equivalents and pharmaceutically active isomer(s) and/ or metabolite(s) thereof;

(xv) 5HT1B ligands such as, for example, compounds disclosed in WO 99/05134 and WO 02/08212;

(xvi) mGluR$^2$ agonists;

(xvii) alpha 7 nicotinic agonists such as, for example, compounds disclosed in WO 96/006098, WO 97/030998, WO 99/003859, WO 00/042044, WO 01/029034, WO 01/60821, WO 01/36417, WO 02/096912, WO 03/087102, WO 03/087103, WO 03/087104, WO 2004/016617, WO 2004/016616, and WO 2004/019947;

(xviii) chemokine receptor CCR1 inhibitors; and (xix) delta opioid agonists such as, for example, compounds disclosed in WO 97/23466 and WO 02/094794.

Such combination products employ the compound of formula (I) or a pharmaceutically acceptable salt thereof as previously defined within the dosage range described herein and the other pharmaceutically active agent within approved dosage ranges and/or the dosage such as described in the publication reference.

In a further aspect the present invention provides a combination (for example for the treatment of schizophrenia, cognitive disorders or pain) of a compound of formula (I) or a pharmaceutically acceptable salt thereof as hereinbefore defined and one or more agents independently selected from carbamazepine, olanzapine, quetiapine, verapamil, lamotrigine, oxcarbazepine, risperidone, aripiprazole, ziprasidone and lithium.

The invention also provides a pharmaceutical product comprising, in combination, a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, for simultaneous, sequential or separate use in therapy.

In another aspect, the invention provides a kit comprising a preparation of a first active ingredient which is a compound of formula (I) or a pharmaceutically acceptable salt thereof as hereinbefore defined, and a preparation of a second active ingredient which is carbamazepine, olanzapine, quetiapine, verapamil, lamotrigine, oxcarbazepine, risperidone, aripiprazole, ziprasidone or lithium, and instructions for the simultaneous, sequential or separate administration of the preparations to a patient in need thereof.

The present invention will now be further explained by reference to the following illustrative examples, in which the starting materials and reagents used are available from commercial suppliers. In the illustrative examples, the compounds synthesised are both named and illustrated structurally. Whilst every effort has been made to ensure that the chemical names and the chemical structures are consistent, if any inconsistencies occur the illustrated chemical structure should be taken to be correct, unless the illustrated chemical structure is chemically impossible.

Nuclear magnetic resonance (NMR) spectra were recorded at 400 MHz and at 300.3K unless otherwise stated; the chemical shifts ($\delta$) are reported in parts per million. Spectra were recorded using either a Bruker 400 Avance instrument fitted with a 5 mm BBFO probe or DUL probe with instrument controlled by Bruker TopSpin 2.1 software, or by a Jeol Lambda spectrometer (JN-LMA400) instrument fitted with a 5 mm Jeol TH5 probe with instrument controlled by Jeol Delta software v4.3.5.

In respect of NMR analysis, compounds of the formula (I) frequently exhibit signal splitting and/or broadening due to conformationally restricted motion of the pendant substituents of the N-acyl piperidine/azepine ring. These effects are temperature and solvent dependent and can complicate the assignment of signals and coupling constants. For the avoidance of doubt, such split or broadened signals have been assigned a chemical shift range as observed and have been designated as multiplets.

Purity was assessed using one or more of the following:
UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.05% formic acid or 0.025% ammonia. Mass spectra were recorded with a Waters SQD single quadrupole mass spectrometer using atmospheric pressure ionisation.

Perkin Elmer 200 series system equipped with Agilent Poroshell 120 column (SB-C18, 4.6 mm id×30 mm, 2.7 μm) operated at 20° C. Mobile phases consisted of acetonitrile and water, both containing 0.1% v/v formic acid. Mass spectra were recorded with a PE SCIEX API 2000 MS/MS mass spectrometer. The system was controlled by Analyst software (version 1.5.1).

Compounds were purified using normal phase chromatography on silica, using Biotage or Isolute KP-Sil cartridges or Kinesis Telos Silica cartridges, or on basic silica, using Biotage or Isolute KP-NH cartridges, or by reverse phase chromatographic methods, using Biotage or Isolute KP-C18-HS cartridges or by SCX-2 catch-release cartridges, or by Preparative HPLC, or by Supercritical Fluid Chromatography (SFC).

Preparative HPLC was performed using one or more of the following:
  Agilent Technologies 1100 Series system or a Waters autopurification LC/MS system typically using Waters 19 mm id×100 mm long C18 columns such as XBridge or SunFire 5 μm materials at room temperature.
  Gilson HPLC system using Waters XBridge Column (C18, 5 μm, 19 mm id×250 mm), controlled by UniPoint software (version 2.10)
  Waters autopurification LC/MS system using Varian Column (C18, 5 μm, 21.2 mm id×150 mm), controlled by MassLynx software (version 4.0 SP4)

Mobile phases typically consisted of acetonitrile or methanol mixed with water containing either 0.1% formic acid or 0.1% ammonia, unless stated otherwise.

Room temperature in the following schemes means the temperature ranging from 20° C. to 25° C.

The following abbreviations are used in the Examples:
ACE-Cl α-chloroethyl chloroformate
ACN acetonitrile
aq. aqueous
BOC tert-butoxycarbonyl
BOC- di-tert-butyl dicarbonate anhydride
CHCl$_3$ chloroform
Cs$_2$CO$_3$ caesium carbonate
CV column volumes
DCE 1,2-dichloroethane
DCM dichloromethane
DEA diethyl amine
DMAP 4-(dimethylamino)pyridine
DMSO dimethyl sulfoxide
DMF dimethylformamide
dppf 1,1'-bis(diphenylphosphino)ferrocene
e.e. enantiomeric excess
EDC 1-ethyl-3-(3-dimethylaminopropyl)carbodiimide
Et$_3$N triethylamine
EtOAc ethyl acetate
EtOH ethanol
g grams
HOAt 1-hydroxy-7-azabenzotriazole
HOBt hydroxybenzotriazole
HPLC high pressure liquid chromatography
IPA isopropyl alcohol
LCMS liquid chromatographic mass spectrometry
LiOH lithium hydroxide
LiHMDS lithium bis(trimethylsilyl)amide
MeCN acetonitrile
MeOH methanol
mg milligrams
mins minutes
mL millilitres
mmol millimoles
MS mass spectrometry
MTBE tert-butyl methyl ether
Na$_2$SO$_4$ sodium sulphate
NH$_3$ ammonia
NMP 1-methyl-2-pyrrolidone
NMR nuclear magnetic resonance
PG protecting group
ppm parts per milion
Rt retention time
sat. saturated
SFC supercritical fluid chromatography
T3P propylphosphonic anhydride
TEA triethylamine
THF tetrahydrofuran

1. INTERMEDIATES

Intermediate 1a1

3-(2-Fluorophenyl)piperidine hydrochloride

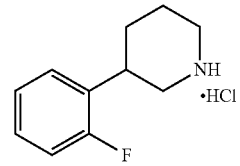 [SMILES: Fc1ccccc1C1CCCNC1 ; Cl]

Step (i) Tetrakis(triphenylphosphine) palladium (0) (50 mg, 0.04 mmol) was added to a degassed solution of 3-iodopyridine (300 mg, 1.46 mmol) and (2-fluorophenyl)boronic acid (225 mg, 1.61 mmol) in toluene (7 mL) and EtOH (2 mL) under nitrogen. Sodium carbonate (465 mg, 4.39 mmol) was added and the reaction was heated in the microwave at 100° C. for 60 minutes. The reaction mixture was passed through a Celite cartridge, washing with EtOAc (10 mL), the residue was purified by column chromatography eluting with petroleum ether/ethyl acetate 0-100% gradient. The desired fractions were combined and concentrated in vacuo to afford 3-(2-fluorophenyl)pyridine (160 mg, 0.92 mmol, 63%).

MS ES$^+$: 173

Step (ii) 3-(2-fluorophenyl)pyridine (160 mg, 0.92 mmol) was dissolved in anhydrous EtOH (50 mL) and hydrogen chloride (0.29 mL, 3.51 mmol) was added. The reaction mixture was evacuated and filled with nitrogen three times before platinum (IV) oxide (14 mg, 0.06 mmol) was added. The reaction was evacuated and filled with hydrogen from a balloon, then stirred at room temperature for 18 hours. The reaction mixture was filtered over Celite, washing with EtOH (10 mL) and then concentrated in vacuo to give 3-(2-fluorophenyl)piperidine hydrochloride (120 mg, 0.67 mmol, 72%)

MS ES$^+$: 180

Intermediate 1a2

3-(2,4-Dichlorophenyl)piperidine hydrochloride

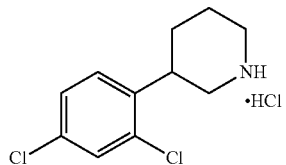 [SMILES: Clc1ccc(C2CCCNC2)c(Cl)c1 ; Cl]

Prepared as described for 3-(2-fluorophenyl)piperidine hydrochloride (Intermediate 1a1) using 3-iodopyridine and (2,4-dichlorophenyl)boronic acid.

MS ES$^+$: 230

Intermediate 1a3

3-(4-Chlorophenyl)piperidine hydrochloride

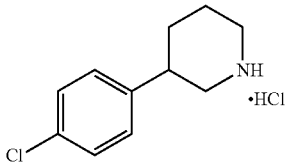 [SMILES: Clc1ccc(C2CCCNC2)cc1 ; Cl]

Prepared as described for 3-(2-fluorophenyl)piperidine hydrochloride (Intermediate 1a1) using 3-iodopyridine and (4-chlorophenyl)boronic acid.

MS ES$^+$: 196

Intermediate 1a3A

(3S)-3-(4-Chlorophenyl)piperidine

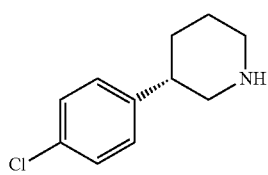 [SMILES: Clc1ccc([C@@H]2CCCNC2)cc1]

Chiral resolution of racemic 3-(4-chlorophenyl)piperidine (Chembridge 4004245; CAS 55989-13-4) using chiral SFC (Chiralpak OD-H column, isocratic, EtOH, 0.2% DEA) yielded (3S)-3-(4-Chlorophenyl)piperidine as the first eluting peak. Solvents removed in vacuo to give (3S)-3-(4-Chlorophenyl)piperidine as a solid.

MS ES$^+$: 196

Chiral HPLC (Chiralpak AD column, isocratic EtOH 0.2% DEA) Rt=2.31 mins

Intermediate 1a3B

(3R)-3-(4-Chlorophenyl)piperidine

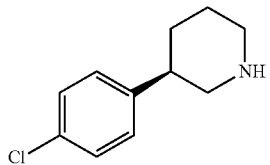 [SMILES: Clc1ccc([C@H]2CCCNC2)cc1]

Chiral resolution of racemic 3-(4-chlorophenyl)piperidine (Chembridge 4004245; CAS 55989-13-4) using chiral SFC (Chiralpak OD-H column, isocratic, EtOH, 0.2% DEA) yielded (3R)-3-(4-chlorophenyl)piperidine as the second eluting peak. Solvents removed in vacuo to give (3R)-3-(4-chlorophenyl)piperidine as a solid.

MS ES$^+$: 196

Chiral HPLC (Chiralpak AD column, isocratic EtOH 0.2% DEA) Rt=5.75 mins

Intermediate 1a4

Lithium(1+) ion 2-cyclopropylpyridine-4-carboxylate

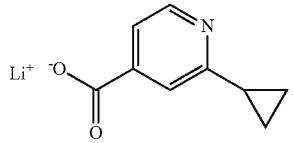

Step (i) A solution of methyl 2-bromoisonicotinate (500 mg, 2,314 mmol), potassium cyclopropyltrifluoroborate (685 mg, 4.63 mmol) and Cs$_2$CO$_3$ (2262 mg, 6.94 mmol) in THF (0.15 mL) and water (1.5 mL) was degassed by evacuating and flushing with N$_2$. PdCl$_2$(dppf)-CH$_2$Cl$_2$ adduct (189 mg, 0.231 mmol) was added and the reaction was stirred at 85° C. for 18 hours. The reaction was diluted with EtOAc and filtered through celite. The eluent was concentrated under vacuum. The crude product was purified by column chromatography on silica eluting with petroleum ether/ethyl acetate from 100/0 to 80/20 to yield methyl 2-cyclopropylpyridine-4-carboxylate as a colourless oil (170 mg, 0.959 mmol, 42% yield).

$^1$H NMR (400 MHz, DCM-d$_2$) δ ppm 0.98-1.10 (m, 4 H) 2.05-2.20 (m, 1 H) 3.95 (s, 3 H) 7.52-7.65 (m, 1 H) 7.72 (s, 1 H) 8.47-8.65 (m, 1 H)

MS ES$^+$: 178.

Step (ii) Methyl 2-cyclopropylpyridine-4-carboxylate (170 mg, 0.959 mmol) was dissolved in a mixture of THF (9 mL) and water (3 mL) and LiOH (45.98 mg, 1.920 mmol) was added. The mixture was stirred at ambient temperature for 19 hours. The reaction mixture was concentrated under vacuum used crude in the next step.

MS ES$^+$: 164.

Intermediate 1a5

3-(4-Chloro-2-methylphenyl)piperidine hydrochloride

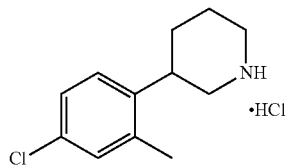

Prepared as described for 3-(2-fluorophenyl)piperidine hydrochloride (Intermediate 1a1) from 3-iodopyridine and (4-chloro-2-methylphenyl)boronic acid.
MS ES+: 210

Intermediate 1a6

3-[4-Chloro-2-(trifluoromethyl)phenyl]piperidine hydrochloride

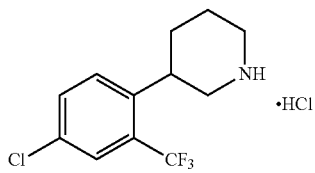 [SMILES: FC(F)(F)c1cc(Cl)ccc1C1CCCNC1 ; Cl]

Prepared as described for 3-(2-fluorophenyl)piperidine hydrochloride (Intermediate 1a1) from 3-iodopyridine and (4-chloro-2-(trifluoromethyl)phenyl)boronic acid. The product was optionally free based by loading on to a cation exchange cartridge (SCX-2) and eluting with EtOAc/[2M NH$_3$ in MeOH].
MS ES+: 264

Intermediates 1a6A and 1a6B

3-[4-Chloro-2-(trifluoromethyl)phenyl]piperidine hydrochloride (enantiomers)

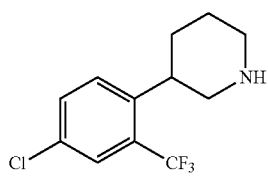

Chiral resolution of racemic 3-[4-Chloro-2-(trifluoromethyl)phenyl]piperidine hydrochloride (Intermediate 1a6) using chiral SFC (Chiralcel-OD, 250×20 mm, 5 um column, eluting with heptane/IPA in a 80/20 ratio. Diethylamine (0.2%) was used as a modifier. The first eluting peak was assigned Intermediate 1a6A and the second eluting peak was assigned Intermediate 1a6B. The solvents were removed in vacuo to give the enantiomers of 3-[4-Chloro-2-(trifluoromethyl)phenyl]piperidine hydrochloride as solids.
MS ES+: 264

Intermediate 1a7

4-{[3-(4-Chlorophenyl)piperidin-1-yl]carbonyl}-2-fluoropyridine

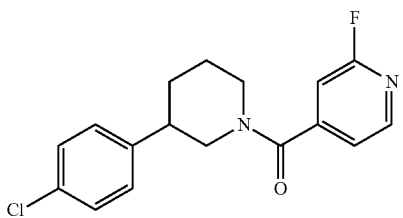 [SMILES: O=C(c1ccnc(F)c1)N1CCCC(c2ccc(Cl)cc2)C1]

3-(4-Chlorophenyl)piperidine (0.1 g, 0.511 mmol) was added to a suspension of EDC (0.122 g, 0.639 mmol), HOBt (0.088 g, 0.572 mmol). TEA (0.249 mL, 1.789 mmol) and 2-fluoroisonicotinic acid (0.079 g, 0.562 mmol) in DCM (2 mL). The reaction was stirred at room temperature for 18 hours. The crude reaction mixture was purified by column chromatography on silica, eluting with 0-80% ethyl acetate/petrol, to afford 4-{[3-(4-chlorophenyl)piperidin-1-yl]carbonyl}-2-fluoropyridine (149 mg, 0.467 mmol, 91% yield) as a solid.
MS ES+: 319

Intermediate 1a8

2-Fluoro-4-{[3-(4-methylphenyl)piperidin-1-yl]carbonyl}pyridine

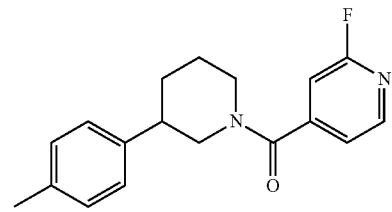 [SMILES: Cc1ccc(C2CCCN(C(=O)c3ccnc(F)c3)C2)cc1]

Prepared as described for 4-{[3-(4-chlorophenyl)piperidin-1-yl]carbonyl}-2-fluoropyridine (Intermediate 1a7) from 2-fluoroisonicotinic acid and 3-(4-methylphenyl)piperidine hydrochloride.
MS ES+: 299

Intermediate 1a9

2-Fluoro-4-{([3-(2-methylphenyl)piperidin-1-yl]carbonyl}pyridine

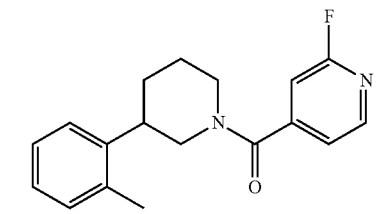 [SMILES: Cc1ccccc1C1CCCN(C(=O)c2ccnc(F)c2)C1]

Prepared as described for 4-{[3-(4-chlorophenyl)piperidin-1-yl]carbonyl}-2-fluoropyridine (Intermediate 1a7) from 2-fluoroisonicotinic acid and 3-(2-methylphenyl)piperidine hydrochloride.
MS ES+: 299

Intermediate 1a10

3-(4-Chloro-2-fluorophenyl)piperidine hydrochloride

Prepared as described for 3-(2-fluorophenyl)piperidine hydrochloride (Intermediate 1a1) from 3-iodopyridine and (4-chloro-2-fluorophenyl)boronic acid.
MS ES+: 214

Intermediate 1a11

3-(2-Chloro-4-fluorophenyl)piperidine hydrochloride

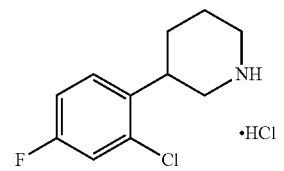 [SMILES: Fc1ccc(C2CCCNC2)c(Cl)c1 ; Cl]

Prepared as described for 3-(2-fluorophenyl)piperidine hydrochloride (Intermediate 1a1) from 3-iodopyridine and (2-chloro-4-fluorophenyl)boronic acid.
MS ES+: 214

Intermediate 1a12

2-Chloro-4-{[3-(4-chlorophenyl)piperidin-1-yl]carbonyl}pyridine

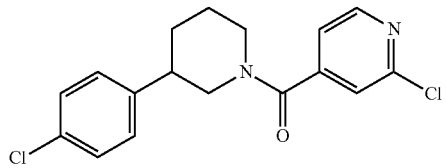 [SMILES: O=C(c1ccnc(Cl)c1)N1CCCC(c2ccc(Cl)cc2)C1]

A solution of propylphosphonic anhydride (50% in EtOAc) (1.5 mL, 2.56 mmol) was added to a solution of 3-(4-chlorophenyl)piperidine (250 mg, 1.27 mmol) (Intermediate 1a3), triethylamine (0.36 mL, 2.56 mmol) and 2-chloroisonicotinic acid (242 mg, 1.53 mmol) in DCM (5 mL). The reaction was stirred at room temperature for 2 hours. The crude product was purified by column chromatography on basic silica eluting with ethyl acetate/petrol 0-100% to afford 2-chloro-4-{[3-(4-chlorophenyl)piperidin-1-yl]carbonyl}pyridine (413 mg, 1.23 mmol, 96%) as a solid.
MS ES+: 335

Intermediate 1a13

4-{[3-(4-Chloro-2-methylphenyl)piperidin-1-yl]carbonyl}-2-fluoropyridine

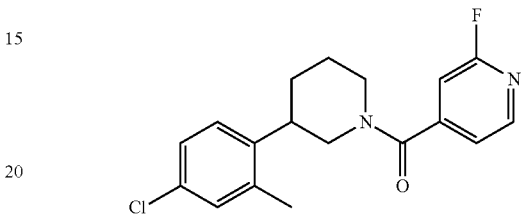

Prepared as described for 2-chloro-4-{[3-(4-chlorophenyl)piperidin-1-yl]carbonyl}pyridine (Intermediate 1a12) using 3-(4-chloro-2-methylphenyl)piperidine hydrochloride (Intermediate 1a5) and 2-fluoroisonicotinic acid.
MS ES+: 333

Intermediate 1a14

3-[4-(Trifluoromethyl)phenyl]piperidine hydrochloride

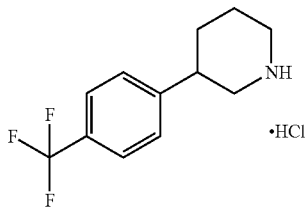 [SMILES: FC(F)(F)c1ccc(C2CCCNC2)cc1 ; Cl]

Step (i) To a solution of 3-iodopyridine (4.00 g, 19.50 mmol), 4-(trifluoromethyl)phenylboronic acid (4.07 g, 21.50 mmol) in toluene (100 mL) and EtOH (25 mL) under nitrogen, was added 2 M aqueous sodium carbonate (29 mL, 58.50 mmol). The solution was degassed, tetrakis(triphenylphosphine) palladium (0) (750 mg, 0.65 mmol) was added and the reaction was heated at 100° C. for 3 hours. The mixture was allowed to cool to room temperature, diluted with EtOAc (50 mL), washed with water (2×50 mL), saturated brine (1×50 mL), dried (Na$_2$SO$_4$) and concentrated in vacuo. The crude product was purified by column chromatography on silica eluting with DCM to afford 3-(4-(trifluoromethyl)phenyl)pyridine (3.78 g, 87%) as a solid.
$^1$H NMR (400 MHz, CHCl$_3$-d) δ ppm 7.42-7.47 (m, 1 H) 7.72 (d, J=8.86, 4 H) 7.91-7.95 (m, 1 H) 8.67-8.66 (m, 1 H) 8.87 (s, 1 H)
MS ES+: 224

Step (ii) Platinum (IV) oxide (0.38 g, 1.69 mmol) was added to a degassed solution of 3-(4-(trifluoromethyl)phenyl)pyridine (3.78 g, 16.90 mmol) and hydrochloric acid (5 mL) in EtOH (132 mL) under nitrogen. The reaction mixture was evacuated and the autoclave filled with hydrogen at 5 bar pressure for 72 hours. The reaction mixture was filtered through a bed of Celite and concentrated in vacuo. This yielded 3-[4-(trifluoromethyl)phenyl]piperidine hydrochloride (4.21 g, 94% yield) as a solid.

MS ES⁺: 230

Intermediate 1a15

3-[2-(Trifluoromethyl)phenyl]piperidine hydrochloride

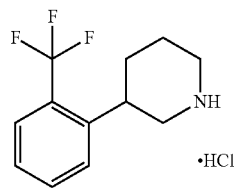

Step (i) To a solution of 3-iodopyridine (0.4.00 g, 19.50 mmol), 2-(trifluoromethyl)phenylboronic acid (4.07 g, 21.50 mmol) in toluene (100 mL) and EtOH (25 mL) under nitrogen was added 2 M aqueous sodium carbonate (29 mL, 58.50 mmol). The solution was degassed, tetrakis(triphenylphosphine) palladium (0) (750 mg, 0.65 mmol) was added and the reaction was heated at 100° C. for 8 hours. The mixture was allowed to cool to room temperature, diluted with EtOAc (50 mL), washed with water (2×50 mL), saturated brine (1×50 mL), dried (Na₂SO₄) and concentrated in vacuo. The crude product was purified by column chromatography on silica eluting with DCM to afford 3-[2-(trifluoromethyl)phenyl]pyridine (3.08 g, 71%) as an oil.

MS ES⁺: 224

Step (ii) Platinum (IV) oxide (310 mg, 1.38 mmol) was added to a degassed solution of 3-[2-(trifluoromethyl)phenyl]pyridine (3.08 g, 13.80 mmol) in EtOH (108 mL) and hydrogen chloride (4 mL) under nitrogen. The reaction mixture was evacuated and the autoclave filled with hydrogen at 5 bar pressure for 72 hours. The reaction mixture was filtered through a bed of Celite and concentrated in vacuo. This yielded 3-[2-(trifluoromethyl)phenyl]piperidine hydrochloride (3.16 g, 13.8 mmol, 100%) as a solid.

¹H NMR (400 MHz, DMSO-d₆) δ ppm 1.79-1.91 (m, 4 H) 2.95-2.98 (m, 1 H) 3.16-3.47 (m, 4 H) 7.46-7.50 (m, 1 H) 7.68-7.75 (m, 3 H) 9.00 (s, 1 H) 9.32 (s, 1 H)

MS ES⁺: 230

Intermediate 1a16

3-(2-Chlorophenyl)piperidine hydrochloride

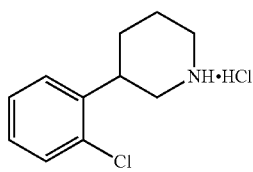

Prepared as described for 3-(2-fluorophenyl)piperidine hydrochloride (Intermediate 1a1) from 3-iodopyridine and (2-chlorophenyl)boronic acid.

MS ES⁺: 196

Intermediate 1a17

3-(4-Methoxyphenyl)piperidine hydrochloride

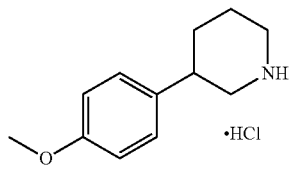

Step (i) To a solution of 3-iodopyridine (4.00 g, 19.50 mmol), 4-methoxy benzeneboronic acid (3.26 g, 21.50 mmol) in toluene (100 mL) and EtOH (25 mL) under nitrogen, was added 2 M aqueous sodium carbonate (29 mL, 58.50 mmol). The solution was degassed, tetrakis(triphenylphosphine) palladium (0) (750 mg, 0.65 mmol) was added and the reaction was heated at 100° C. for 3 hours. The mixture was allowed to cool to room temperature, diluted with EtOAc (50 mL), washed with water (2×50 mL), saturated brine (1×50 mL), dried (Na₂SO₄) and concentrated in vacuo. The crude product was purified by column chromatography on silica eluting with DCM to afford 3-(4-methoxyphenyl)pyridine (2.43 g, 67%) as an oil.

¹H NMR (400 MHz, CHCl₃-d) δ ppm 3.84 (s, 3 H) 6.98-7.02 (m, 2 H) 7.32-7.35 (m, 1 H) 7.49-7.53 (m, 2 H) 7.81-7.84 (m, 1 H) 8.54 (d, J=4.09, 1 H) 8.81 (s, 1 H)

MS ES⁺: 186

Step (ii) Platinum (IV) oxide (0.21 g, 0.93 mmol) was added to a degassed solution of 3-(4-methoxyphenyl)pyridine (1.73 g, 9.34 mmol) in EtOH (74 mL) and hydrogen chloride (3 mL) under nitrogen. The reaction mixture was evacuated and the autoclave filled with hydrogen at 10 bar pressure for 96 hours. The reaction mixture was filtered through a bed of Celite and concentrated in vacuo. This yielded 3-(4-methoxyphenyl)piperidine hydrochloride, as an oil, used without further purification.

¹H NMR (400 MHz, DMSO-d₆) δ ppm 1.41-1.86 (m, 5 H) 2.67-2.96 (m, 4 H) 3.71 (s, 3 H) 6.91 (d, J=8.45, 2 H) 7.20 (d, J=8.45, 2H)

MS ES⁺: 192

Intermediate 1a18

3-(2-Methoxyphenyl)piperidine

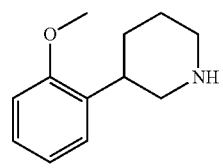

Step (i) To a solution of 3-iodopyridine (4.00 g, 19.5 mmol), 2-methoxy benzeneboronic acid (3.26 g, 21.5 mmol) in toluene (100 mL) and EtOH (25 mL), under nitrogen, was added 2 M aqueous sodium carbonate (29.3 mL, 58.5 mmol). The solution was degassed, tetrakis(triphenylphosphine) palladium (0) (0.75 g, 0.65 mmol) was added and the reaction was heated at 100° C. for 8 hours. The mixture was allowed to cool to ambient temperature, diluted with ethyl acetate (50 mL), washed with water (2×50 mL), saturated brine (0.1×50 mL), dried (Na$_2$SO$_4$) and concentrated in vacuo. The crude product was purified by column chromatography on silica eluting with DCM to afford 3-(2-methoxyphenyl)pyridine (1.65 g, 46%) as an oil.

$^1$H NMR (400 MHz, CHCl$_3$-d) δ ppm 3.82 (s, 3 H) 7.00-7.09 (m, 2 H) 7.31-7.41 (m, 3 H) 7.89-7.91 (m, 1 H) 8.57 (d, J=4.36, 1 H) 8.79 (s, 1 H)

MS ES$^+$: 186

Step (ii) Platinum (IV) oxide (0.20 g, 0.89 mmol) was added to a degassed solution of 3-(2-methoxyphenyl)pyridine (1.65 g, 8.91 mmol) in EtOH (70 mL) and hydrogen chloride (2.85 mL) under nitrogen. The reaction mixture was evacuated and the autoclave filled with hydrogen at 10 bar pressure for 120 hours. The reaction mixture was filtered through a bed of Celite and concentrated in vacuo. Water (50 mL) was added and the solution was adjusted to pH 8 with 1M NaOH solution. This was then taken up in EtOH, filtered and concentrated in vacuo. This yielded 3-(2-methoxyphenyl)piperidine (quantitative yield) as a solid, which was used without further purification.

$^1$H NMR (400 MHz, DMSO-d$_6$) δ ppm 1.42-1.78 (m, 5 H) 2.33-2.54 (m, 2 H) 2.89-3.03 (m, 2 H) 3.78 (s, 3 H) 6.87-6.96 (m, 2 H) 7.13-7.24 (m, 2H) 8.54 (s, 1H)

MS ES$^+$: 192

Intermediate 1a19

3-[2-(Trifluoromethoxy)phenyl]piperidine hydrochloride

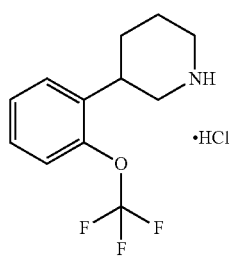 [SMILES: FC(F)(F)Oc1ccccc1C1CCCNC1 ; Cl]

Step (i) Prepared as described for 3-[2-(trifluoromethyl)phenyl]pyridine (Intermediate 1a15, step (i)) from (2-(trifluoromethoxy)phenyl)boronic acid and 3-iodopyridine.

MS ES$^+$: 240

Step (ii) Prepared as described for 3-[2-(trifluoromethyl)phenyl]piperidine hydrochloride (Intermediate 1a15, step (ii)) from 3-[2-(trifluoromethoxy)phenyl]pyridine.

MS ES$^+$: 246

Intermediate 1a20

3-(4-Chloro-2-ethoxyphenyl)piperidine hydrochloride

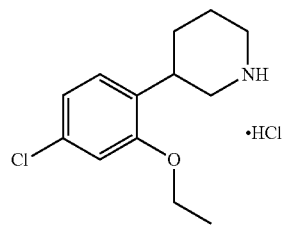 [SMILES: CCOc1cc(Cl)ccc1C1CCCNC1 ; Cl]

Step (i) Prepared as described for 3-[2-(trifluoromethyl)phenyl]pyridine (Intermediate 1a15, step (i)) from (4-chloro-2-ethoxyphenyl)boronic acid and 3-iodopyridine.

MS ES$^+$: 234

Step (ii) Prepared as described for 3-[2-(trifluoromethyl)phenyl]piperidine hydrochloride (Intermediate 1a15, step (ii)) from 3-(4-chloro-2-ethoxyphenyl)pyridine

MS ES$^+$: 240

Intermediate 1a21

3-[4-Methoxy-2-(trifluoromethyl)phenyl]piperidine hydrochloride

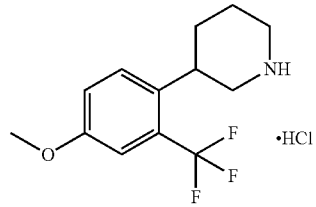 [SMILES: COc1ccc(C2CCCNC2)c(C(F)(F)F)c1 ; Cl]

Step (i) Prepared as described for 3-(2-fluorophenyl)piperidine hydrochloride (Intermediate 1a1, step (i)) except using 1,4-dioxane/water (5:1) as solvent, 120° C. microwave irradiation and 3-iodopyridine and (4-methoxy-2-(trifluoromethyl)phenyl)boronic acid.

MS ES$^+$: 254

Step (ii) Prepared as described for 3-(2-fluorophenyl)piperidine hydrochloride (Intermediate 1a1, step (ii)) from 3-[4-methoxy-2-(trifluoromethyl)phenyl]pyridine.

MS ES$^+$: 260

Intermediate 1a22

3-(4-Methoxy-2-methylphenyl)piperidine

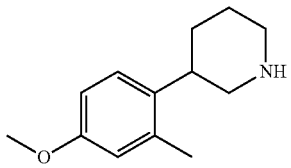

Step (i) A microwave vial was charged with 3-iodopyridine (561 mg, 2.74 mmol), (4-methoxy-2-methylphenyl)boronic acid (500 mg, 3.01 mmol), sodium carbonate (1135 mg, 10.71 mmol) and tetrakis(triphenylphosphine) palladium (0) (104 mg, 0.090 mmol). Dioxane (5 mL) and water (0.1 mL) were added and the vial was sealed, purged with nitrogen and irradiated in a microwave at 100° C. for 20 minutes and then at 120° C. for 60 minutes. The reaction mixture was diluted in EtOAc (30 mL) and washed with water (2×10 mL), dried over MgSO$_4$, filtered, and reduced in vacuo. The crude product was purified by column chromatography on silica, eluting with 15-100% ethyl acetate/petrol, to afford 3-(4-methoxy-2-methylphenyl)pyridine (525 mg, 2.63 mmol, 96% yield) as an oil.

MS ES$^+$: 200

Step (ii) A solution of 3-(4-methoxy-2-methylphenyl)pyridine (0.415 g, 2.083 mmol) and HCl (0.234 mL, 7.71 mmol) in ethanol/acetic acid (9:1; 20 mL) was eluted through a hydrogen flow reactor (Thales H-cube) fitted with a PtO$_2$ catalyst cartridge on continual cycling mode at 100 bar, 100° C. Reaction very slow so switched to 5% Rh/Al$_2$O$_3$ and initiated cycling flow at 2 mL/min, 70° C. and 70 bar. After 3 hours eluant was collected and the solvent removed in vacuo. The crude product was dissolved in ethanol (5 mL) and loaded onto a 20 g SCX-2 cation exchange cartridge, washed with EtOH (50 mL) and eluted off with 2M NH$_3$ in MeOH solution (50 mL). Solvent removed in vacuo to give 3-(4-methoxy-2-methylphenyl)piperidine (0.364 g, 1.773 mmol, 85% yield) as an oil.

MS ES$^+$: 206

Intermediate 1a23

3-[2-(Difluoromethoxy)phenyl]piperidine hydrochloride

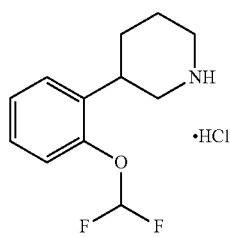 [SMILES: FC(F)Oc1ccccc1C1CCCNC1 ; Cl]

Prepared as described for 3-(2-fluorophenyl)piperidine hydrochloride (Intermediate 1a1) using 3-iodopyridine and (2-(difluoromethoxy)phenyl)boronic acid.

MS ES$^+$: 228

Intermediate 1a24

2-(Piperidin-3-yl)benzonitrile hydrochloride

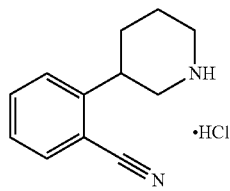 [SMILES: N#Cc1ccccc1C1CCCNC1 ; Cl]

Step (i) To a sealed tube containing 3-bromopyridine (2.27 g, 14.4 mmol) dissolved in DMF (60 mL) was added (2-carbamoylphenyl)boronic acid (5.0 g, 30.3 mmol) and potassium carbonate (3.01 g, 27.6 mmol). The solution was degassed and 1,1-bis(diphenylphosphino)ferrocenepalladium (II) dichloride (0.902 g, 1.52 mmol) was added, the tube was sealed and heated to 125° C. overnight. The reaction mixture was cooled to ambient temperature and solvent removed in vacuo. The residue was re-dissolved in 1N aqueous hydrochloric acid (200 mL) and washed with EtOAc (100 mL). The pH was adjusted to pH8 with 1N NaOH and extracted with DCM (3×100 mL). The combined organic layers were dried (Na$_2$SO$_4$) filtered and concentrated in vacuo. The solid was triturated with ether to give 2-(pyridin-3-yl)benzamide as a solid (2.07 g, 73%).

MS ES$^+$: 199

Step (ii) Platinum (IV) oxide (0.237 g, 1.04 mmol) was added to a degassed solution of 2-(pyridin-3-yl)benzamide (2000 mg, 10.100 mmol) in EtOH (85 mL) and hydrogen chloride (3.33 mL) under nitrogen. The reaction mixture was evacuated and the autoclave filled with hydrogen at 10 bar pressure for 48 hours at 55° C. The reaction mixture was filtered through a bed of Celite and concentrated in vacuo to give 2-(piperidin-3-yl)benzamide hydrochloride as a solid (2.50 g, 100%).

MS ES$^+$: 205

Step (iii) To a suspension of 2-(piperidin-3-yl)benzamide hydrochloride (2.50 g, 10.38 mmol) in THF (25 mL) was added triethylamine (2420 mg, 23.88 mmol) followed by the drop wise addition of trifluoroacetic acid anhydride (1.59 mL, 11.42 mmol). The reaction mixture was stirred at room temperature for 18 hours. The reaction was concentrated in vacuo, DCM (100 mL) was added and washed with saturated aqueous sodium hydrogen carbonate solution (3×100 mL), dried (Na$_2$SO$_4$) and concentrated in vacuo. Purification was carried out via silica column chromatography solvent system: 0-100% DCM to give 2-[1-(trifluoroacetyl)piperidin-3-yl]benzonitrile (1.90 g, 65%) as an oil. The material was carried through to the next step without further characterisation.

Step (iv) To a solution of 2-[1-(trifluoroacetyl)piperidin-3-yl]benzonitrile (1.9 g, 6.70 mmol) in EtOH (47 mL) was added a solution of potassium carbonate (5.56 g, 40.2 mmol) in water (0.16 mL) and the resulting mixture was heated at reflux overnight. The reaction was concentrated in vacuo, water (100 mL) was added and extracted with DCM (2×100 mL), dried (Na$_2$SO$_4$) and concentrated in vacuo to give 2-(piperidin-3-yl)benzoic acid (1.9 g) as a solid.

MS ES$^+$: 206

Step (v) To a solution of 2-(piperidin-3-yl)benzoic acid (1.9 g, 9.25 mmol), triethylamine (2.57 mL, 18.5 mmol) in DCM (50 mL) was added di-tert-butyl dicarbonate (2.12 g, 9.71 mmol). The mixture was stirred overnight at room temperature. Water (50 mL) was added and extracted with DCM (3×50 mL), dried (Na$_2$SO$_4$) and concentrated in vacuo. Purification was carried out via silica column chromatography solvent system: 0-5% MeOH/DCM to give 2-{1-[(tert-butoxy)carbonyl]piperidin-3-yl}benzoic acid (0.7 g, 25%) as a solid.

MS ES$^+$: 306

Step (vi) To a solution of 2-{1-[(tert-butoxy)carbonyl]piperidin-3-yl}benzoic acid (0.7 g, 2.29 mmol) in THF (15 mL) was added 1,1-carbonyl diimidazole (0.74 g, 4.58 mmol) and the reaction mixture was stirred at room temperature overnight. Ammonia (33% in water, 2.19 mL, 114.6 mmol) was added in THF (7 mL) and stirred for 3 hours. The reaction was concentrated in vacuo, water was added (25 mL) and extracted with EtOAc (3×25 mL), dried over Na₂SO₄ and concentrated in vacuo to give tert-butyl 3-(2-carbamoylphenyl)piperidine-1-carboxylate (0.110 g, 100%) as a solid.

MS ES⁺: 305

Step (vii) To a suspension of tert-butyl 3-(2-carbamoylphenyl)piperidine-1-carboxylate (0.100 g, 0.328 mmol) in THF (1 mL) was added triethylamine (0.0.076 g, 0.105 mL, 0.755 mmol) followed by the drop wise addition of trifluoroacetic acid anhydride (0.076 g, 0.050 mL, 0.361 mmol). The reaction mixture was stirred at room temperature for 18 hours. The reaction mixture was concentrated in vacuo and DCM (20 mL) was added, washed with saturated sodium hydrogen carbonate (3×10 mL), dried Na₂SO₄ and concentrated in vacuo to give tert-butyl 3-(2-cyanophenyl)piperidine-1-carboxylate (0.08 g, 85%) as a solid.

MS ES⁺: 287

Step (viii) tert-Butyl 3-(2-cyanophenyl)piperidine-1-carboxylate (0.08 g, 0.279 mmol) was dissolved in 1,4-dioxane (0.5 mL) and 4M hydrogen chloride in 1,4-dioxane (1 mL) was added. The reaction mixture was stirred at room temperature overnight. The reaction mixture was concentrated in vacuo to give 2-(piperidin-3-yl)benzonitrile hydrochloride (0.062 g, 100%) as a solid.

MS ES⁺: 187

Intermediate 1a25

3-(4-Chloro-2,6-dimethylphenyl)piperidine hydrochloride

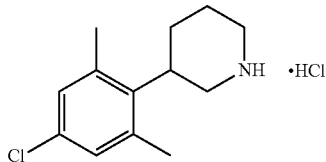

Prepared as described for 3-(2-fluorophenyl)piperidine hydrochloride (Intermediate 1a1) using 3-iodopyridine and (4-chloro-2,6-dimethylphenyl)boronic acid.

MS ES⁺: 224

Intermediate 1b1

6-(Dimethylamino)pyridazine-4-carboxylic acid

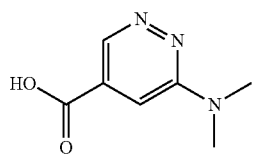

Step (i) Methyl 6-chloropyridazine-4-carboxylate (406 mg, 2.35 mmol) was added to a solution of dimethylamine hydrochloride (188 mg, 2.3 mmol) and triethylamine (0.737 mL, 5.29 mmol) in THF (1.5 mL). The reaction was sealed and heated to 90° C. for 18 hours. The reaction was allowed to cool to room temperate. The mixture was partitioned between ethyl acetate and saturated sodium bicarbonate. The phases were separated and the aqueous phase was extracted with ethyl acetate (3×10 mL). The combined organics were washed with saturated brine (1×10 mL), dried over magnesium sulfate and concentrated in vacuo to give a solid. The crude product was purified by column chromatography on basic silica, eluting with 10-50% ethylacetate/petrol to afford methyl 6-(dimethylamino)pyridazine-4-carboxylate (182 mg, 1.004 mmol, 44% yield) as a solid.

MS ES⁺: 182

Step (ii) A solution of 1M lithium hydroxide (1.142 mL, 1.142 mmol) was added to a solution of methyl 6-(dimethylamino)pyridazine-4-carboxylate (0.18 g, 0.993 mmol) in THF (2 mL) and MeOH (0.500 mL). The reaction was stirred at room temperature for 15 minutes. The reaction was concentrated in vacuo, diluted with water (1.25 mL) and THF (1 mL) and acidified to pH 2-3 with a 10% aqueous hydrogen chloride solution. The reaction mixture was reduced in vacuo to give the title compound which was carried through without further purification.

MS ES⁺: 166

Intermediate 1b2

6-Chloropyridazine-4-carboxylic acid

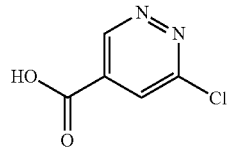

To a stirred solution of methyl 6-chloropyridazine-4-carboxylate (5.05 g, 29.3 mmol) in THF (10 mL)/Water (20 mL) was added lithium hydroxide (1.402 g, 58.5 mmol). After 90 minutes the reaction mixture was acidified to pH 1-2 with conc. HCl (11.8M, 5 mL) and concentrated in vacuo to remove the THF component. Resultant precipitate stirred in predominantly aqueous medium at ambient temperature/pressure for about 30 minutes and was then filtered through a sinter under vacuum. The solid was dried in a vacuum oven to give 6-chloropyridazine-4-carboxylic acid (3.685 g, 23.24 mmol, 79% yield) as a solid.

MS ES⁺: 159

Intermediate 1b3

3-[2-Methoxy-4-(trifluoromethyl)phenyl]piperidine hydrochloride

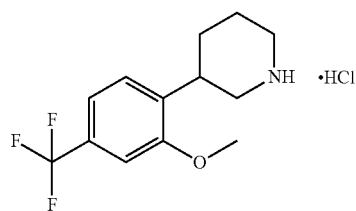 [SMILES: COc1cc(C(F)(F)F)ccc1C1CCCNC1 ; Cl]

Prepared as described for 3-(2-fluorophenyl)piperidine hydrochloride (Intermediate 1a1) using 3-iodopyridine and (2-methoxy-4-(trifluoromethyl)phenyl)boronic acid.

MS ES⁺: 260

Intermediate 2a1

3-(4-Chloro-2-methylphenyl)-1-[(1-methyl-5-nitro-1H-pyrazol-4-yl)carbonyl]piperidine

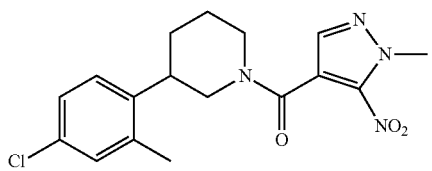 [SMILES: Cc1cc(Cl)ccc1C1CCCN(C(=O)c2cnn(C)c2[N+](=O)[O-])C1]

Prepared as described for 3-chloro-5-{3-[2-methoxy-4-(trifluoromethyl)phenyl]piperidin-1-yl}carbonyl)pyridazine (Intermediate 6) from 3-(4-chloro-2-methylphenyl)piperidine hydrochloride (Intermediate 1a5) and 1-methyl-5-nitro-1H-pyrazole-4-carboxylic acid.

MS ES+: 363

Intermediate 2a2 tert-Butyl N-[4-({3-[4-chloro-2-(trifluoromethyl)phenyl]piperidin-1-yl}carbonyl)-1-methyl-1H-pyrazol-3-yl]carbamate

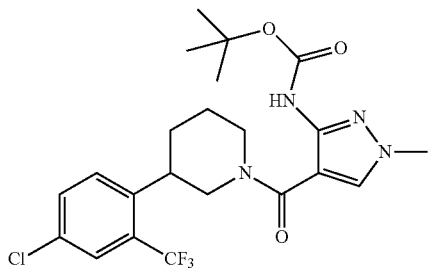 [SMILES: Cn1cc(C(=O)N2CCCC(c3ccc(Cl)cc3C(F)(F)F)C2)c(NC(=O)OC(C)(C)C)n1]

Step (i) Boc-anhydride (3.23 g, 14.78 mmol) was added to a solution of ethyl 3-amino-1-methyl-1H-pyrazole-4-carboxylate (1 g, 5.91 mmol), triethylamine (2.472 mL, 17.73 mmol) and DMAP (0.01 g, 0.082 mmol) in THF (30 mL). The reaction was heated to reflux for 48 hours. Additional Boc-anhydride (3.23 g, 14.78 mmol) was added and the solution heated to reflux overnight. The mixture was partitioned between ethyl acetate and water. The phases were separated and the aqueous phase extracted with ethyl acetate (2×100 mL). The combined organics were washed with brine (100 mL), passed through a phase separator cartridge to remove the aqueous phase and concentrated in vacuo to give ethyl 3-{bis[(tert-butoxy)carbonyl]amino}-1-methyl-1H-pyrazole-4-carboxylate as an oil. It was used in the next step without further purification.

MS ES+: 370

Step (ii) Sodium hydroxide (5.90 mL, 11.80 mmol) was added to a solution of ethyl 3-{bis[(tert-butoxy)carbonyl]amino}-1-methyl-1H-pyrazole-4-carboxylate in EtOH (30 mL) under nitrogen. The reaction was heated to reflux for 4 hours. Additional sodium hydroxide (5.90 mL, 11.80 mmol) was added and the suspension heated to reflux for 2 hours. The suspension was concentrated in vacuo. The solution was acidified with 2M hydrogen chloride then partitioned between ethyl acetate and water. The phases were separated and the aqueous phase extracted with ethyl acetate (3×100 mL). The combined organics were dried (MgSO4) and concentrated in vacuo to give 3-{[(tert-butoxy)carbonyl]amino}-1-methyl-1H-pyrazole-4-carboxylic acid (1.22 g, 5.06 mmol, 86% yield) as a solid.

MS ES−: 240

Step (iii) 3-{[(tert-Butoxy)carbonyl]amino}-1-methyl-1H-pyrazole-4-carboxylic acid (0.805 g, 3.34 mmol) was added to a suspension of 3-[4-chloro-2-(trifluoromethyl)phenyl]piperidine (Intermediate 1a6) (0.8 g, 3.03 mmol), triethylamine (1.269 mL, 9.10 mmol). EDC (0.872 g, 4.55 mmol) and HOAt (0.619 g, 4.55 mmol) in DCM (15 mL). The reaction was stirred at room temperature for 2.5 hours. The mixture was diluted with DCM, washed with saturated NaHCO3 (1×50 mL), 5% citric acid (1×50 mL), water (1×50 mL), the aqueous phase removed using a phase separator cartridge and the organics concentrated in vacuo. The crude product was purified by column chromatography on silica, eluting with 0-100% ethyl acetate/petrol and then increasing to 10% methanol/ethyl acetate to afford tert-butyl N-[4-({3-[4-chloro-2-(trifluoromethyl)phenyl]piperidin-1-yl}carbonyl)-1-methyl-1H-pyrazol-3-yl]carbamate (0.988 g, 2.03 mmol, 66.9% yield) as a solid.

MS ES+: 487

Intermediate 3a1

1-{[2-(Dimethylamino)pyridin-4-yl]carbonyl}piperidin-3-one

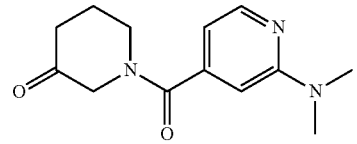 [SMILES: CN(C)c1cc(C(=O)N2CCCC(=O)C2)ccn1]

To a stirred suspension of 2-(dimethylamino)isonicotinic acid hydrochloride (1.5 g, 7.40 mmol) in DCM (25 mL) was added triethylamine (3.30 mL, 23.69 mmol). The reaction mixture became homogeneous. Propylphosphonic anhydride (50% solution in EtOAc) (8.72 mL, 14.80 mmol) was added. After 25 minutes piperidin-3-one hydrochloride (1,204 g, 8.88 mmol) was added in portions over 5 minutes. The reaction mixture was stirred at ambient temperature for 4 hours. The reaction was quenched with saturated sodium bicarbonate (25 mL) and diluted further with water (25 mL). The phases were separated and the aqueous phase was extracted with DCM (25 mL). The combined organics were washed with brine (50 mL), dried over sodium sulphate, filtered and reduced in vacuo. The crude product was purified by reverse phase column chromatography eluting with 0-60% acetonitrile/water containing 0.1% ammonia to afford 1-{[2-(dimethylamino)pyridin-4-yl]carbonyl}-piperidin-3-one (0.505 g, 1.981 mmol, 26.8% yield) as an amber gum.

MS ES+: 248.

Intermediate 3a2

1-{[2-(Dimethylamino)pyridin-4-yl]carbonyl}-1,4,5,6-tetrahydropyridin-3-yl 1,1,2,2,3,3,4,4,4-nonafluorobutane-1-sulfonate

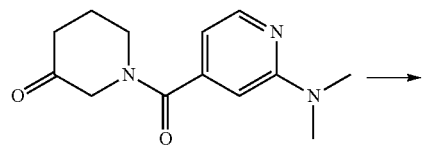

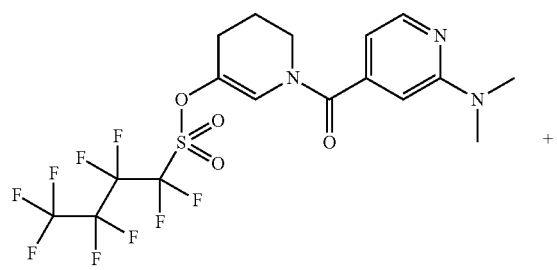

3a2

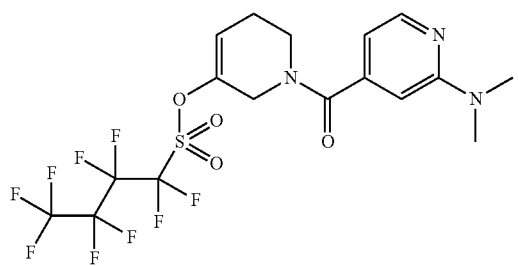

To a stirred solution of lithium bis(trimethylsilyl)amide [1.0M in THF] (10.89 mL, 10.89 mmol) in THF (20 mL) at −78° C. was added a solution of 1-{[2-(dimethylamino)pyridin-4-yl]carbonyl}piperidin-3-one (Intermediate 3a1) (1.92 g, 7.78 mmol) in THF (15 mL) drop wise over 5 minutes under a nitrogen atmosphere, 1,1,2,2,3,3,4,4,4-nonafluorobutane-1-sulfonyl fluoride (2.52 mL, 14.00 mmol) was added. After 1 hour additional 1,1,2,2,3,3,4,4,4-nonafluorobutane-1-sulfonyl fluoride (2.52 mL, 14.00 mmol) was added. After 55 minutes additional 1,1,2,2,3,3,4,4,4-nonafluorobutane-1-sulfonyl fluoride (0.5 mL, 2.78 mmol) was added, then the reaction was removed from the cold bath and allowed to warm to ambient temperature. The solvent was removed in vacuo. The crude product was purified by silica column chromatography (solvent system: 20-80% ethyl acetate/petrol). The first eluting component was isolated and identified as 1-{[2-(dimethylamino)pyridin-4-yl]carbonyl}-1,4,5,6-tetrahydropyridin-3-yl 1,1,2,2,3,3,4,4,4-nonafluorobutane-1-sulfonate (1.268 g, 2.395 mmol, 31%), anoil.

$^1$H NMR (400 MHz, CHCl$_3$-d) δ ppm 1.7-2.0 (m, 2 H), 2.3-2.4 (m, 2 H), 2.95 (s, 6 H), 3.3-3.7 (m, 2 H), 6.35 (m, 2 H), 6.7/7.5 (split signal, m, 1 H), 8.1 (m, 1 H)

MS ES$^+$: 530

The second eluting component was isolated and identified as 1-{[2-(dimethylamino)pyridin-4-yl]carbonyl}-1,2,5,6-tetrahydropyridin-3-yl 1,1,2,2,3,3,4,4,4-nonafluorobutane-1-sulfonate (0.284 g, 0.536 mmol, 7% yield), anoil.

$^1$H NMR (400 MHz, CHCl$_3$-d) δ ppm 2.2-2.5 (m, 2 H), 3.0 (s, 6 H), 3.3-3.8 (m, 2 H), 3.9-4.3 (m, 2 H), 5.9 (m, 1 H), 6.3-6.4 (m, 2 H), 8.1 (m, 1 H)

MS ES$^+$: 530

Intermediate 4

3-Chloro-5-{[3-(4-chloro-2-methylphenyl)piperidin-1-yl]carbonyl}pyridazine

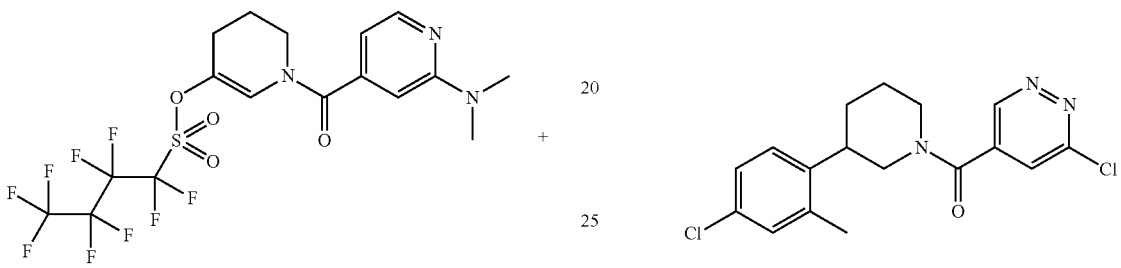

To a stirred suspension of 6-chloropyridazine-4-carboxylic acid (Intermediate 1 b2) (0.1 g, 0.631 mmol) in DCM (2 ml) was added propylphosphonic anhydride (50% solution in EtOAc, 0.446 ml, 0.757 mmol) and triethylamine (0.176 ml, 1,261 mmol). After 15 minutes 3-(4-chloro-2-methylphenyl)piperidine hydrochloride (Intermediate 1a5) (0.155 g, 0.631 mmol) was added. The reaction was stirred at ambient temperature for 5 hours. The reaction mixture was diluted in EtOAc (20 ml), then washed with saturated aqueous NaHCO3 (2×10 ml), HCl (3%; 2×10 ml) then brine (10 ml). The crude product was purified by column chromatography on silica, eluted with 12-100% ethyl acetate/petrol to afford 3-chloro-5-{[3-(4-chloro-2-methylphenyl)piperidin-1-yl]carbonyl}pyridazine (0.114 g, 0.319 mmol, 51% yield) as a colourless gum.

$^1$H NMR (400 MHz, CHCl$_3$-d) δ ppm 1.53-2.09 (m, 4 H) 2.12-2.47 (m, 3 H) 2.67-3.72 (m, 4 H) 4.64-4.93 (m, 1 H) 6.94-7.26 (m, 3 H) 7.41-7.65 (m, 1 H) 9.06-9.23 (m, 1 H)

MS ES$^+$: 350

Intermediate 5

3-Chloro-5-({3-[4-chloro-2-(trifluoromethyl)phenyl]piperidin-1-yl}carbonyl)pyridazine

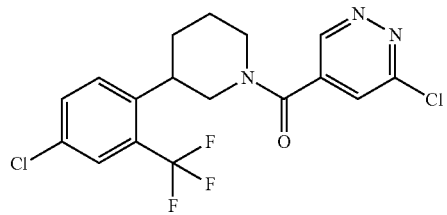 [SMILES: O=C(c1cnnc(Cl)c1)N1CCCC(c2ccc(Cl)cc2C(F)(F)F)C1]

Prepared as described for 3-chloro-5-{[3-(4-chloro-2-methylphenyl)piperidin-1-yl]carbonyl}pyridazine (Intermediate 4) from 6-chloropyridazine-4-carboxylic acid (Intermediate 1b2) and 3-[4-chloro-2-(trifluoromethyl)phenyl]piperidine hydrochloride (Intermediate 1a6).

MS ES⁺: 404

Intermediate 6

3-Chloro-5-({3-[2-methoxy-4-(trifluoromethyl)phenyl]piperidin-1-yl}carbonyl)pyridazine

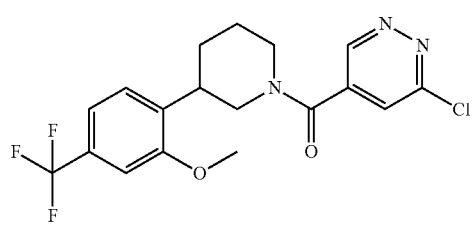 [SMILES: COc1cc(C(F)(F)F)ccc1C1CCCN(C(=O)c2cnnc(Cl)c2)C1]

3-[2-methoxy-4-(trifluoromethyl)phenyl]piperidine hydrochloride (280 mg, 0.947 mmol) (Intermediate 1b3) was dissolved in DCM (30 mL) and treated with 6-chloropyridazine-4-carboxylic acid (150 mg, 0.947 mmol) (Intermediate 1b2), propylphosphonic anhydride (50% in EtOAc) (1.2 g, 1.894 mmol) and triethylamine and stirred at room temperature for 3 hours. The reaction was then quenched with 2N NaHCO₃ and stirred for 30 minutes. Reaction was then diluted with DCM (10 mL) and passed through a phase separation cartridge and concentrated in vacuo. The crude product was purified by column chromatography on silica, eluting with 0-100% ethyl acetate/petrol to afford 3-chloro-5-({3-[2-methoxy-4-(trifluoromethyl)phenyl]piperidin-1-yl}carbonyl)pyridazine (0.291 g, 0.729 mmol, 77% yield) as a colourless foam.

MS ES⁺: 400

Intermediate 7

3-Chloro-5-{[3-(4-methoxy-2-methylphenyl)piperidin-1-yl]carbonyl}pyridazine

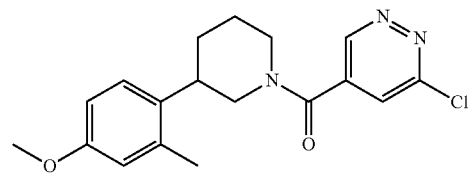 [SMILES: COc1ccc(C2CCCN(C(=O)c3cnnc(Cl)c3)C2)c(C)c1]

Prepared as described for 3-chloro-5-({3-[2-methoxy-4-(trifluoromethyl)phenyl]piperidin-1-yl}carbonyl)pyridazine (Intermediate 6) from 6-chloropyridazine-4-carboxylic acid (Intermediate 1b2) and 3-(4-methoxy-2-methylphenyl)piperidine (Intermediate 1a22).

MS ES⁺: 346

Intermediate 8

3-Chloro-5-({3-[4-methoxy-2-(trifluoromethyl)phenyl]piperidin-1-yl}carbonyl)pyridazine

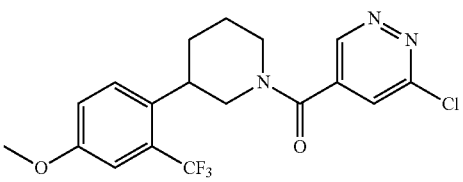 [SMILES: COc1ccc(C2CCCN(C(=O)c3cnnc(Cl)c3)C2)c(C(F)(F)F)c1]

Prepared as described for 3-chloro-5-({3-[2-methoxy-4-(trifluoromethyl)phenyl]piperidin-1-yl}carbonyl)pyridazine (Intermediate 6) from 3-[4-methoxy-2-(trifluoromethyl)phenyl]piperidine hydrochloride (Intermediate 1a21) and 6-chloropyridazine-4-carboxylic acid (Intermediate 1b2).

MS ES⁺: 400

Intermediate 9

3-Chloro-5-{[3-(4-chloro-2-ethoxyphenyl)piperidin-1-yl]carbonyl}pyridazine

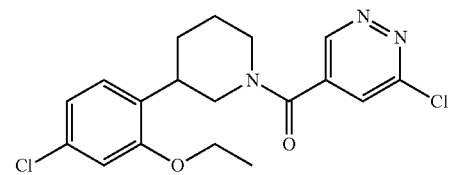 [SMILES: CCOc1cc(Cl)ccc1C1CCCN(C(=O)c2cnnc(Cl)c2)C1]

Prepared as described for 3-chloro-5-({3-[2-methoxy-4-(trifluoromethyl)phenyl]piperidin-1-yl}carbonyl)pyridazine (Intermediate 6) from 6-chloropyridazine-4-carboxylic acid (Intermediate 1b2) and 3-(4-chloro-2-ethoxyphenyl)piperidine hydrochloride (Intermediate 1a20).

MS ES⁺: 381

Intermediate 10

3-Chloro-4-{[3-(4-chloro-2-methylphenyl)piperidin-1-yl]carbonyl}-6-methylpyridazine

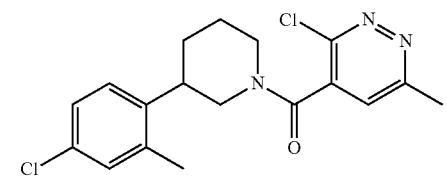 [SMILES: Cc1cc(C(=O)N2CCCC(c3ccc(Cl)cc3C)C2)c(Cl)nn1]

Prepared as described for 3-chloro-5-({3-[2-methoxy-4-(trifluoromethyl)phenyl]piperidin-1-yl}carbonyl)pyridazine (Intermediate 6) from 3-(4-chloro-2-methylphenyl)piperidine hydrochloride (Intermediate 1a5) and 3-chloro-6-methylpyridazine-4-carboxylic acid.

MS ES⁺: 364

Intermediate 11

3-Chloro-5-{[3-(2-methoxyphenyl)piperidin-1-yl]carbonyl}pyridazine

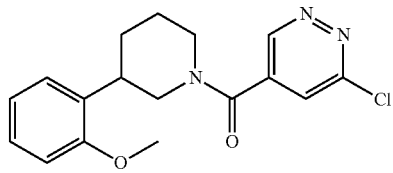 [SMILES: COc1ccccc1C1CCCN(C(=O)c2cnnc(Cl)c2)C1]

Prepared as described for 3-chloro-5-({3-[2-methoxy-4-(trifluoromethyl)phenyl]piperidin-1-yl}carbonyl)pyridazine (Intermediate 6) from 3-(2-methoxyphenyl)piperidine (Intermediate 1a18) and 6-chloropyridazine-4-carboxylic acid (Intermediate 1b2).

MS ES$^+$: 332

Intermediate 12

1-[(6-Chloropyridazin-4-yl)carbonyl]-3-(4-methoxyphenyl)azepane

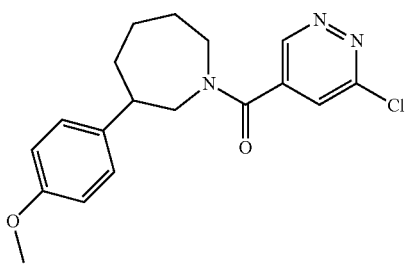 [SMILES: COc1ccc(C2CCCCN(C(=O)c3cnnc(Cl)c3)C2)cc1]

Prepared as described for 3-chloro-5-({3-[2-methoxy-4-(trifluoromethyl)phenyl]piperidin-1-yl}carbonyl)pyridazine (Intermediate 6) from 6-chloropyridazine-4-carboxylic acid (Intermediate 1b2) and 3-(4-methoxyphenyl)azepane hydrochloride.

MS ES$^+$: 346

Intermediate 13

3-(4-Chlorophenyl)-1-[(6-chloropyridazin-4-yl)carbonyl]azepane

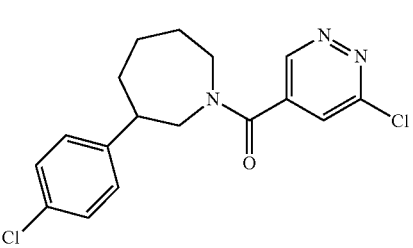 [SMILES: O=C(c1cnnc(Cl)c1)N1CCCCC(c2ccc(Cl)cc2)C1]

Prepared as described for 3-chloro-5-({3-[2-methoxy-4-(trifluoromethyl)phenyl]piperidin-1-yl}carbonyl)pyridazine (Intermediate 6) from 6-chloropyridazine-4-carboxylic acid (Intermediate 1b2) and 3-(4-chlorophenyl)azepane hydrochloride.

MS ES$^+$: 350

2. EXAMPLES

Example 1

4-{[3-(2-Fluorophenyl)piperidin-1-yl]carbonyl}-N,N-dimethylpyridin-2-amine

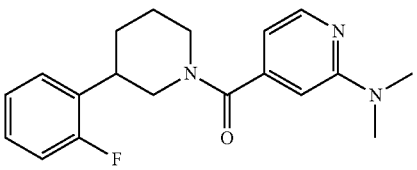 [SMILES: CN(C)c1cc(C(=O)N2CCCC(c3ccccc3F)C2)ccn1]

2-(Dimethylamino)isonicotinic acid (75 mg, 0.451 mmol) was dissolved in DCM (3 mL) at room temperature and 3-(2-fluorophenyl)piperidine hydrochloride (120 mg, 0.558 mmol) (Intermediate 1a1) was added, followed by HOBt (77 mg, 0.505 mmol), EDC (108 mg, 0.564 mmol) and Et$_3$N (0.126 mL, 0.903 mmol). The mixture was stirred at room temperature for 17 hours. Water was added to the reaction mixture which was stirred vigorously for 30 minutes before the phases were separated using a phase separator cartridge. The organics were concentrated in vacuo. The residues were dissolved in DMSO (together with a few drops of methanol) and purified by preparative LCMS (basic conditions) to give 4-{[3-(2-fluorophenyl)piperidin-1-yl]carbonyl}-N,N-dimethylpyridin-2-amine (15 mg, 0.046 mmol, 10%)

$^1$H NMR (400 MHz, DCM-d$_2$) δ ppm 1.54-2.15 (m, 4 H) 2.70-2.94 (m, 1 H) 2.98-3.21 (m, 8 H) 3.68-3.87 (m, 1 H) 4.76 (m, 1 H) 6.44-6.60 (m, 2 H) 6.94-7.38 (m, 4 H) 8.18 (m, 1 H)

MS ES$^+$: 328.

Example 2

4-{[3-(2,4-Dichlorophenyl)piperidin-1-yl]carbonyl}-N,N-dimethylpyridin-2-amine

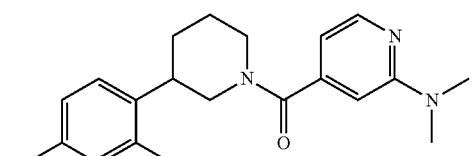

Prepared as described for 4-{([3-(2-fluorophenyl)piperidin-1-yl]carbonyl}-N,N-dimethylpyridin-2-amine (Example 1) using 2-(dimethylamino)isonicotinic acid and 3-(2,4-dichlorophenyl)piperidine hydrochloride (Intermediate 1a2).

$^1$H NMR (400 MHz, DCM-d$_2$) δ ppm 1.55-2.14 (m, 4 H) 2.69-3.33 (m, 9 H) 3.77 (m, 1H) 4.77 (m, 1 H) 6.45-6.58 (m, 2 H) 7.11-7.52 (m, 3 H) 8.10-8.27 (m, 1 H)

MS ES$^+$: 378.

Example 3

4-{[3-(4-Chlorophenyl)piperidin-1-yl]carbonyl}-2-cyclopropylpyridine

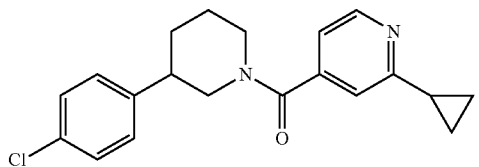 [SMILES: O=C(c1ccnc(C2CC2)c1)N1CCCC(c2ccc(Cl)cc2)C1]

Prepared as described for 4-{[3-(2-fluorophenyl)piperidin-1-yl]carbonyl}-N,N-dimethylpyridin-2-amine (Example 1) from 3-(4-chlorophenyl)piperidine hydrochloride (Intermediate 1a3) and lithium(1+) ion 2-cyclopropylpyridine-4-carboxylate (Intermediate 1a4).

$^1$H NMR (400 MHz, DCM-d$_2$) δ ppm 1.10-1.31 (m, 4 H) 1.52-2.19 (m, 4 H) 2.64-2.91 (m, 3 H) 2.99-3.16 (m, 1 H) 3.58 (m, 1 H) 4.74 (m, 1 H) 7.06-7.41 (m, 6 H) 8.53 (m, 1 H)

MS ES$^+$: 341.

Example 4

4-{[3-(4-Chloro-2-methylphenyl)piperidin-1-yl]carbonyl}-2-ethylpyridine

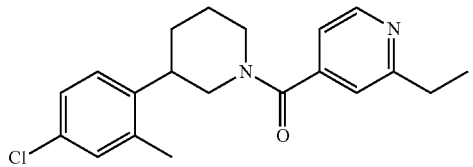 [SMILES: CCc1cc(C(=O)N2CCCC(c3ccc(Cl)cc3C)C2)ccn1]

Prepared as described for 4-{[3-(2-fluorophenyl)piperidin-1-yl]carbonyl}-N,N-dimethylpyridin-2-amine (Example 1) from 3-(4-chloro-2-methylphenyl)piperidine hydrochloride (Intermediate 1a5) and 2-ethylisonicotinic acid.

$^1$H NMR (400 MHz, DCM-d$_2$) δ ppm 1.23-1.43 (m, 3 H) 1.51-2.09 (m, 4 H) 2.10-2.52 (m, 3 H) 2.62-3.16 (m, 5 H) 3.47-3.73 (m, 1 H) 4.63-4.85 (m, 1 H) 6.96-7.33 (m, 5 H) 8.50-8.65 (m, 1 H)

MS ES$^+$: 343.

Example 5

4-{[3-(4-Chloro-2-methylphenyl)piperidin-1-yl]carbonyl}-2-methylpyridine

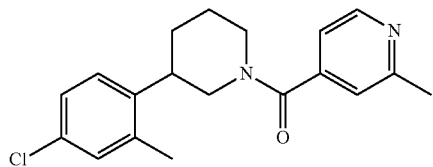 [SMILES: Cc1cc(C(=O)N2CCCC(c3ccc(Cl)cc3C)C2)ccn1]

Prepared as described for 4-{[3-(2-fluorophenyl)piperidin-1-yl]carbonyl}-N,N-dimethylpyridin-2-amine (Example 1) from 3-(4-chloro-2-methylphenyl)piperidine hydrochloride (Intermediate 1a5) and 2-methylisonicotinic acid.

$^1$H NMR (400 MHz, DCM-d$_2$) δ ppm 1.52-2.08 (m, 4 H) 2.15 (s, 1 H) 2.44 (s, 1 H) 2.52-3.17 (m, 6 H) 3.47-3.73 (m, 1 H) 4.60-4.83 (m, 2H) 6.97-7.28 (m, 5 H) 8.44-8.75 (m, 1 H)

MS ES$^+$: 329.

Example 6

4-({3-[4-Chloro-2-(trifluoromethyl)phenyl]piperidin-1-yl}carbonyl)-2-ethylpyridine

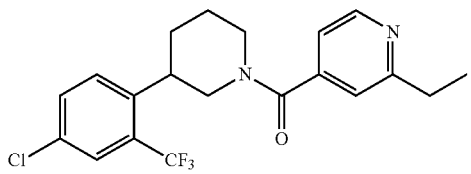

Prepared as described for 4-{[3-(2-fluorophenyl)piperidin-1-yl]carbonyl}-N,N-dimethylpyridin-2-amine (Example 1) from 3-[4-chloro-2-(trifluoromethyl)phenyl]piperidine hydrochloride (Intermediate 1a6) and 2-ethylisonicotinic acid.

$^1$H NMR (400 MHz, DCM-d$_2$) δ ppm 1.27 (br. s., 3 H) 1.52-2.30 (m, 4 H) 2.70-3.28 (m, 5 H) 3.43-3.81 (m, 1 H) 4.67-4.89 (m, 1 H) 6.99-7.79 (m, 5 H) 8.47-8.67 (m, 1 H)

MS ES$^+$: 397.

Example 7

4-({3-[4-Chloro-2-(trifluoromethyl)phenyl]piperidin-1-yl}carbonyl)-N,N-dimethylpyridin-2-amine

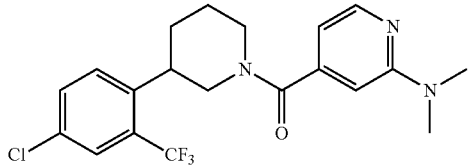 [SMILES: CN(C)c1cc(C(=O)N2CCCC(c3ccc(Cl)cc3C(F)(F)F)C2)ccn1]

Prepared as described for 4-{[3-(2-fluorophenyl)piperidin-1-yl]carbonyl}-N,N-dimethylpyridin-2-amine (Example 1) from 3-[4-chloro-2-(trifluoromethyl)phenyl]piperidine hydrochloride (Intermediate 1a6) and 2-(dimethylamino)isonicotinic acid.

$^1$H NMR (400 MHz, DCM-d$_2$) δ ppm 1.67-2.16 (m, 4 H) 2.75-2.85 (m, 1 H) 2.99-3.25 (m, 8 H) 3.56-3.87 (m, 1 H) 4.67-4.84 (m, 1 H) 6.37-6.61 (m, 2 H) 7.31-7.77 (m, 3 H) 8.07-8.25 (m, 1 H)

MS ES$^+$: 412.

Example 8

4-{[3-(4-Chlorophenyl)piperidin-1-yl]carbonyl}-N-(propan-2-yl)pyridin-2-amine

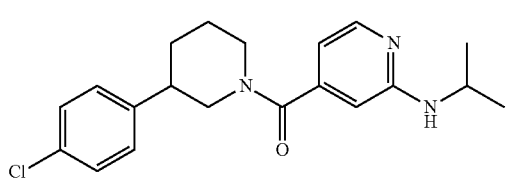 [SMILES: CC(C)Nc1cc(C(=O)N2CCCC(c3ccc(Cl)cc3)C2)ccn1]

A solution of 4-{[3-(4-chlorophenyl)piperidin-1-yl]carbonyl}-2-fluoropyridine (Intermediate 1a7) in IPA (4 mL) in a microwave vial was treated with propan-2-amine (0.015 mL, 0.188 mmol) and triethylamine (0.044 mL, 0.314 mmol). The vial was sealed and the reaction mixture was heated at 100° C. for 4 days. The reaction mixture was concentrated under vacuum and the crude product was purified by preparative LCMS (0.1% ammonia modifier) to give 4-{[3-(4-chlorophenyl)piperidin-1-yl]carbonyl}-N-(propan-2-yl)pyridin-2-amine (35 mg, 0.097 mmol, yield 62%).

$^1$H NMR (400 MHz, DCM-d$_2$) δ ppm 1.17-1.32 (m, 6 H) 1.48-2.22 (m, 5H) 2.59-2.89 (m, 2 H) 3.05 (m, 1 H) 3.64-3.99 (m, 2 H) 4.72 (m, 1 H) 6.32-6.60 (m, 2 H) 7.10 (m, 1 H) 7.21-7.45 (m, 3 H) 7.98-8.09 (m, 1 H)

MS ES$^+$: 358.

Example 9

4-({3-[4-Chloro-2-(trifluoromethyl)phenyl]piperidin-1-yl}carbonyl)-2-methoxypyridine

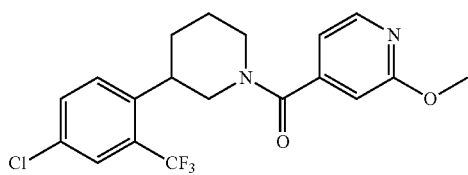 [SMILES: COc1cc(C(=O)N2CCCC(c3ccc(Cl)cc3C(F)(F)F)C2)ccn1]

Prepared as described for 4-{[3-(2-fluorophenyl)piperidin-1-yl]carbonyl}-N,N-dimethylpyridin-2-amine (Example 1) from 3-[4-chloro-2-(trifluoromethyl)phenyl]piperidine hydrochloride (Intermediate 1a6) and using 2-methoxyisonicotinic acid.

$^1$H NMR (400 MHz, DCM-d$_2$) δ ppm 1.55-2.14 (m, 4 H) 2.82 (m, 1 H) 2.95-3.23 (m, 2 H) 3.54-3.80 (m, 1 H) 3.88-4.09 (m, 3 H) 4.66-4.85 (m, 1 H) 6.61-7.01 (m, 2 H) 7.29-7.78 (m, 3 H) 8.13-8.36 (m, 1 H)

MS ES$^+$: 399.

Example 10

4-({3-[4-Chloro-2-(trifluoromethyl)phenyl]piperidin-1-yl}carbonyl)-2-methylpyridine

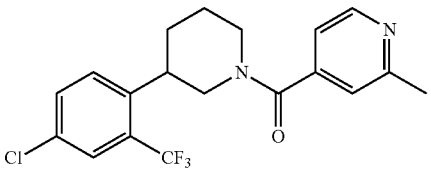 [SMILES: Cc1cc(C(=O)N2CCCC(c3ccc(Cl)cc3C(F)(F)F)C2)ccn1]

Prepared as described for 4-{[3-(2-fluorophenyl)piperidin-1-yl]carbonyl}-N,N-dimethylpyridin-2-amine (Example 1) from 3-[4-chloro-2-(trifluoromethyl)phenyl]piperidine hydrochloride (Intermediate 1a6) and 2-methylisonicotinic acid.

$^1$H NMR (400 MHz, DCM-d$_2$) δ ppm 1.53-2.18 (m, 5 H) 2.48-2.69 (m, 3 H) 2.73-2.91 (m, 1 H) 3.02-3.26 (m, 1 H) 3.50-3.76 (m, 1 H) 4.69-4.89 (m, 1 H) 7.02-7.79 (m, 5 H) 8.44-8.64 (m, 1 H)

MS ES$^+$: 383

Example 11

N-Methyl-4-{[3-(4-methylphenyl)piperidin-1-yl]carbonyl}pyridin-2-amine

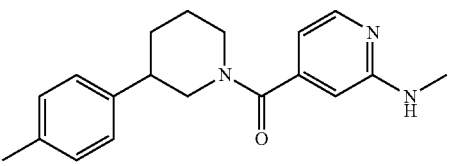

Prepared as described for 4-{[3-(2-fluorophenyl)piperidin-1-yl]carbonyl}-N,N-dimethylpyridin-2-amine (Example 1) from 3-(4-methylphenyl)piperidine hydrochloride and 2-(methylamino)isonicotinic acid.

$^1$H NMR (400 MHz, CHCl$_3$-d) δ ppm 1.68-2.00 (m, 3 H) 2.06-2.16 (m, 1 H) 2.29-2.40 (m, 3 H) 2.60-2.85 (m, 2 H) 2.90-3.10 (m, 4 H) 3.71-3.83 (m, 1 H) 4.60-4.72 (m, 1 H) 4.76-4.87 (m, 1 H) 6.33-6.44 (m, 1 H) 6.52-6.61 (m, 1 H) 6.98-7.05 (m, 1 H) 7.07-7.22 (m, 3 H) 8.10-8.19 (m, 1 H)

MS ES$^+$: 310

Example 12

2-Methyl-4-{[3-(4-methylphenyl)piperidin-1-yl]carbonyl}pyridine

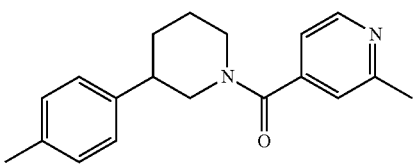

Prepared as described for 4-{[3-(2-fluorophenyl)piperidin-1-yl]carbonyl}-N,N-dimethylpyridin-2-amine (Example 1) from 3-(4-methylphenyl)piperidine hydrochloride and 2-methylisonicotinic acid.

$^1$H NMR (400 MHz, CHCl$_3$-d) δ ppm 1.68-2.00 (m, 2 H) 2.07-2.19 (m, 1 H) 2.25-2.41 (m, 3 H) 2.55-2.71 (m, 4 H) 2.73-2.87 (m, 2 H) 2.99-3.12 (m, 1 H) 3.61-3.73 (m, 1 H) 4.75-4.89 (m, 1 H) 6.97-7.04 (m, 1 H) 7.05-7.24 (m, 5 H) 8.52-8.63 (m, 1 H)

MS ES$^+$: 295

Example 13

N,N-Dimethyl-4-{[3-(3-methylphenyl)piperidin-1-yl]carbonyl}pyridin-2-amine

Prepared as described for 4-{[3-(2-fluorophenyl)piperidin-1-yl]carbonyl}-N,N-dimethylpyridin-2-amine (Example 1) from 3-(3-methylphenyl)piperidine hydrochloride and 2-(dimethylamino)isonicotinic acid.

$^1$H NMR (400 MHz, CHCl$_3$-d) δ ppm 1.70-1.99 (m, 2 H) 2.06-2.17 (m, 1 H) 2.27-2.41 (m, 3 H) 2.60-2.86 (m, 2 H) 2.97-3.17 (m, 8 H) 3.73-3.84 (m, 1 H) 4.75-4.89 (m, 1 H) 6.45-6.57 (m, 2 H) 6.89-6.96 (m, 1 H) 7.01-7.27 (m, 3 H) 8.15-8.26 (m, 1 H)

MS ES$^+$: 324

Example 14

N,N-Dimethyl-4-{[3-(2-methylphenyl)piperidin-1-yl]carbonyl}pyridin-2-amine

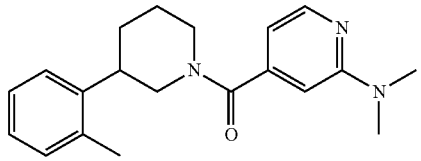 [SMILES: Cc1ccccc1C1CCCN(C(=O)c2ccnc(N(C)C)c2)C1]

Prepared as described for 4-{[3-(2-fluorophenyl)piperidin-1-yl]carbonyl}-N,N-dimethylpyridin-2-amine (Example 1) from 3-(2-methylphenyl)piperidine hydrochloride and 2-(dimethylamino)isonicotinic acid.

$^1$H NMR (400 MHz, CHCl$_3$-d) δ ppm 1.69-2.11 (m, 3 H) 2.19 (s, 2 H) 2.46 (s, 1 H) 2.67-3.05 (m, 3 H) 3.05-3.18 (m, 7 H) 3.64-3.86 (m, 1 H) 4.75-4.89 (m, 1 H) 6.42-6.59 (m, 2 H) 7.05-7.26 (m, 4 H) 8.14-8.26 (m, 1 H)

MS ES$^+$: 324

Example 15

N,N-Dimethyl-4-[(3-phenylpiperidin-1-yl)carbonyl]pyridin-2-amine

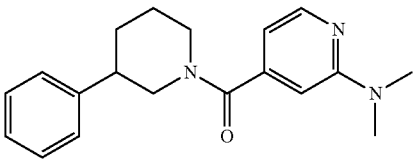 [SMILES: CN(C)c1cc(C(=O)N2CCCC(c3ccccc3)C2)ccn1]

Prepared as described for 4-{[3-(2-fluorophenyl)piperidin-1-yl]carbonyl}-N,N-dimethylpyridin-2-amine (Example 1) from 3-phenylpiperidine and 2-(dimethylamino)isonicotinic acid.

$^1$H NMR (400 MHz, CHCl$_3$-d) δ ppm 1.71-1.99 (m, 3 H) 2.09-2.19 (m, 1 H) 2.65-2.90 (m, 2 H) 2.99-3.17 (m, 7 H) 3.75-3.85 (m, 1 H) 4.78-4.89 (m, 1 H) 6.47-6.56 (m, 2 H) 7.09-7.17 (m, 1 H) 7.19-7.41 (m, 4 H) 8.17-8.26 (m, 1 H)

MS ES$^+$: 310

Example 16

4-{[3-(4-Chlorophenyl)piperidin-1-yl]carbonyl}-N,N-dimethylpyridin-2-amine

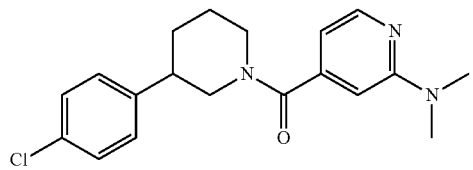 [SMILES: CN(C)c1cc(C(=O)N2CCCC(c3ccc(Cl)cc3)C2)ccn1]

Prepared as described for 4-{[3-(2-fluorophenyl)piperidin-1-yl]carbonyl}-N,N-dimethylpyridin-2-amine (Example 1) from 3-(4-chlorophenyl)piperidine hydrochloride (Intermediate 1a3) and 2-(dimethylamino)isonicotinic acid. The reaction product was purified via silica column chromatography eluted with 0-100% ethyl acetate/petrol. The residue was recrystallised from MTBE and petrol to give the title product.

$^1$H NMR (400 MHz, CHCl$_3$-d) δ ppm 1.61-2.01 (m, 3 H) 2.05-2.19 (m, 1 H) 2.63-2.89 (m, 2 H) 2.92-3.19 (m, 7 H) 3.71-3.85 (m, 1 H) 4.73-4.88 (m, 1 H) 6.44-6.55 (m, 2 H) 7.00-7.10 (m, 1 H) 7.18-7.38 (m, 3 H) 8.16-8.26 (m, 1 H)

MS ES$^+$: 344

Example 17

4-{[(3S)-3-(4-Chlorophenyl)piperidin-1-yl]carbonyl}-N,N-dimethylpyridin-2-amine

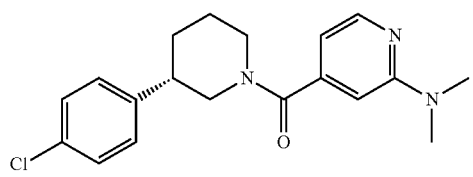 [SMILES: CN(C)c1cc(C(=O)N2CCC[C@@H](c3ccc(Cl)cc3)C2)ccn1]

Prepared as described for 4-{[3-(4-chlorophenyl)piperidin-1-yl]carbonyl}-N,N-dimethylpyridin-2-amine (Example 16) from (3S)-3-(4-chlorophenyl)piperidine (Intermediate 1a3A) and 2-(dimethylamino)isonicotinic acid hydrochloride.

$^1$H NMR (400 MHz, CHCl$_3$-d) δ ppm 1.66-2.00 (m, 3 H) 2.04-2.16 (m, 1 H) 2.63-2.88 (m, 2 H) 2.93-3.18 (m, 7 H) 3.72-3.85 (m, 1 H) 4.75-4.87 (m, 1 H) 6.44-6.57 (m, 2 H) 7.00-7.10 (m, 1 H) 7.18-7.38 (m, 3 H) 8.15-8.26 (m, 1 H)

MS ES$^+$: 344

Chiral SFC (Chiralpak OD-H column, isocratic MeOH with ammonium acetate [10 mM]) Rt=9.43 mins (98% e.e.)

Example 18

4-{[(3R)-3-(4-Chlorophenyl)piperidin-1-yl]carbonyl}-N,N-dimethylpyridin-2-amine

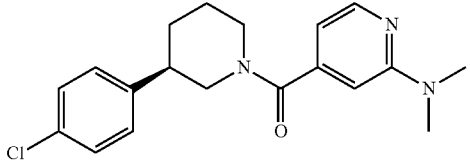 [SMILES: CN(C)c1cc(C(=O)N2CCC[C@H](c3ccc(Cl)cc3)C2)ccn1]

Prepared as described for 4-{[3-(4-chlorophenyl)piperidin-1-yl]carbonyl}-N,N-dimethylpyridin-2-amine (Example 16) from (3R)-3-(4-chlorophenyl)piperidine (Intermediate 1a3B) and 2-(dimethylamino)isonicotinic acid hydrochloride.

$^1$H NMR (400 MHz, CHCl$_3$-d) δ ppm 1.66-2.00 (m, 3 H) 2.04-2.16 (m, 1 H) 2.63-2.88 (m, 2 H) 2.93-3.18 (m, 7 H) 3.72-3.85 (m, 1 H) 4.75-4.87 (m, 1 H) 6.44-6.57 (m, 2 H) 7.00-7.10 (m, 1 H) 7.18-7.38 (m, 3 H) 8.15-8.26 (m, 1 H)

MS ES$^+$: 344

Chiral SFC (Chiralpak OD-H column, isocratic MeOH with Ammonium Acetate [10 mM]) Rt=8.07 mins (100% e.e.)

A sample of the material was recrystallised from MeOH/EtOAc. Single crystal x-ray structure determination assigns absolute stereochemistry as the R configuration by the Flack parameter (χ=0.01(1)).

Example 19

4-{[3-(4-Fluorophenyl)piperidin-1-yl]carbonyl}-N,N-dimethylpyridin-2-amine

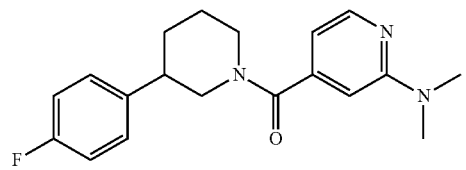 [SMILES: CN(C)c1cc(C(=O)N2CCCC(c3ccc(F)cc3)C2)ccn1]

Prepared as described for 4-{[3-(2-fluorophenyl)piperidin-1-yl]carbonyl}-N,N-dimethylpyridin-2-amine (Example 1) from 2-(dimethylamino)isonicotinic acid hydrochloride and 3-(4-fluorophenyl)piperidine.

$^1$H NMR (400 MHz, CHCl$_3$-d) δ ppm 1.65-2.00 (m, 3 H) 2.05-2.16 (m, 1 H) 2.64-2.88 (m, 2 H) 2.94-3.08 (m, 1 H) 3.09-3.17 (m, 6 H) 3.73-3.83 (m, 1 H) 4.75-4.87 (m, 1 H) 6.46-6.56 (m, 2 H) 6.93-7.12 (m, 3 H) 7.21-7.33 (m, 1 H) 8.17-8.25 (m, 1 H)

MS ES$^+$: 328

Example 20

2-Ethyl-4-{[3-(4-methylphenyl)piperidin-1-yl]carbonyl}pyridine

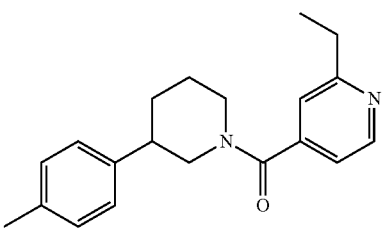 [SMILES: CCc1cc(C(=O)N2CCCC(c3ccc(C)cc3)C2)ccn1]

Prepared as described for 4-{[3-(2-fluorophenyl)piperidin-1-yl]carbonyl}-N,N-dimethylpyridin-2-amine (Example 1) from 3-(4-methylphenyl)piperidine hydrochloride and 2-ethylisonicotinic acid. The product was purified via silica column chromatography (solvent system: 0-100% ethyl acetate/petrol).

$^1$H NMR (400 MHz, CHCl$_3$-d) δ ppm 1.27-1.41 (m, 3 H) 1.68-1.84 (m, 2 H) 1.92-2.01 (m, 1 H) 2.09-2.17 (m, 1 H) 2.28-2.40 (m, 3 H) 2.62-2.94 (m, 4 H) 2.98-3.13 (m, 1 H) 3.61-3.73 (m, 1 H) 4.74-4.90 (m, 1 H) 6.96-7.05 (m, 1 H) 7.07-7.24 (m, 5 H) 8.54-8.66 (m, 1 H)

MS ES$^+$: 309

Example 21

2-(Azetidin-1-yl)-4-{[3-(4-methylphenyl)piperidin-1-yl]carbonyl}pyridine

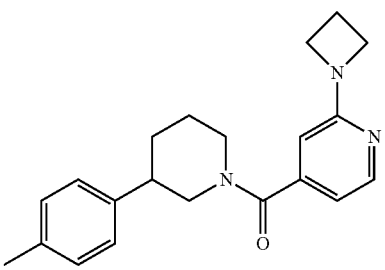 [SMILES: Cc1ccc(C2CCCN(C(=O)c3ccnc(N4CCC4)c3)C2)cc1]

Azetidine (0.029 g, 0.503 mmol) was added to a solution of 2-fluoro-4-{[3-(4-methylphenyl)piperidin-1-yl]carbonyl}pyridine (0.05 g, 0.168 mmol) (Intermediate 1a8) in THF (1 mL) under nitrogen. The reaction was heated to 85° C. for 18 hours. The crude reaction mixture was purified by silica column chromatography eluting with 0-100% ethyl acetate/petrol to afford 2-(azetidin-1-yl)-4-{[3-(4-methylphenyl)piperidin-1-yl]carbonyl}pyridine (49 mg, 0.146 mmol, 87% yield) as a solid.

¹H NMR (400 MHz, CHCl₃-d) δ ppm 1.65-1.98 (m, 3 H) 2.04-2.17 (m, 1 H) 2.28-2.49 (m, 5 H) 2.60-2.83 (m, 2 H) 2.94-3.09 (m, 1 H) 3.71-3.81 (m, 1 H) 4.01-4.13 (m, 4 H) 4.74-4.86 (m, 1 H) 6.20-6.31 (m, 1 H) 6.51-6.59 (m, 1 H) 6.98-7.06 (m, 1 H) 7.07-7.22 (m, 3 H) 8.13-8.23 (m, 1 H)

MS ES⁺: 336

Example 22

2-(Azetidin-1-yl)-4-{[3-(4-chlorophenyl)piperidin-1-yl]carbonyl}pyridine

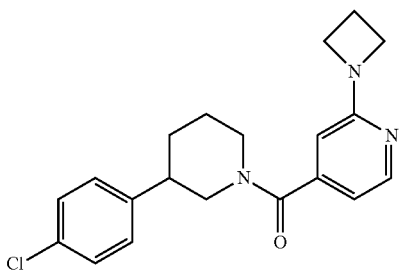 [SMILES: O=C(c1ccnc(N2CCC2)c1)N1CCCC(c2ccc(Cl)cc2)C1]

Prepared as described for 2-(azetidin-1-yl)-4-{[3-(4-methylphenyl)piperidin-1-yl]carbonyl}pyridine (Example 21) from 4-{[3-(4-chlorophenyl)piperidin-1-yl]carbonyl}-2-fluoropyridine (Intermediate 1a7) and azetidine.

¹H NMR (400 MHz, CHCl₃-d) δ ppm 1.62-2.01 (m, 3 H) 2.02-2.17 (m, 1 H) 2.35-2.50 (m, 2 H) 2.63-2.88 (m, 2 H) 2.93-3.10 (m, 1 H) 3.69-3.83 (m, 1 H) 4.01-4.15 (m, 4 H) 4.72-4.85 (m, 1 H) 6.20-6.31 (m, 1 H) 6.51-6.58 (m, 1 H) 6.99-7.10 (m, 1 H) 7.17-7.38 (m, 3 H) 8.13-8.25 (m, 1 H)

MS ES⁺: 356

Example 23

2-(Azetidin-1-yl)-4-{[3-(2-methylphenyl)piperidin-1-yl]carbonyl}pyridine

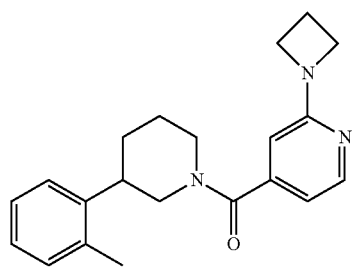 [SMILES: Cc1ccccc1C1CCCN(C(=O)c2ccnc(N3CCC3)c2)C1]

Prepared as described for 2-(azetidin-1-yl)-4-{[3-(4-methylphenyl)piperidin-1-yl]carbonyl}pyridine (Example 21) from 2-fluoro-4-{[3-(2-methylphenyl)piperidin-1-yl]carbonyl}pyridine (Intermediate 1a9) and azetidine.

¹H NMR (400 MHz, CHCl₃-d) δ ppm 1.69-1.88 (m, 2 H) 1.91-2.12 (m, 2 H) 2.20 (s, 2 H) 2.33-2.52 (m, 3 H) 2.64-3.14 (m, 3 H) 3.61-3.85 (m, 1 H) 3.99-4.16 (m, 4 H) 4.73-4.90 (m, 1 H) 6.16-6.34 (m, 1 H) 6.50-6.61 (m, 1 H) 7.09-7.26 (m, 4 H) 8.11-8.25 (m, 1 H)

MS ES⁺: 336

Example 24

4-{[3-(4-Chloro-2-methylphenyl)piperidin-1-yl]carbonyl}-N,N-dimethylpyridin-2-amine

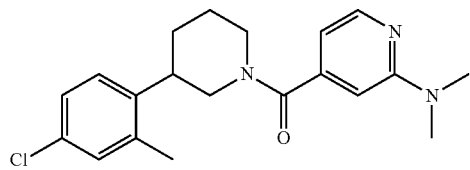 [SMILES: Cc1cc(Cl)ccc1C1CCCN(C(=O)c2ccnc(N(C)C)c2)C1]

Prepared as described for 4-{[3-(2-fluorophenyl)piperidin-1-yl]carbonyl}-N,N-dimethylpyridin-2-amine (Example 1) from 3-(4-chloro-2-methylphenyl)piperidine hydrochloride (Intermediate 1a5) and 2-(dimethylamino)isonicotinic acid hydrochloride.

¹H NMR (CHCl₃-d) δ ppm 1.59-2.08 (m, 4 H) 2.16-2.43 (m, 3 H) 2.63-3.00 (m, 3 H) 3.06-3.11 (s, 3 H) 3.14 (s, 3 H) 3.50-3.90 (m, 1 H) 4.68-4.88 (m, 1 H) 6.48-6.54 (m, 2 H) 7.08-7.21 (m, 3 H) 8.17-8.24 (m, 1 H)

MS ES⁺: 358

Example 25

4-{[3-(4-Chloro-2-fluorophenyl)piperidin-1-yl]carbonyl}-N,N-dimethylpyridin-2-amine

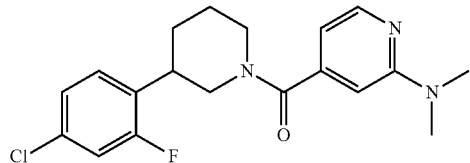 [SMILES: CN(C)c1cc(C(=O)N2CCCC(c3ccc(Cl)cc3F)C2)ccn1]

Prepared as described for 4-{[3-(2-fluorophenyl)piperidin-1-yl]carbonyl}-N,N-dimethylpyridin-2-amine (Example 1) from 3-(4-chloro-2-fluorophenyl)piperidine hydrochloride (Intermediate 1a10) and 2-(dimethylamino)isonicotinic acid hydrochloride.

¹H NMR (CHCl₃-d) δ ppm 1.72-2.15 (m, 4 H) 2.75-3.08 (m, 3 H) 3.12 (s, 6 H) 3.72-3.84 (m, 1 H) 4.75-4.84 (m, 1 H) 6.42-6.58 (m, 2 H) 6.94-7.22 (m, 3 H) 8.17-8.25 (m, 1 H)

MS ES⁺: 362

Example 26

4-{[3-(2-Chloro-4-fluorophenyl)piperidin-1-yl]carbonyl}-N,N-dimethylpyridin-2-amine

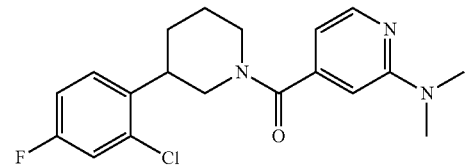 [SMILES: CN(C)c1cc(C(=O)N2CCCC(c3ccc(F)cc3Cl)C2)ccn1]

Prepared as described for 4-{[3-(2-fluorophenyl)piperidin-1-yl]carbonyl}-N,N-dimethylpyridin-2-amine (Example 1) from 3-(2-chloro-4-fluorophenyl)piperidine hydrochloride (Intermediate 1a11) and 2-(dimethylamino)isonicotinic acid hydrochloride.

$^1$H NMR (CHCl$_3$-d) δ ppm 1.49-2.17 (m, 4 H) 2.71-2.96 (m, 1 H) 2.98-3.32 (m, 6 H) 3.80 (m, 2 H) 4.83 (m, 2 H) 6.52 (m, 2 H) 6.89-7.22 (m, 2 H) 8.12-8.31 (m, 2 H)

MS ES$^+$: 362

Example 27

4-{[3-(4-Chlorophenyl)piperidin-1-yl]carbonyl}-N-methylpyridin-2-amine

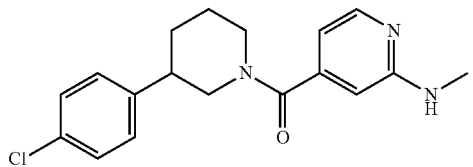 [SMILES: CNc1cc(C(=O)N2CCCC(c3ccc(Cl)cc3)C2)ccn1]

A solution of propylphosphonic anhydride (50% in EtOAc) (0.298 mL, 0.511 mmol) was added to a solution of 3-(4-chlorophenyl)piperidine (0.05 g, 0.256 mmol), triethylamine (0.071 mL, 0.511 mmol) and 2-(methylamino)isonicotinic acid (0.047 g, 0.307 mmol) in DCM (0.1 mL). The reaction was stirred at room temperature for 18 hours. Water was added to the reaction mixture which was stirred vigorously for 30 minutes before the phases were separated using a phase separation cartridge. The organic phase was concentrated in vacuo. The crude product was purified by preparative LCMS (basic conditions) to give the title compound 4-{[3-(4-chlorophenyl)piperidin-1-yl]carbonyl}-N-methylpyridin-2-amine (28 mg, 0.085 mmol, 33% yield).

$^1$H NMR (CHCl$_3$-d) δ ppm 1.50-2.02 (m, 4 H) 2.05-2.16 (m, 1 H) 2.64-2.87 (m, 2 H) 2.91-3.08 (m, 2 H) 3.70-3.84 (m, 1 H) 4.63-4.84 (m, 2 H) 6.30-6.45 (m, 1 H) 6.53-6.59 (m, 1 H) 7.01-7.12 (m, 1 H) 7.20-7.40 (m, 3 H) 8.11-8.20 (m, 1 H)

MS ES$^+$: 330

Example 28

4-{[3-(4-Chlorophenyl)piperidin-1-yl]carbonyl}-2,6-dimethylpyridine

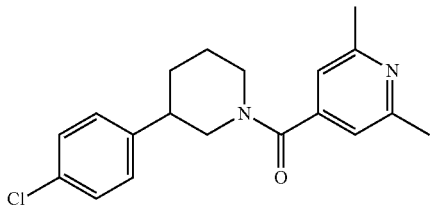 [SMILES: Cc1cc(C(=O)N2CCCC(c3ccc(Cl)cc3)C2)cc(C)n1]

Prepared as described for 4-{[3-(4-chlorophenyl)piperidin-1-yl]carbonyl}-N-methylpyridin-2-amine (Example 27) from 3-(4-chlorophenyl)piperidine and 2,6-dimethylisonicotinic acid.

$^1$H NMR (CHCl$_3$-d)) δ ppm 1.61 (m, 2 H) 1.74-1.86 (m, 1 H) 2.12-2.15 (m, 1 H) 2.33 (br. s., 3 H) 2.55 (br. s., 3 H) 2.81 (m, 2 H) 3.09 (m, 1 H) 3.85 (m, 1 H) 4.79-4.82 (m, 1 H) 7.02-7.13 (m, 1 H) 7.30-7.37 (m, 1 H) 7.40-7.62 (m, 2 H) 8.41 (s, 2 H)

MS ES$^+$: 329

Example 29

2-Chloro-4-{[3-(4-chlorophenyl)piperidin-1-yl]carbonyl}pyridine

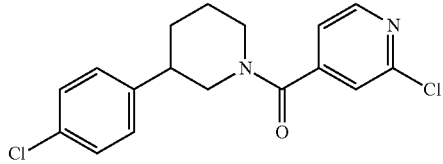 [SMILES: O=C(c1ccnc(Cl)c1)N1CCCC(c2ccc(Cl)cc2)C1]

A solution of propylphosphonic anhydride (50% in EtOAc) (1.5 mL, 2.56 mmol) was added to a solution of 3-(4-chlorophenyl)piperidine (250 mg, 1.27 mmol), triethylamine (0.36 mL, 2.56 mmol) and 2-chloroisonicotinic acid (242 mg, 1.53 mmol) in DCM (5 mL). The reaction was stirred at room temperature for 2 hours. The crude product was purified by column chromatography on basic silica eluted with 0-100% ethyl acetate/petrol to afford 2-chloro-4-{[3-(4-chlorophenyl)piperidin-1-yl]carbonyl}pyridine (413 mg, 1.23 mmol, 96%) as a solid.

$^1$H NMR (CHCl$_3$-d) δ ppm 1.49-1.64 (m, 1 H) 1.64-2.27 (m, 3 H) 2.62-2.99 (m, 2 H) 3.06-3.24 (m, 1 H) 3.63 (m, 1 H) 4.79-4.82 (m, 1 H) 6.97-7.13 (m, 1 H) 7.14-7.50 (m, 5 H) 8.37-8.65 (m, 1 H)

MS ES$^+$: 335

Example 30

4-{[3-(4-Chlorophenyl)piperidin-1-yl]carbonyl}-2-(propan-2-yl)pyridine

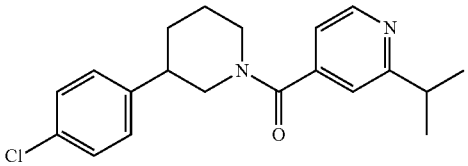 [SMILES: CC(C)c1cc(C(=O)N2CCCC(c3ccc(Cl)cc3)C2)ccn1]

Isopropylmagnesium chloride (0.403 mL, 0.805 mmol) was added dropwise to a solution of 2-chloro-4-{[3-(4-chlorophenyl)piperidin-1-yl]carbonyl}pyridine (0.15 g, 0.447 mmol) (Intermediate 1a12) and tris(((Z)-4-oxopent-2-en-2-yl)oxy)iron (7.90 mg, 0.022 mmol) in THF (4.47 mL) under nitrogen. The reaction was stirred at room temperature for 10 minutes, diluted with EtOAc and carefully quenched with a few drops of 2M hydrogen chloride. The mixture was diluted with ethyl acetate, washed with saturated sodium bicarbonate (1×5 mL), saturated brine (1×5 mL), dried over magnesium sulphate, filtered and concentrated in vacuo to give an oil. The crude product was purified by reverse phase preparative HPLC eluting with acetonitrile/water (with 0.1% ammonia) to afford 4-{[3-(4-chlorophenyl)piperidin-1-yl]carbonyl}-2-(propan-2-yl)pyridine (8 mg, 0.022 mmol, 5% yield) as a colourless gum.

¹H NMR (CHCl₃-d) δ ppm 1.23-1.45 (m, 6 H) 1.51-1.63 (m, 2 H) 1.69-1.85 (m, 2 H) 2.13-2.15 (m, 1 H) 2.70-2.94 (m, 1 H) 2.94-3.24 (m, 2 H) 3.60-3.76 (m, 1 H) 4.77-4.88 (m, 1 H) 6.97-7.15 (m, 2 H) 7.18-7.39 (m, 4 H) 8.58-8.73 (m, 1 H)
MS ES⁺: 343

Example 31

4-{[3-(4-Chloro-2-methylphenyl)piperidin-1-yl]carbonyl}-N-methylpyridin-2-amine

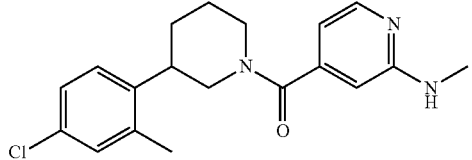 [SMILES: CNc1cc(C(=O)N2CCCC(c3ccc(Cl)cc3C)C2)ccn1]

Prepared as described for 4-{[3-(4-chlorophenyl)piperidin-1-yl]carbonyl}-N-methylpyridin-2-amine (Example 27) from 3-(4-chloro-2-methylphenyl)piperidine hydrochloride (Intermediate 1a5) and 2-(methylamino)isonicotinic acid. The reaction product was purified via column chromatography on basic silica (solvent system: 10-100% ethyl acetate/petrol).

¹H NMR (DCM-d₂) δ ppm 1.57-1.62 (m, 1 H) 1.74-2.05 (m, 3 H) 2.18-2.44 (m, 3 H) 2.63-3.14 (m, 7 H) 3.58-3.89 (m, 1 H) 4.61-4.83 (m, 1 H) 6.29-6.60 (m, 1 H) 7.05-7.29 (m, 3 H) 8.04-8.18 (m, 1 H)
MS ES⁺: 344

Example 32

4-{[3-(4-Chloro-2-methylphenyl)piperidin-1-yl]carbonyl}-2-methoxypyridine

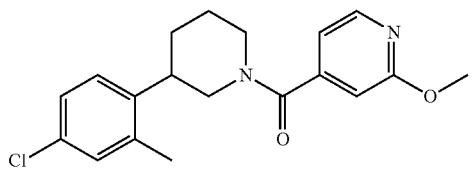 [SMILES: COc1cc(C(=O)N2CCCC(c3ccc(Cl)cc3C)C2)ccn1]

Prepared as described for 4-{[3-(4-chlorophenyl)piperidin-1-yl]carbonyl}-N-methylpyridin-2-amine (Example 27) from 3-(4-chloro-2-methylphenyl)piperidine hydrochloride (Intermediate 1a5) and 2-methoxyisonicotinic acid. The reaction product was purified via column chromatography on basic silica (solvent system: 10-100% ethyl acetate/petrol).

¹H NMR (DCM-d₂) δ ppm 1.59-1.65 (m, 1 H) 1.71-2.04 (m, 3 H) 2.17-2.44 (m, 3 H) 2.66-3.18 (m, 3 H) 3.57-3.79 (m, 1 H) 3.96-4.00 (m, 3 H) 4.64-4.82 (m, 1 H) 6.69-6.95 (m, 2 H) 7.08-7.25 (m, 3 H) 8.16-8.29 (m, 1 H)
MS ES⁺: 345

Example 33

2-(Azetidin-1-yl)-4-{[3-(4-chloro-2-methylphenyl)piperidin-1-yl]carbonyl}pyridine

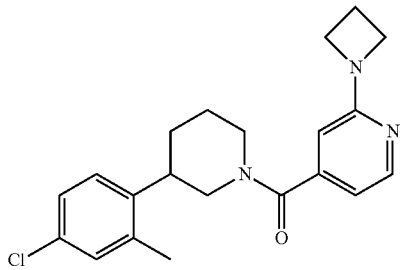 [SMILES: Cc1cc(Cl)ccc1C1CCCN(C(=O)c2ccnc(N3CCC3)c2)C1]

Prepared as described for 2-(azetidin-1-yl)-4-{[3-(4-methylphenyl)piperidin-1-yl]carbonyl}pyridine (Example 21) from 4-{[3-(4-chloro-2-methylphenyl)piperidin-1-yl]carbonyl}-2-fluoropyridine (Intermediate 1a13).

¹H NMR (MeOH-d₄) δ ppm 1.59-2.07 (m, 4 H) 2.35-2.56 (m, 3 H) 2.78-3.27 (m, 3 H) 3.43-3.61 (m, 1 H) 3.72-3.79 (m, 2 H) 4.07-4.15 (m, 4 H) 4.56-4.74 (m, 1 H) 6.30-6.42 (m, 1 H) 6.58-6.65 (m, 1 H) 7.10-7.35 (m, 3 H) 8.01-8.12 (m, 1 H)
MS ES⁺: 370

Example 34

2-Methoxy-4-{[3-(4-methylphenyl)piperidin-1-yl]carbonyl}pyridine

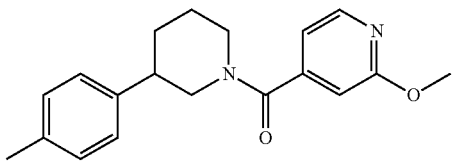

Prepared as described for 4-{[3-(2-fluorophenyl)piperidin-1-yl]carbonyl}-N,N-dimethylpyridin-2-amine (Example 1) from 3-(4-methylphenyl)piperidine hydrochloride and 2-methoxyisonicotinic acid.

¹H NMR (400 MHz, CHCl₃-d) δ ppm 1.68-1.99 (m, 3 H) 2.05-2.16 (m, 1 H) 2.28-2.40 (m, 3 H) 2.59-2.87 (m, 2 H) 2.99-3.11 (m, 1 H) 3.64-3.75 (m, 1 H) 3.90-4.02 (m, 3 H) 4.75-4.87 (m, 1 H) 6.70-6.80 (m, 1 H) 6.84-6.93 (m, 1 H) 6.97-7.06 (m, 1 H) 7.08-7.22 (m, 3 H) 8.17-8.29 (m, 1 H)
MS ES⁺: 311

Example 35

4-{[3-(4-Methylphenyl)piperidin-1-yl]carbonyl}-2-(pyrrolidin-1-yl)pyridine

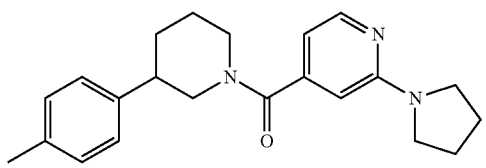 [SMILES: Cc1ccc(C2CCCN(C(=O)c3ccnc(N4CCCC4)c3)C2)cc1]

Prepared as described for 4-{[3-(2-fluorophenyl)piperidin-1-yl]carbonyl}-N,N-dimethylpyridin-2-amine (Example 1) from 3-(4-methylphenyl)piperidine hydrochloride and 2-(pyrrolidin-1-yl)isonicotinic acid. The reaction product was purified via column chromatography on silica (solvent system: 0-80% ethyl acetate/petrol).

$^1$H NMR (400 MHz, CHCl$_3$-d) δ ppm 1.67-1.83 (m, 2 H) 1.91-2.15 (m, 6 H) 2.29-2.39 (m, 3 H) 2.61-2.84 (m, 2 H) 2.96-3.09 (m, 1 H) 3.41-3.53 (m, 4 H) 3.74-3.85 (m, 1 H) 4.77-4.87 (m, 1 H) 6.29-6.39 (m, 1 H) 6.45-6.52 (m, 1 H) 6.98-7.05 (m, 1 H) 7.07-7.13 (m, 1 H) 7.14-7.22 (m, 2 H) 8.14-8.25 (m, 1 H)

MS ES$^+$: 350

Example 36

4-{[(3S)-3-(3-Methoxyphenyl)piperidin-1-yl]carbonyl}-N,N-dimethylpyridin-2-amine

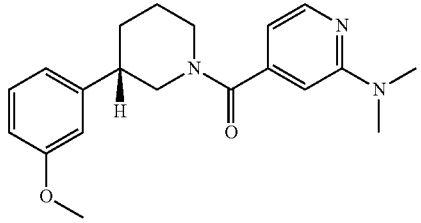 [SMILES: COc1cccc([C@@H]2CCCN(C(=O)c3ccnc(N(C)C)c3)C2)c1]

Prepared as described for 4-{[3-(2-fluorophenyl)piperidin-1-yl]carbonyl}-N,N-dimethylpyridin-2-amine (Example 1) from 2-(dimethylamino)isonicotinic acid hydrochloride and (S)-3-(3-methoxyphenyl)piperidine. The reaction product was purified via column chromatography on silica (solvent system: 0-100% ethyl acetate/petrol).

$^1$H NMR (400 MHz, CHCl$_3$-d) δ ppm 1.69-2.00 (m, 3 H) 2.09-2.19 (m, 1 H) 2.63-2.87 (m, 2 H) 2.99-3.17 (m, 7 H) 3.74-3.88 (m, 4 H) 4.76-4.88 (m, 1 H) 6.46-6.56 (m, 2 H) 6.63-6.93 (m, 3 H) 7.17-7.26 (m, 1 H) 8.16-8.26 (m, 1 H)

MS ES$^+$: 340

Example 37

N-Ethyl-N-methyl-4-{[3-(4-methylphenyl)piperidin-1-yl]carbonyl}pyridin-2-amine

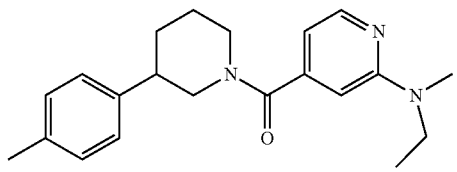

N-methylethanamine (0.030 g, 0.503 mmol) was added to a solution of 2-fluoro-4-{[3-(4-methylphenyl)piperidin-1-yl]carbonyl}pyridine (0.050 g, 0.168 mmol) (Intermediate 1a8) in THF (1 mL) and heated at 85° C. in a sealed tube for 48 hours. The crude product was purified by reverse phase preparative HPLC eluting with acetonitrile/water (with 0.1% ammonia) to afford N-ethyl-N-methyl-4-{[3-(4-methylphenyl)piperidin-1-yl]carbonyl})pyridin-2-amine (39 mg, 0.168 mmol, 65%).

$^1$H NMR (400 MHz, CHCl$_3$-d) δ ppm 1.10-1.23 (m, 3 H) 1.68-1.98 (m, 3 H) 2.06-2.16 (m, 1 H) 2.29-2.40 (m, 3 H) 2.60-2.84 (m, 2 H) 2.95-3.10 (m, 4 H) 3.54-3.66 (m, 2 H) 3.75-3.85 (m, 1 H) 4.76-4.88 (m, 1 H) 6.41-6.53 (m, 2 H) 6.98-7.05 (m, 1 H) 7.07-7.14 (m, 1 H) 7.16-7.22 (m, 2 H) 8.14-8.23 (m, 1 H)

MS ES$^+$: 338

Example 38

2-(3,3-Difluoroazetidin-1-yl)-4-{[3-(4-methylphenyl)piperidin-1-yl]carbonyl}pyridine

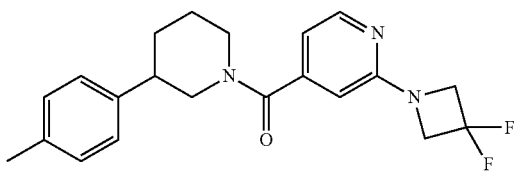 [SMILES: Cc1ccc(C2CCCN(C(=O)c3ccnc(N4CC(F)(F)C4)c3)C2)cc1]

Prepared as described for N-ethyl-N-methyl-4-{[3-(4-methylphenyl)piperidin-1-yl]carbonyl}pyridin-2-amine (Example 37) from 2-fluoro-4-{[3-(4-methylphenyl)piperidin-1-yl]carbonyl}pyridine (Intermediate 1a8) and 3,3-difluoroazetidine.

$^1$H NMR (400 MHz, CHCl$_3$-d) δ ppm 1.68-2.01 (m, 3 H) 2.07-2.17 (m, 1 H) 2.30-2.40 (m, 3 H) 2.59-2.86 (m, 2 H) 2.97-3.13 (m, 1 H) 3.66-3.78 (m, 1 H) 4.30-4.47 (m, 4 H) 4.74-4.86 (m, 1 H) 6.35-6.45 (m, 1 H) 6.67-6.74 (m, 1 H) 6.97-7.05 (m, 1 H) 7.08-7.22 (m, 3 H) 8.18-8.30 (m, 1 H)

MS ES$^+$: 372

Example 39

N-Methyl-4-{[3-(4-methylphenyl)piperidin-1-yl]carbonyl}-N-propylpyridin-2-amine

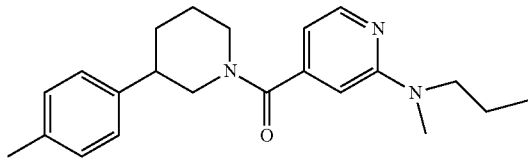 [SMILES: CCCN(C)c1cc(C(=O)N2CCCC(c3ccc(C)cc3)C2)ccn1]

Prepared as described for N-ethyl-N-methyl-4-{[3-(4-methylphenyl)piperidin-1-yl]carbonyl}pyridin-2-amine (Example 37) from 2-fluoro-4-{[3-(4-methylphenyl)piperidin-1-yl]carbonyl}pyridine (Intermediate 1a8) and N-methylpropan-1-amine.

$^1$H NMR (400 MHz, CHCl$_3$-d) δ ppm 0.88-1.02 (m, 3 H) 1.58-1.84 (m, 4 H) 1.89-2.00 (m, 1 H) 2.05-2.17 (m, 1 H) 2.27-2.40 (m, 3 H) 2.60-2.87 (m, 2 H) 2.95-3.13 (m, 4 H) 3.42-3.55 (m, 2 H) 3.72-3.84 (m, 1 H) 4.75-4.88 (m, 1 H) 6.40-6.52 (m, 2 H) 6.97-7.06 (m, 1 H) 7.07-7.23 (m, 3 H) 8.12-8.23 (m, 1 H)

MS ES$^+$: 352

Example 40

N-Methyl-4-{[3-(4-methylphenyl)piperidin-1-yl]carbonyl}-N-(propan-2-yl)pyridin-2-amine

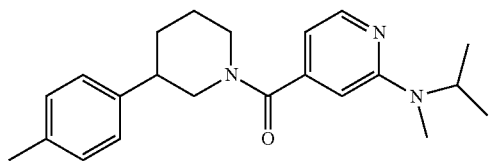 [SMILES: Cc1ccc(C2CCCN(C(=O)c3ccnc(N(C)C(C)C)c3)C2)cc1]

Prepared as described for N-ethyl-N-methyl-4-{[3-(4-methylphenyl)piperidin-1-yl]carbonyl}pyridin-2-amine (Example 37) from 2-fluoro-4-{[3-(4-methylphenyl)piperidin-1-yl]carbonyl}pyridine (Intermediate 1a8) and N-methylpropan-2-amine.

$^1$H NMR (400 MHz, CHCl$_3$-d) δ ppm 1.12-1.25 (m, 6 H) 1.61-2.00 (m, 3 H) 2.05-2.17 (m, 1 H) 2.27-2.40 (m, 3 H) 2.61-2.91 (m, 5 H) 2.94-3.11 (m, 1 H) 3.74-3.86 (m, 1 H) 4.73-4.98 (m, 2 H) 6.41-6.55 (m, 2 H) 6.97-7.05 (m, 1 H) 7.07-7.23 (m, 3 H) 8.13-8.25 (m, 1 H)

MS ES$^+$: 352

Example 41

1-(4-{[3-(4-Methylphenyl)piperidin-1-yl]carbonyl}pyridin-2-yl)azetidin-3-ol

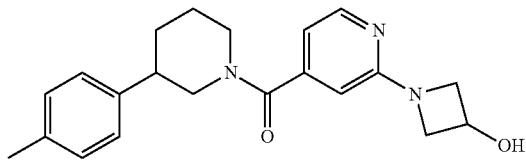 [SMILES: Cc1ccc(C2CCCN(C(=O)c3ccnc(N4CC(O)C4)c3)C2)cc1]

Prepared as described for N-ethyl-N-methyl-4-{[3-(4-methylphenyl)piperidin-1-yl]carbonyl}pyridin-2-amine (Example 37) from 2-fluoro-4-{[3-(4-methylphenyl)piperidin-1-yl]carbonyl}pyridine (Intermediate 1a8) and azetidin-3-ol.

$^1$H NMR (400 MHz, CHCl$_3$-d) δ ppm 1.65-2.00 (m, 2 H) 2.06-2.15 (m, 1 H) 2.19-2.29 (m, 1 H) 2.29-2.40 (m, 3 H) 2.59-2.85 (m, 2 H) 2.96-3.10 (m, 1 H) 3.69-3.80 (m, 1 H) 3.84-3.96 (m, 2 H) 4.26-4.39 (m, 2 H) 4.74-4.88 (m, 2 H) 6.25-6.35 (m, 1 H) 6.54-6.64 (m, 1 H) 6.98-7.06 (m, 1 H) 7.07-7.22 (m, 3 H) 8.13-8.25 (m, 1 H)

MS ES$^+$: 352

Example 42

4-{[3-(4-Chlorophenyl)piperidin-1-yl]carbonyl}-2-ethoxypyridine

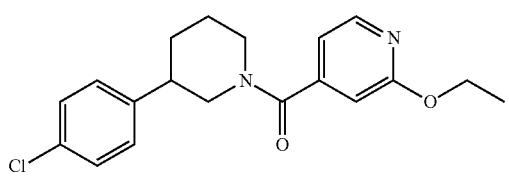 [SMILES: CCOc1cc(C(=O)N2CCCC(c3ccc(Cl)cc3)C2)ccn1]

Prepared as described for 4-{[3-(2-fluorophenyl)piperidin-1-yl]carbonyl}-N,N-dimethylpyridin-2-amine (Example 1) from 3-(4-chlorophenyl)piperidine and 2-ethoxyisonicotinic acid. The crude reaction mixture was purified by column chromatography on silica, eluting with 0-100% ethyl acetate/petrol to afford 4-{[3-(4-chlorophenyl)piperidin-1-yl]carbonyl}-2-ethoxypyridine (66 mg, 0.172 mmol, 67% yield) as a colourless gum.

$^1$H NMR (400 MHz, CHCl$_3$-d) δ ppm 1.34-1.48 (m, 3 H) 1.66-1.86 (m, 2 H) 1.89-2.02 (m, 1 H) 2.04-2.18 (m, 1 H) 2.59-2.90 (m, 2 H) 2.95-3.14 (m, 1 H) 3.65-3.78 (m, 1 H) 4.31-4.47 (m, 2 H) 4.72-4.88 (m, 1 H) 6.66-6.76 (m, 1 H) 6.80-6.90 (m, 1 H) 6.99-7.11 (m, 1 H) 7.17-7.39 (m, 3 H) 8.14-8.28 (m, 1 H)

MS ES$^+$: 345

Example 43

N-Cyclopropyl-N-methyl-4-{[3-(4-methylphenyl)piperidin-1-yl]carbonyl}pyridin-2-amine

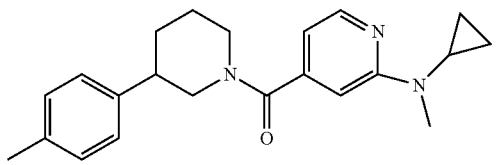 [SMILES: Cc1ccc(C2CCCN(C(=O)c3ccnc(N(C)C4CC4)c3)C2)cc1]

Prepared as described for N-ethyl-N-methyl-4-{[3-(4-methylphenyl)piperidin-1-yl]carbonyl}pyridin-2-amine (Example 37) from 2-fluoro-4-{[3-(4-methylphenyl)piperidin-1-yl]carbonyl)}pyridine (Intermediate 1a8) and N-methylcyclopropanamine.

$^1$H NMR (400 MHz, CHCl$_3$-d) δ ppm 0.62-0.74 (m, 2 H) 0.85-0.95 (m, 2 H) 1.58-1.98 (m, 3 H) 2.07-2.17 (m, 1 H) 2.30-2.40 (m, 3 H) 2.48-2.60 (m, 1 H) 2.63-2.87 (m, 2 H) 2.95-3.10 (m, 1 H) 3.12-3.24 (m, 3 H) 3.74-3.84 (m, 1 H) 4.77-4.88 (m, 1 H) 6.54-6.63 (m, 1 H) 6.91-7.05 (m, 2 H) 7.06-7.23 (m, 3 H) 8.17-8.29 (m, 1 H)

MS ES$^+$: 350

Example 44

N,N-Dimethyl-4-({3-[4-(trifluoromethyl)phenyl]piperidin-1-yl}carbonyl)pyridin-2-amine formate

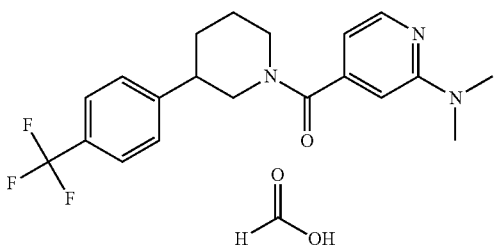

A solution of propylphosphonic anhydride (50% in EtOAc, 0.96 g, 0.89 mL, 1.50 mmol) was added to a solution of 3-[4-(trifluoromethyl)phenyl]piperidine hydrochloride (0.19 g, 0.75 mmol) (Intermediate 1a14) triethylamine (0.23 g, 0.31 mL, 2.23 mmol) and 2-dimethyl aminoisonicotinic acid (0.15 g, 0.90 mmol) in DCM (3 mL). The reaction mixture was stirred at room temperature overnight. Aqueous sodium bicarbonate solution (5 mL) was added and extracted with DCM (3×10 mL). The organic layer was dried (Na$_2$SO$_4$) and concentrated in vacuo. The resulting mixture was purified with reverse phase HPLC using acetonitrile/water and formic acid buffer. This yielded the title compound (98.0 mg, 31% yield) as a colourless oil.

$^1$H NMR (400 MHz, DMSO-d$_6$) δ ppm 1.45-2.01 (m, 4 H) 2.67-2.9 (m, 1 H) 3.00 (s, 3 H) 3.04 (s, 3 H) 3.05-3.55 (m, 3 H) 4.49-4.55 (m, 1 H) 6.51-6.56 (m, 2 H) 7.41-7.72 (m, 4 H) 8.09-8.15 (m, 2 H)

MS ES$^+$: 378

Example 45

N,N-Dimethyl-4-({3-[2-(trifluoromethyl)phenyl]piperidin-1-yl}carbonyl)pyridin-2-amine

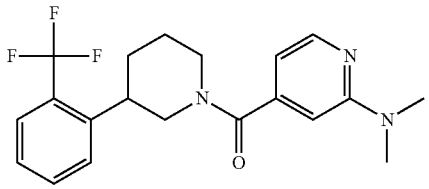 [SMILES: CN(C)c1cc(C(=O)N2CCCC(c3ccccc3C(F)(F)F)C2)ccn1]

A solution of propylphosphonic anhydride (50% in EtOAc, 0.96 g, 0.89 mL, 1.50 mmol) was added to a solution of 3-[2-(trifluoromethyl)phenyl]piperidine hydrochloride (0.19 g, 0.75 mmol) (Intermediate 1a15), triethylamine (0.23 g, 0.31 mL, 2.23 mmol) and 2-(dimethylamino)isonicotinic acid (0.15 g, 0.90 mmol) in DCM (3 mL). The reaction mixture was stirred at ambient temperature overnight. Aqueous sodium bicarbonate solution (5 mL) was added and extracted with DCM (3×10 mL). The organic layer was dried (Na$_2$SO$_4$) and concentrated in vacuo. The resulting mixture was purified with reverse phase HPLC using acetonitrile/water and formic acid buffer. This yielded the title compound (52.0 mg, 16% yield) as a colourless oil.

$^1$H NMR (400 MHz, DMSO-d$_6$) δ ppm 1.52-1.88 (m, 4 H) 2.85-3.65 (m, 4 H) 2.95 (s, 3 H) 3.02 (s, 3 H) 4.45-4.57 (m, 1 H) 6.37-6.54 (m, 2 H) 7.36-7.75 (m, 4 H) 8.02-8.12 (m, 2 H)

MS ES$^+$: 378

Example 46

4-{[3-(2-Chlorophenyl)piperidin-1-yl]carbonyl}-N,N-dimethylpyridin-2-amine

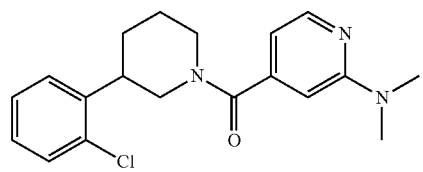 [SMILES: CN(C)c1cc(C(=O)N2CCCC(c3ccccc3Cl)C2)ccn1]

Prepared as described for 4-{[3-(2-fluorophenyl)piperidin-1-yl]carbonyl}-N,N-dimethylpyridin-2-amine (Example 1) from 2-(dimethylamino)isonicotinic acid and 3-(2-chlorophenyl)piperidine hydrochloride (Intermediate 1a16).

$^1$H NMR (400 MHz, DCM-d$_2$) δ ppm 1.33-2.20 (m, 6 H) 2.69-3.41 (m, 7 H) 3.76-3.80 (m, 1 H) 4.67-4.89 (m, 1 H) 6.56 (s, 2 H) 7.12-7.51 (m, 4 H) 8.08-8.26 (m, 1 H)

MS ES$^+$: 344

Example 47

4-{[3-(4-Methoxyphenyl)piperidin-1-yl]carbonyl}-N,N-dimethylpyridin-2-amine

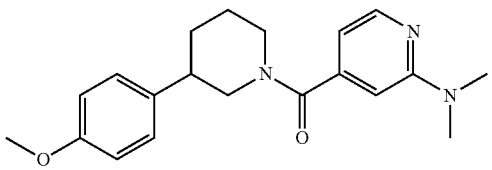

To a stirred solution of 2-(dimethylamino)isonicotinic acid hydrochloride (106 mg, 0.523 mmol) in DCM (2 mL) was added 3-(4-methoxyphenyl)piperidine (Intermediate 1a17—as free base) (100 mg, 0.523 mmol), triethylamine (0.146 mL, 1.046 mmol) and propylphosphonic anhydride (0.616 mL, 1.046 mmol). After 2 hours the reaction was quenched by addition of saturated aqueous NaHCO$_3$ (2 mL), diluted in ethyl acetate (15 mL) and washed with water (2×5 mL) then brine (5 mL). The crude product was purified by reverse phase preparative HPLC eluting with acetonitrile/water (with 0.1% ammonia) to afford 4-{[3-(4-methoxyphenyl)piperidin-1-yl]carbonyl}-N,N-dimethylpyridin-2-amine (90.2 mg, 0.252 mmol, 48% yield) as a solid.

$^1$H NMR (400 MHz, DMSO-d$_6$) δ ppm 1.44-1.95 (m, 4 H) 2.63-2.82 (m, 2 H) 2.97-3.08 (m, 7 H) 3.38-3.58 (m, 1 H) 3.65-3.77 (m, 3 H) 4.42-4.57 (m, 1 H) 6.46-6.58 (m, 2 H) 6.77-6.97 (m, 2 H) 7.01-7.12 (m, 1 H) 7.19-7.26 (m, 1 H) 8.07-8.17 (m, 1 H)

MS ES$^+$: 340

Example 48

4-{[3-(2-Methoxyphenyl)piperidin-1-yl]carbonyl}-N,N-dimethylpyridin-2-amine

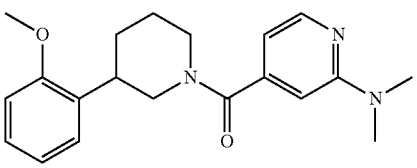 [SMILES: COc1ccccc1C1CCCN(C(=O)c2ccnc(N(C)C)c2)C1]

To a stirred suspension of 2-(dimethylamino)isonicotinic acid hydrochloride (0.1 g, 0.493 mmol) and 3-(2-methoxyphenyl)piperidine hydrochloride (Intermediate 1a 18) (0.112 g, 0.493 mmol) in DCM (2 ml) was added triethylamine (0.206 ml, 1.480 mmol) then propylphosphonic anhydride (0.727 ml, 1,234 mmol). The reaction mixture was stirred at ambient temperature overnight. The reaction was diluted with EtOAc (20 ml) and washed with saturated (aq.) NaHCO$_3$ (2×10 ml) then brine (10 ml). The crude product was purified by reverse phase preparative HPLC eluted with acetonitrile/water (with 0.1% ammonia) and lyophilised to afford 4-{[3-(2-methoxyphenyl)piperidin-1-yl]carbonyl}-N,N-dimethylpyridin-2-amine (10.6 mg, 0.031 mmol, 6% yield) as a solid.

$^1$H NMR (400 MHz, MeCN-d$_3$) δ ppm 1.51-1.91 (m, 4 H) 2.69-2.93 (m, 2 H) 3.02-3.09 (m, 7 H) 3.56-3.87 (m, 4 H) 4.55-4.65 (m, 1 H) 6.44-6.54 (m, 2 H) 6.80-7.02 (m, 2 H) 7.11-7.30 (m, 2 H) 8.08-8.16 (m, 1 H)

MS ES$^+$: 340

Example 49

N,N-Dimethyl-4-{[3-(4-methylphenyl)piperidin-1-yl]carbonyl}pyridin-2-amine

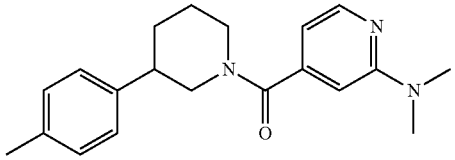

Prepared as described for 4-{[3-(2-fluorophenyl)piperidin-1-yl]carbonyl}-N,N-dimethylpyridin-2-amine (Example 1) from 2-(dimethylamino)isonicotinic acid and 3-(4-methylphenyl)piperidine hydrochloride. The crude product was purified by column chromatography on basic silica, eluting with 0-60% ethyl acetate/petrol to afford N,N-dimethyl-4-{[3-(4-methylphenyl)piperidin-1-yl]carbonyl}pyridin-2-amine (9 mg, 59%) as a solid.

$^1$H NMR (400 MHz. MeOH-d$_4$) δ ppm 1.54-2.12 (m, 4 H) 2.23-2.38 (m, 3 H) 2.68-2.96 (m, 2 H) 3.04-3.23 (m, 7 H) 3.60-3.76 (m, 1 H) 4.59-4.72 (m, 1 H) 6.52-6.65 (m, 2 H) 6.99-7.11 (m, 2 H) 7.12-7.25 (m, 2 H) 8.09-8.19 (m, 1 H)

MS ES$^+$: 324

Examples 50 and 51

N,N-Dimethyl-4-{[3-(4-methylphenyl)piperidin-1-yl]carbonyl}pyridin-2-amine (enantiomers)

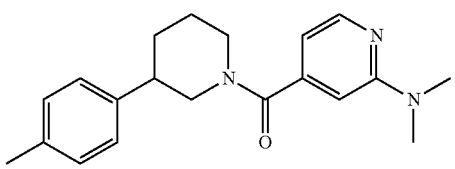

Racemic N,N-dimethyl-4-{[3-(4-methylphenyl)piperidin-1-yl]carbonyl}pyridin-2-amine (Example 49, 20 mg, 0.062 mmol) was separated by chiral liquid chromatography using a Chiralpak AD column and 10% EtOH in heptane (Isocratic) as solvent to give Enantiomer 1 (Rt=15.8 mins) and Enantiomer 2 (Rt=18.1 mins).

Example 50 (Enantiomer 1)

MS ES$^+$: 324

Chiral SFC (Jasco) Chiralpak AD-H (4.6×100 mm, 51 μm Daicel); 100 mbar CO$_2$ with 16%
EtOH; 40° C.; Rt=6.27 mins.

Example 51 (Enantiomer 2)

MS ES$^+$: 324

Chiral SFC (Jasco) Chiralpak AD-H (4.6×100 mm, 5 μm Daicel); 100 mbar CO$_2$ with 16% EtOH; 40° C.; Rt=7.23 mins.

Example 52

4-{[3-(4-Chlorophenyl)piperidin-1-yl]carbonyl}-2-ethylpyridine

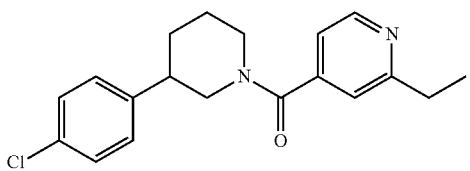 [SMILES: CCc1cc(C(=O)N2CCCC(c3ccc(Cl)cc3)C2)ccn1]

Prepared as described for 4-{[3-(2-fluorophenyl)piperidin-1-yl]carbonyl}-N,N-dimethylpyridin-2-amine (Example 1) from 2-ethylisonicotinic acid and 3-(4-chlorophenyl)piperidine.

$^1$H NMR (DCM-d$_2$) δ ppm 1.26-1.43 (m, 3 H) 1.53-2.15 (m, 4 H) 2.61-3.13 (m, 5 H) 3.55-3.70 (m, 1 H) 4.68-4.70 (m, 1 H) 7.06-7.41 (m, 6 H) 8.55-8.65 (m, 1 H)

MS ES$^+$: 329

Example 53

N-Methyl-4-({3-[4-(trifluoromethyl)phenyl]piperidin-1-yl}carbonyl)pyridin-2-amine

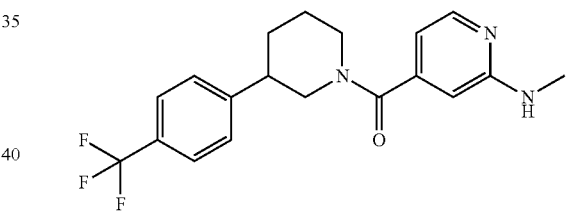

A solution of propylphosphonic anhydride (50 wt % in EtOAc, 0.760 mL), 2-(methylamino)isonicotinic acid hydrochloride hemi hydrate (50 mg, 0.253 mmol) and triethylamine (0.106 mL, 0.759 mmol) in DCM (2 mL) was added to 3-[4-(trifluoromethyl)phenyl]piperidine hydrochloride (Intermediate 1a14) (0.067 g, 0.253 mmol). The reaction was stirred at ambient temperature for 23 hours, then quenched by addition of saturated (aq.) NaHCO$_3$ (5 mL) with vigorous stirring for 15 mins. The reaction was diluted in DCM (5 mL) and the phases separated. The aqueous was extracted with DCM (5 mL). The combined organics were reduced in vacuo and purified by reverse phase preparative HPLC (ACN/Water+0.1% formic acid) to afford N-methyl-4-({3-[4-(trifluoromethyl)phenyl]piperidin-1-yl}carbonyl)pyridin-2-amine(10 mg, 0.253 mmol, 11%) as a solid.

$^1$H NMR (400 MHz, CHCl$_3$-d) δ ppm 1.48-2.23 (m, 4 H) 2.66-3.17 (m, 6 H) 3.68-3.89 (m, 1 H) 4.68-4.91 (m, 1 H) 5.15 (br. s, 1 H) 6.28-6.62 (m, 2 H) 7.16-7.28 (m, 1H) 7.34-7.70 (m, 3 H) 8.00-8.21 (m, 1 H)

MS ES$^+$: 364

Example 54

N-Methyl-4-({3-[2-(trifluoromethyl)phenyl]piperidin-1-yl}carbonyl)pyridin-2-amine

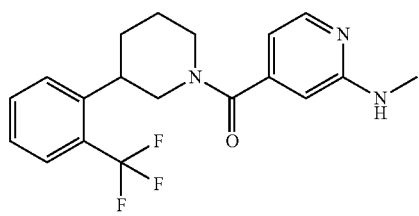 [SMILES: CNc1cc(C(=O)N2CCCC(c3ccccc3C(F)(F)F)C2)ccn1]

Prepared as described for N-methyl-4-({3-[4-(trifluoromethyl)phenyl]piperidin-1-yl}carbonyl)pyridin-2-amine (Example 53) from 2-(methylamino)isonicotinic acid hydrochloride hemi hydrate and 3-[2-(trifluoromethyl)phenyl]piperidine hydrochloride (Intermediate 1a15).

$^1$H NMR (400 MHz, CHCl$_3$-d) δ ppm 1.65-2.17 (m, 4 H) 2.68-3.26 (m, 6 H) 3.64-3.89 (m, 1 H) 4.74-4.94 (m, 1 H) 5.15 (br. s, 1 H) 6.28-6.65 (m, 2 H) 7.30-7.78 (m, 4 H) 7.94-8.20 (m, 1 H)

MS ES$^+$: 364

Example 55

4-{[3-(4-Methoxyphenyl)piperidin-1-yl]carbonyl}-N-methylpyridin-2-amine hemi formate

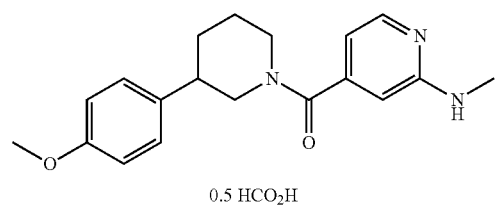

0.5 HCO$_2$H

Prepared as described for N-methyl-4-({3-[4-(trifluoromethyl)phenyl]piperidin-1-yl}carbonyl)pyridin-2-amine (Example 53) from 2-(methylamino)isonicotinic acid hydrochloride hemi hydrate and 3-(4-methyoxyphenyl)piperidine hydrochloride (Intermediate 1a17) except purified by reverse phase prep HPLC (ACN/Water+0.1% formic acid) to give the hemi formate salt.

$^1$H NMR (400 MHz, CHCl$_3$-d) δ ppm 1.63-2.23 (m, 4 H) 2.69-3.13 (m, 6 H) 3.61-3.89 (m, 4 H) 4.67-4.88 (m, 1 H) 5.70 (br. s, 1 H) 6.31-6.63 (m, 2 H) 6.75-6.94 (m, 2 H) 6.97-7.10 (m, 1 H) 7.14-7.26 (m, 1 H) 7.95-8.16 (m, 1 H) 8.35 (s, 0.5H, hemi-formate)

MS ES$^+$: 326

Example 56

4-{[3-(2-Methoxyphenyl)piperidin-1-yl]carbonyl}-N-methylpyridin-2-amine

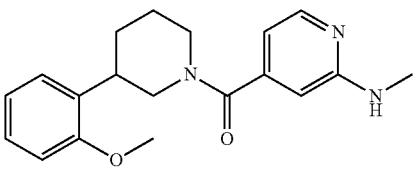 [SMILES: CNc1cc(C(=O)N2CCCC(c3ccccc3OC)C2)ccn1]

Prepared as described for N-methyl-4-({3-[4-(trifluoromethyl)phenyl]piperidin-1-yl}carbonyl)pyridin-2-amine (Example 53) from 2-(methylamino)isonicotinic acid hydrochloride hemi hydrate and 3-(2-methoxyphenyl)piperidine hydrochloride (Intermediate 1a18).

$^1$H NMR (400 MHz, CHCl$_3$-d) δ ppm 1.51-2.16 (m, 4 H) 2.68-3.33 (m, 6 H) 3.58-3.98 (m, 4 H) 4.66-4.89 (m, 1 H) 5.30 (br. s, 1 H) 6.34-6.49 (m, 1 H) 6.53-6.67 (m, 1 H) 6.72-7.02 (m, 2 H) 7.07-7.27 (m, 2 H) 7.96-8.18 (m, 1 H)

MS ES$^+$: 326

Example 57

4-({3-[4-Chloro-2-(trifluoromethyl)phenyl]piperidin-1-yl}carbonyl)-N-methylpyridin-2-amine

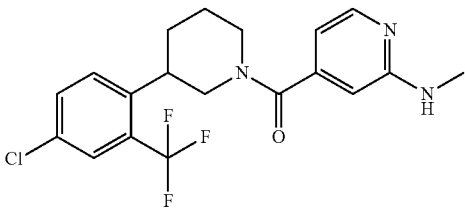 [SMILES: CNc1cc(C(=O)N2CCCC(c3ccc(Cl)cc3C(F)(F)F)C2)ccn1]

3-[4-chloro-2-(trifluoromethyl)phenyl]piperidine hydrochloride (50 mg, 0.167 mmol) (Intermediate 1a6) was dissolved in DCM (5 mL) at room temperature and 2-(methylamino)isonicotinic acid, hydrogen chloride (47.1 mg, 0.250 mmol) was added, followed by propylphosphonic anhydride (50% wt solution in ethyl acetate) (0.106 mL, 0.167 mmol) and triethylamine (0.023 mL, 0.167 mmol). The mixture was stirred at room temperature for 17 hours. Water was added to the reaction mixture which was stirred vigorously for 30 minutes before the phases were separated using a phase separator cartridge. The organics were concentrated in vacuo and the crude product was purified by reverse phase preparative HPLC eluting with acetonitrile/water (with 0.1% ammonia) to afford 4-({3-[4-chloro-2-(trifluoromethyl)phenyl]piperidin-1-yl}carbonyl)-N-methylpyridin-2-amine (35 mg, 0.09 mmol, 53% yield).

$^1$H NMR (400 MHz, DMSO-d$_6$) δ ppm 1.51 (br. s., 1 H) 1.65-1.97 (m, 3 H) 2.62-3.30 (m, 6 H) 3.38-3.65 (m, 1 H) 4.36-4.58 (m, 1 H) 6.19-6.72 (m, 3 H) 7.60-8.12 (m, 4 H)

MS ES$^+$: 398

Example 58

2-Ethyl-4-({3-[2-(trifluoromethyl)phenyl]piperidin-1-yl}carbonyl)pyridine

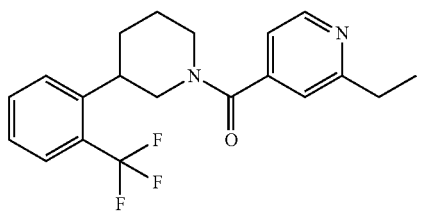 [SMILES: CCc1cc(C(=O)N2CCCC(c3ccccc3C(F)(F)F)C2)ccn1]

Prepared as described for N-methyl-4-({3-[4-(trifluoromethyl)phenyl]piperidin-1-yl}carbonyl)pyridin-2-amine (Example 53) from 2-ethylisonicotinic acid and 3-[2-(trifluoromethyl)phenyl]piperidine hydrochloride (Intermediate 1a15).

$^1$H NMR (400 MHz, DMSO-$d_6$) δ ppm 1.01-1.34 (m, 3 H) 1.48-2.00 (m, 4 H) 2.61-3.07 (m, 4 H) 3.18-3.51 (m, 2 H) 4.43-4.64 (m, 1 H) 6.96-7.85 (m, 6 H) 8.37-8.62 (m, 1 H)

MS ES$^+$: 363

Example 59

2-Ethyl-4-{[3-(2-methoxyphenyl)piperidin-1-yl]carbonyl}pyridine

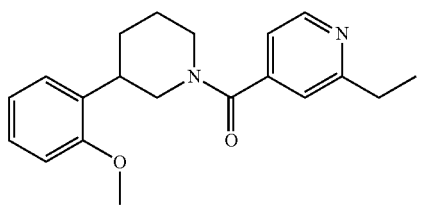 [SMILES: CCc1cc(C(=O)N2CCCC(c3ccccc3OC)C2)ccn1]

Prepared as described for N-methyl-4-({3-[4-(trifluoromethyl)phenyl]piperidin-1-yl}carbonyl)pyridin-2-amine (Example 53) from 2-ethylisonicotinic acid and 3-(2-methoxyphenyl)piperidine hydrochloride (the hydrochloride salt of Intermediate 1a18).

$^1$H NMR (400 MHz, DMSO-$d_6$) δ ppm 1.09-1.35 (m, 3 H) 1.45-1.98 (m, 4 H) 2.68-3.89 (m, 9 H) 4.37-4.64 (m, 1 H) 6.78-7.33 (m, 6 H) 8.57 (d, J=5.05 Hz, 1 H)

MS ES$^+$: 325

Example 60

N,N-Dimethyl-4-({3-[2-(trifluoromethoxy)phenyl]piperidin-1-yl}carbonyl)pyridin-2-amine

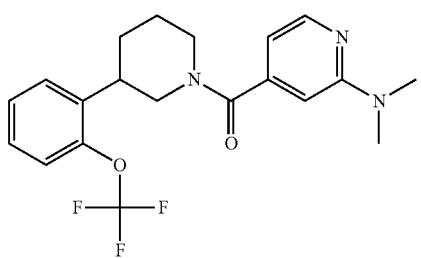 [SMILES: CN(C)c1cc(C(=O)N2CCCC(c3ccccc3OC(F)(F)F)C2)ccn1]

A solution of 1-propylphosphonic acid cyclic anhydride (50% in EtOAc, 10.6 mL, 1.06 mmol) was added to a solution of 3-[2-(trifluoromethoxy)phenyl]piperidine hydrochloride (0.150 g, 0.532 mmol) (Intermediate 1a19), triethylamine (0.148 mL, 1.06 mmol) and 2-(dimethylamino)isonicotinic acid (0.106 g, 0.639 mmol) in DCM (3 mL). The reaction was stirred at room temperature for 24 hours. The mixture was partitioned between DCM and saturated aqueous NaHCO$_3$. The phases were separated and the aqueous extracted with DCM (3×10 mL), dried (Na$_2$SO$_4$) and concentrated in vacuo. The crude product was purified by reverse phase preparative HPLC eluting with acetonitrile/water (with 0.1% formic acid) to afford N,N-dimethyl-4-({3-[2-(trifluoromethoxy)phenyl]piperidin-1-yl}carbonyl)pyridin-2-amine (55 mg, 0.140 mmol, 26%) as a colourless oil.

$^1$H NMR (400 MHz, CHCl$_3$-d) δ ppm 1.10-2.00 (m, 4 H) 2.6-3.2 (m, 9 H) 3.5-3.7 (m, 1 H) 4.6-4.8 (m, 1 H) 6.44-6.59 (m, 2 H) 7.2-7.4 (m, 4 H) 8.08-8.13 (m, 1 H)

MS ES$^+$: 394

Example 61

4-{[3-(4-Chloro-2-ethoxyphenyl)piperidin-1-yl]carbonyl}-N,N-dimethylpyridin-2-amine

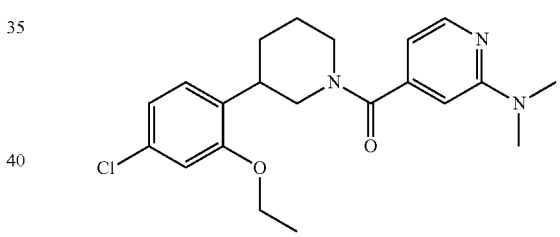

A solution of 1-propylphosphonic acid cyclic anhydride (50% in EtOAc, 10.6 mL, 1.06 mmol) was added to a solution of 3-(4-chloro-2-ethoxyphenyl)piperidine hydrochloride (0.150 g, 0.626 mmol) (Intermediate 1a20), triethylamine (0.17 mL, 1.25 mmol) and 2-(dimethylamino)isonicotinic acid (0.125 g, 0.751 mmol) in DCM (3 mL). The reaction was stirred at room temperature for 24 hours. The mixture was partitioned between DCM and saturated aqueous NaHCO$_3$. The phases were separated and the aqueous phase was extracted with DCM (3×10 mL), dried (Na$_2$SO$_4$) and concentrated in vacuo. The crude product was purified by reverse phase preparative HPLC, eluting with acetonitrile/water (with 0.1% formic acid) to afford 4-{[3-(4-chloro-2-ethoxyphenyl)piperidin-1-yl]carbonyl}-N,N-dimethylpyridin-2-amine (0.069 g, 0.178 mmol, 29%).

$^1$H NMR (400 MHz, CHCl$_3$-d) δ ppm 1.15-1.97 (m, 6 H) 2.89-3.13 (m, 12 H) 3.58-3.67 (m, 1 H) 4.68-4.75 (m, 1 H) 6.19-6.51 (m, 2 H) 6.93-7.19 (m, 3 H) 8.09-8.17 (m, 1 H)

MS ES$^+$: 388

Example 62

4-({3-[4-Methoxy-2-(trifluoromethyl)phenyl]piperidin-1-yl}carbonyl)-N,N-dimethylpyridin-2-amine

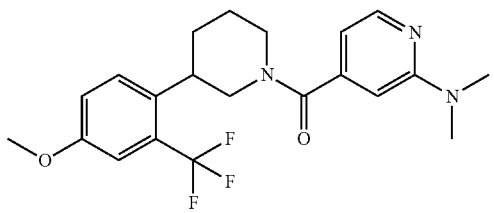

Prepared as described for N-methyl-4-({3-[4-(trifluoromethyl)phenyl]piperidin-1-yl}carbonyl)pyridin-2-amine(Example 53) from 2-(dimethylamino)isonicotinic acid hydrochloride and 3-[4-methoxy-2-(trifluoromethyl)phenyl]piperidine hydrochloride (Intermediate 1a21).

$^1$H NMR (400 MHz, DMSO-d$_6$) δ ppm 1.35-1.95 (m, 4 H) 2.72-3.62 (m, 10 H) 3.70-3.90 (m, 3 H) 4.39-4.61 (m, 1 H) 6.32-6.64 (m, 2 H) 7.01-7.30 (m, 2 H) 7.47-7.73 (m, 1 H) 7.98-8.19 (m, 1 H)

MS ES$^+$: 408

Example 63

4-{[3-(4-Methoxy-2-methylphenyl)piperidin-1-yl]carbonyl}-N-methylpyridin-2-amine

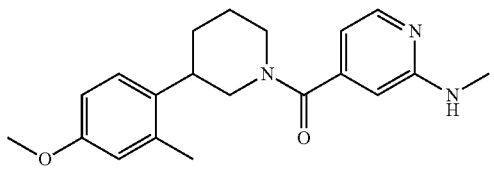

Prepared as described N-methyl-4-({3-[4-(trifluoromethyl)phenyl]piperidin-1-yl}carbonyl)pyridin-2-amine (Example 53) from 3-(4-methoxy-2-methylphenyl)piperidine (Intermediate 1a22) and 2-(methylamino)isonicotinic acid hydrochloride.

$^1$H NMR (400 MHz, MeCN-d$_3$) δ ppm 1.40-2.03 (m, 4 H) 2.05-2.25 (m, 3 H) 2.57-3.16 (m, 6 H) 3.36-3.86 (m, 4 H) 4.45-4.73 (m, 1 H) 5.14-5.36 (m, 1 H) 6.25-6.60 (m, 2 H) 6.64-6.87 (m, 2 H) 7.00-7.30 (m, 1 H) 7.91-8.17 (m, 1 H)

MS ES$^+$: 340

Example 64

4-({3-[4-Methoxy-2-(trifluoromethyl)phenyl]piperidin-1-yl}carbonyl)-N-methylpyridin-2-amine formate

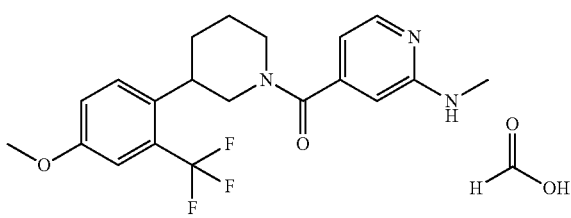

Prepared as described for N-methyl-4-({3-[4-(trifluoromethyl)phenyl]piperidin-1-yl}carbonyl)pyridin-2-amine (Example 53) from 2-(methylamino)isonicotinic acid hydrochloride and 3-[4-methoxy-2-(trifluoromethyl)phenyl]piperidine hydrochloride (Intermediate 1a21). The reaction product was purified by reverse phase preparative HPLC eluting with acetonitrile/water (with 0.1% ammonia). This was repeated a second time but using instead, as the eluant, acetonitrile/water (with 0.1% formic acid) to afford 4-({3-[4-methoxy-2-(trifluoromethyl)phenyl]piperidin-1-yl}carbonyl)-N-methylpyridin-2-amine formate (12.3 mg, 0.028 mmol, 9.63% yield) as a solid.

$^1$H NMR (400 MHz. MeCN-d$_3$) δ ppm 1.42-2.11 (m, 4 H) 2.88 (br. S., 3 H) 2.95-3.20 (m, 2 H) 3.31 (s, 1 H) 3.43-3.71 (m, 1 H) 3.73-3.95 (m, 3 H) 4.44-4.73 (m, 1 H) 5.50 (br. s, 1H) 6.29-6.62 (m, 2 H) 7.03-7.32 (m, 2 H) 7.33-7.63 (m, 1 H) 7.90-8.20 (m, 1 H) 8.13 (s, 1 H, formate)

MS ES$^+$: 394

Example 65

4-{[3-(4-Chloro-2-ethoxyphenyl)piperidin-1-yl]carbonyl}-N-methylpyridin-2-amine

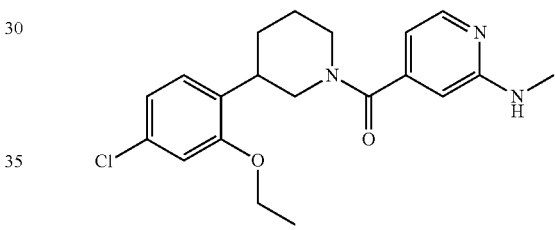

To a stirred solution of 2-(methylamino)isonicotinic acid hydrochloride (63.2 mg, 0.320 mmol), 3-(4-chloro-2-ethoxyphenyl)piperidine hydrochloride (80 mg, 0.291 mmol) (Intermediate 1a20) and triethylamine (0.081 mL, 0.582 mmol) in DCM (4 mL) was added propylphosphonic anhydride (0.257 mL, 0.436 mmol). In a separate flask additional 2-(methylamino)isonicotinic acid hydrochloride (57.5 mg, 0.291 mmol) in DCM (0.5 mL) was incubated with triethylamine (0.040 mL, 0.291 mmol, 1 eq.) and propylphosphonic anhydride (0.257 mL, 0.436 mmol, 1.5 eq). After 10 minutes the solution was added to the reaction mixture. Further 2-(methylamino)isonicotinic acid hydrochloride (57 mg. 0.29 mmol, 1 eq) and EDC (55.7 mg, 0.291 mmol) were added. After 17 hours the reaction was quenched with saturated (aq.) NaHCO$_3$ (2 mL) then diluted with EtOAc (20 mL) and washed with saturated aqueous) NaHCO$_3$ (2×5 mL). The reaction mixture was concentrated in vacuo and the crude product was purified twice by reverse phase preparative HPLC eluting with acetonitrile/water (with 0.1% ammonia) to give 4-{[3-(4-chloro-2-ethoxyphenyl)piperidin-1-yl]carbonyl}-N-methylpyridin-2-amine (10 mg, 0.025 mmol, 9% yield) as a solid.

$^1$H NMR (400 MHz, MeCN-d$_3$) δ ppm 1.13-2.02 (m, 7 H) 2.65-3.35 (m, 6 H) 3.56-3.78 (m, 1 H) 3.84-4.17 (m, 2 H) 4.43-4.70 (m, 1 H) 5.16-5.40 (m, 1 H) 6.26-6.58 (m, 2 H) 6.79-7.07 (m, 2 H) 7.10-7.33 (m, 1 H) 8.01-8.12 (m, 1 H)

MS ES$^+$: 374

Example 66

4-({3-[2-(Difluoromethoxy)phenyl]piperidin-1-yl}carbonyl)-N,N-dimethylpyridin-2-amine

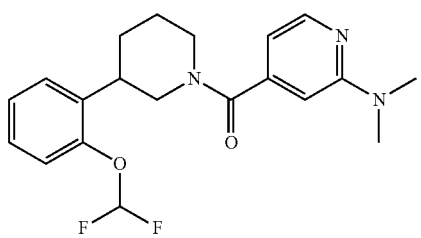 [SMILES: CN(C)c1cc(C(=O)N2CCCC(c3ccccc3OC(F)F)C2)ccn1]

A solution of 1-propylphosphonic acid cyclic anhydride (50% in EtOAc, 0.67 mL, 1.13 mmol) was added to a solution of 3-[2-(difluoromethoxy)phenyl]piperidine hydrochloride (0.150 g, 0.568 mmol) (Intermediate 1a23), triethylamine (0.159 mL, 1.13 mmol) and 2-(dimethylamino)isonicotinic acid (0.113 g, 0.683 mmol) in DCM (3 mL). The reaction was stirred at room temperature for 24 hours. The mixture was partitioned between DCM and saturated aqueous NaHCO₃. The phases were separated and the aqueous phase was extracted with DCM (3×10 mL), dried (Na₂SO₄) and concentrated in vacuo. The crude product was purified by reverse phase preparative HPLC eluting with acetonitrile/water (with 0.1% formic acid) to afford 4-({3-[2-(difluoromethoxy)phenyl]piperidin-1-yl}carbonyl)-N,N-dimethylpyridin-2-amine (58 mg, 0.140 mmol, 27%) as a colourless gum.

$^1$H NMR (CHCl₃-d) δ ppm 1.59-2.02 (m, 4 H) 2.72-3.24 (m, 9 H) 3.61-3.71 (m, 1 H) 4.74-4.78 (m, 1 H) 6.56-6.64 (m, 3 H) 6.95-7.30 (m, 4 H), 8.16 (m, 1 H)

MS ES⁺: 376

Example 67

2-(1-{[2-(Dimethylamino)pyridin-4-yl]carbonyl}piperidin-3-yl)benzonitrile

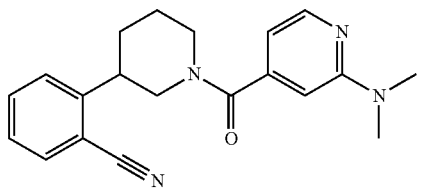 [SMILES: CN(C)c1cc(C(=O)N2CCCC(c3ccccc3C#N)C2)ccn1]

A solution of 1-propylphosphonic acid cyclic anhydride (50% in EtOAc, 0.32 mL, 0.556 mmol) was added to a solution of 2-(piperidin-3-yl)benzonitrile hydrochloride (0.062 g, 0.278 mmol) (Intermediate 1a24), triethylamine (0.078 mL, 0.556 mmol) and 2-(dimethylamino)isonicotinic acid (0.055 g, 0.330 mmol) in DCM (2 mL). The reaction was stirred at room temperature for 24 hours. The mixture was partitioned between DCM and saturated aqueous NaHCO₃. The phases were separated and the aqueous phase was extracted with DCM (3×10 mL), dried (Na₂SO₄) and concentrated in vacuo. The crude product was purified by reverse phase preparative HPLC eluting with acetonitrile/water (with 0.1% formic acid) to afford 2-(1-{[2-(dimethylamino)pyridin-4-yl]carbonyl}piperidin-3-yl)benzonitrile (37 mg, 0.140 mmol, 40%) as a foam.

$^1$H NMR (CHCl₃-d) δ ppm 1.76-2.15 (m, 4 H) 2.60-2.77 (m, 1 H) 3.01-3.18 (m, 8 H) 3.6-3.8 (m, 1 H) 4.79-4.88 (m, 1 H) 6.5-6.7 (m, 2 H) 7.20-7.40 (m, 2 H) 7.57-7.59 (m, 2H) 8.17-8.21 (m, 1H)

MS ES⁺: 335

Example 68

4-{[3-(4-Chloro-2,6-dimethylphenyl)piperidin-1-yl]carbonyl}-N,N-dimethylpyridin-2-amine

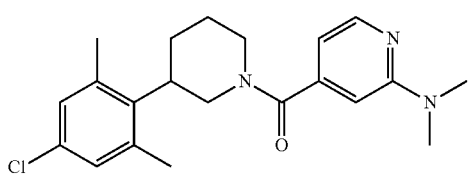 [SMILES: Cc1cc(Cl)cc(C)c1C1CCCN(C(=O)c2ccnc(N(C)C)c2)C1]

A solution of 1-propylphosphonic acid cyclic anhydride (50% in EtOAc, 0.34 mL, 0.580 mmol) was added to a solution of 3-(4-chloro-2,6-dimethylphenyl)piperidine hydrochloride (0.065 g, 0.291 mmol) (Intermediate 1a25), triethylamine (0.058 mL, 0.580 mmol) and 2-(dimethylamino)isonicotinic acid (0.058 g, 0.349 mmol) in DCM (2 mL). The reaction was stirred at room temperature for 24 hours. The mixture was partitioned between DCM and saturated aqueous NaHCO₃. The phases were separated and the aqueous phase was extracted with DCM (3×10 mL), dried (Na₂SO₄) and concentrated in vacuo. The crude product was purified by reverse phase preparative HPLC eluting with acetonitrile/water (with 0.1% formic acid) to afford 4-{[3-(4-chloro-2,6-dimethylphenyl)piperidin-1-yl]carbonyl}-N,N-dimethylpyridin-2-amine (32 mg, 0.140 mmol, 28%) as a foam.

$^1$H NMR (CHCl₃-d) δ ppm 1.78-2.11 (m, 4 H), 2.14 (s, 6 H), 2.54-2.69 (m, 1 H), 3.18 (s, 6 H), 3.48-3.62 (m, 2 H), 4.53-4.71 (m, 2 H), 6.47-6.59 (m, 2 H), 6.80-6.87 (m, 2 H), 8.10-8.17 (m, 1 H).

MS ES⁺: 372

Example 69

5-{[3-(4-Chlorophenyl)piperidin-1-yl]carbonyl}-N,N-dimethylpyridazin-3-amine

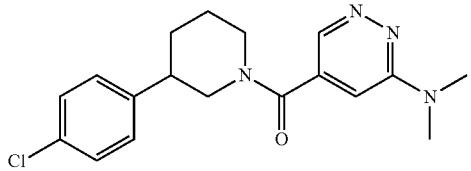 [SMILES: CN(C)c1cc(C(=O)N2CCCC(c3ccc(Cl)cc3)C2)cnn1]

Prepared as described for 4-{[3-(2-fluorophenyl)piperidin-1-yl]carbonyl}-N,N-dimethylpyridin-2-amine (Example 1) from 3-(4-chlorophenyl)piperidine and 6-(dimethylamino)pyridazine-4-carboxylic acid (Intermediate 1b1) in suspension (DMF). Purification was carried out via silica column chromatography (solvent system: 0-100% ethyl acetate/petrol).

¹H NMR (400 MHz, CHCl₃-d) δ ppm 1.61-2.19 (m, 4 H) 2.69-2.89 (m, 1 H) 3.01-3.30 (m, 8 H) 3.63-3.77 (m, 1 H) 4.73-4.86 (m, 1 H) 6.73-6.84 (m, 1 H) 7.01-7.11 (m, 1 H) 7.19-7.39 (m, 3 H) 8.54 (s, 1 H)

MS ES⁺: 345

Example 70

5-{[3-(4-Chloro-2-methylphenyl)piperidin-1-yl]carbonyl}-N,N-dimethylpyridazin-3-amine

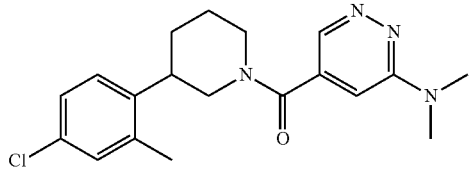 [SMILES: Cc1cc(Cl)ccc1C1CCCN(C(=O)c2cnnc(N(C)C)c2)C1]

Prepared as described for 4-{[3-(2-fluorophenyl)piperidin-1-yl]carbonyl}-N,N-dimethylpyridin-2-amine (Example 1) from 3-(4-chloro-2-methylphenyl)piperidine hydrochloride (Intermediate 1a5) and 6-(dimethylamino)pyridazine-4-carboxylic acid (Intermediate 1b1). The crude product was purified via column chromatography on basic silica (solvent system: 10-100% ethyl acetate/petrol).

¹H NMR (400 MHz, CHCl₃-d) δ ppm 1.53-2.45 (m, 7 H) 2.63-3.14 (m, 2 H) 3.15-3.27 (m, 6 H) 3.31-3.77 (m, 1 H) 4.68-4.84 (m, 1 H) 6.68-6.86 (m, 1 H) 7.01-7.22 (m, 4 H) 8.48-8.57 (m, 1 H)

MS ES⁺: 358

Example 71

5-{[3-(4-Chloro-2-methylphenyl)piperidin-1-yl]carbonyl}-N-methylpyridazin-3-amine

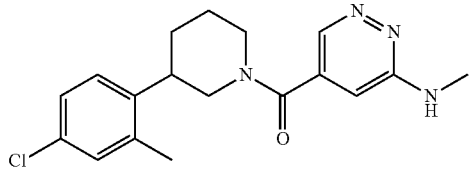 [SMILES: CNc1cc(C(=O)N2CCCC(c3ccc(Cl)cc3C)C2)cnn1]

To a stirred solution of 3-chloro-5-{[3-(4-chloro-2-methylphenyl)piperidin-1-yl]carbonyl}pyridazine (0.055 g, 0.157 mmol) (Intermediate 4) in butan-1-ol (3 mL) and N-methyl-2-pyrrolidinone (0.3 mL) was added methylamine (2.0M in THF) (0.314 mL, 0.628 mmol). The reaction vial was purged with nitrogen, sealed and irradiated in a microwave reactor at 100° C. for 10 minutes. Additional methylamine (2.0M in THF) (0.5 mL, 1 mmol) was added and the reaction irradiated in a microwave reactor at 135° C. for 140 minutes. Additional methylamine (2.0M in THF) (0.5 mL, 1 mmol) was added and the reaction was irradiated in a microwave reactor at 135° C. for 60 another minutes. Solvent and excess amine was removed in vacuo. The crude product was purified by reverse phase preparative HPLC eluting with acetonitrile/water (with 0.1% ammonia) to afford 5-{[3-(4-chloro-2-methylphenyl)piperidin-1-yl]carbonyl}-N-methylpyridazin-3-amine (35.4 mg, 0.103 mmol, 65% yield) as a solid.

¹H NMR (400 MHz, DMSO-d₆) δ ppm 1.47-1.97 (m, 4 H) 2.03-2.44 (m, 3 H) 2.62-2.98 (m, 5 H) 3.01-3.25 (m, 1 H) 3.25-3.54 (m, 1 H) 4.28-4.62 (m, 1 H) 6.66-6.83 (m, 1 H) 6.90-7.06 (m, 1 H) 7.10-7.39 (m, 3 H) 8.45 (m, 1 H)

MS ES⁺: 345

Examples 72 and 73

5-{[3-(4-Chloro-2-methylphenyl)piperidin-1-yl]carbonyl}-N-methylpyridazin-3-amine (enantiomers)

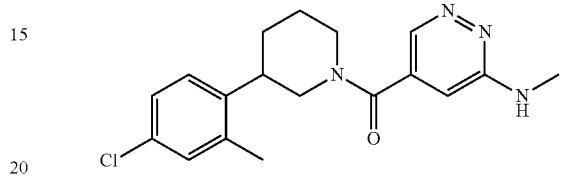

Racemic 5-{[3-(4-chloro-2-methylphenyl)piperidin-1-yl]carbonyl}-N-methylpyridazin-3-amine (Example 71) was dissolved to 25 mg/mL and was resolved by chiral HPLC using a Lux Amylose-2 21.2×250 mm 5 um column. The eluant used was heptane/ethanol in a 50/50 ratio with 0.1% TFA added to the diluent. The flow rate was 21 mL/min. The first product component to elute was collected and assigned 'enantiomer 1' and the second product component to elute was collected and assigned 'enantiomer 2'. The fractions were then evaporated using a rotary evaporator and dried in a vacuum oven at 40° C. and 25 mbar for 18 hours to give 5-{[3-(4-chloro-2-methylphenyl)piperidin-1-yl]carbonyl}-N-methylpyridazin-3-amine enantiomers as trifluoroacetate salts. The samples were free-based and triturated from petroleum ether (40-60) and diethyl ether to give 5-{[3-(4-chloro-2-methylphenyl)piperidin-1-yl]carbonyl}-N-methylpyridazin-3-amine enantiomer 1 and enantiomer 2 as solids.

Example 72

Enantiomer 1

5-{[(3R)-3-(4-Chloro-2-methylphenyl)piperidin-1-yl]carbonyl}-N-methylpyridazin-3-amine ¹H NMR (400 MHz, DMSO-d₆) δ ppm 1.47-1.97 (m, 4 H) 2.03-2.44 (m, 3 H) 2.62-2.98 (m, 5 H) 3.01-3.25 (m, 1 H) 3.25-3.54 (m, 1 H) 4.28-4.62 (m, 1 H) 6.66-6.83 (m, 1 H) 6.90-7.06 (m, 1 H) 7.10-7.39 (m, 3 H) 8.45 (m, 1 H)

MS ES⁺: 345

Chiral HPLC (Chiralpak AY column, 100×4.6 mm; isocratic 50% EtOH/50% IPA+0.2% TEA; 1.0 mL/min; 10° C.) Rt=2.8 mins.

Example 73

Enantiomer 2

5-{[(3S)-3-(4-Chloro-2-methylphenyl)piperidin-1-yl]carbonyl}-N-methylpyridazin-3-amine ¹H NMR (400 MHz, DMSO-d₆) δ ppm 1.47-1.97 (m, 4 H) 2.03-2.44 (m, 3 H) 2.62-2.98 (m, 5 H) 3.01-3.25 (m, 1 H) 3.25-3.54 (m, 1 H) 4.28-4.62 (m, 1 H) 6.66-6.83 (m, 1 H) 6.90-7.06 (m, 1 H) 7.10-7.39 (m, 3 H) 8.45 (m, 1 H)

MS ES⁺: 345

Chiral HPLC (Chiralpak AY column, 100×4.6 mm; isocratic 50% EtOH/50% IPA+0.2% TEA; 1.0 mL/min; 10° C.) Rt=4.2 mins.

Example 74

5-{[3-(4-Chloro-2-methylphenyl)piperidin-1-yl]carbonyl}-3-methoxypyridazine

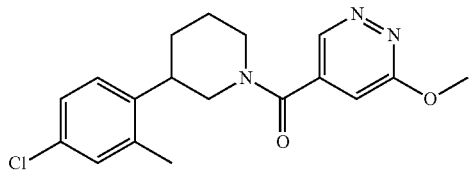 [SMILES: COc1cc(C(=O)N2CCCC(c3ccc(Cl)cc3C)C2)cnn1]

To a stirred solution of 3-chloro-5-{[3-(4-chloro-2-methylphenyl)piperidin-1-yl]carbonyl}pyridazine (0.055 g, 0.157 mmol) (Intermediate 4) in MeOH (2 mL) was added sodium methoxide (25 wt % in MeOH) (0.144 mL, 0.628 mmol). The reaction vial was purged with nitrogen, sealed and irradiated in a microwave reactor at 100° C. for 10 minutes. The reaction was quenched by addition of saturated aqueous ammonium chloride (1 mL), diluted in ethyl acetate (20 mL) and extracted with dilute aqueous hydrogen chloride (3%, 3×10 mL). The organic phase was reduced in vacuo. The crude product was purified by reverse phase preparative HPLC eluting with acetonitrile/water (with 0.1% ammonia) to yield the title product 5-{[3-(4-chloro-2-methylphenyl)piperidin-1-yl]carbonyl}-3-methoxypyridazine (2.6 mg, 7.44 μmol, 5% yield) as a colourless solid.

$^1$H NMR (400 MHz, CHCl$_3$-d) δ ppm 1.47-2.10 (m, 4 H) 2.12-2.50 (m, 3 H) 2.61-3.27 (m, 3 H) 3.42-3.76 (m, 1 H) 4.07-4.27 (m, 3 H) 4.66-4.90 (m, 1 H) 6.84-7.26 (m, 4 H) 8.73-9.04 (m, 1 H)

MS ES$^+$: 346

Example 75

5-({3-[4-Chloro-2-(trifluoromethyl)phenyl]piperidin-1-yl}carbonyl)-N,N-dimethylpyridazin-3-amine

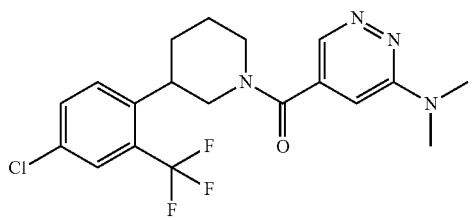 [SMILES: CN(C)c1cc(C(=O)N2CCCC(c3ccc(Cl)cc3C(F)(F)F)C2)cnn1]

To a stirred solution of 3-chloro-5-({3-[4-chloro-2-(trifluoromethyl)phenyl]piperidin-1-yl}carbonyl)pyridazine (0.060 g, 0.148 mmol) (Intermediate 5) in butan-1-ol (3 mL) was added dimethylamine (2.0M in THF) (0.742 mL, 1.484 mmol). The reaction vial was purged with nitrogen, sealed and irradiated in a microwave reactor at 135° C. for 45 minutes. Solvent and excess dimethylamine was removed in vacuo. The crude product was purified by reverse phase preparative HPLC eluting with acetonitrile/water (with 0.1% ammonia) to afford 5-({3-[4-chloro-2-(trifluoromethyl)phenyl]piperidin-1-yl}carbonyl)-N,N-dimethylpyridazin-3-amine (34.1 mg, 0.083 mmol, 56% yield) as a solid.

$^1$H NMR (400 MHz, DMSO-d$_6$) δ ppm 1.52-1.96 (m, 4 H) 2.74-3.60 (m, 10 H) 4.40-4.65 (m, 1 H) 6.92-7.14 (m, 1 H) 7.55-7.88 (m, 3 H) 8.30-8.56 (m, 1 H)

MS ES$^+$: 413

Example 76

5-({3-[4-Chloro-2-(trifluoromethyl)phenyl]piperidin-1-yl}carbonyl)-N-methylpyridazin-3-amine

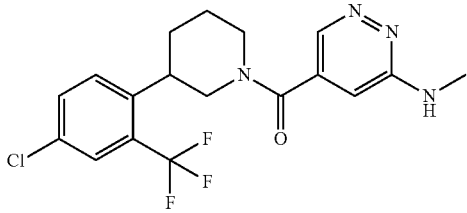 [SMILES: CNc1cc(C(=O)N2CCCC(c3ccc(Cl)cc3C(F)(F)F)C2)cnn1]

A solution of 3-chloro-5-({3-[4-chloro-2-(trifluoromethyl)phenyl]piperidin-1-yl}carbonyl)pyridazine (0.18 g, 0.445 mmol) (Intermediate 5) and methanamine (2M in THF) (4 mL, 8.00 mmol) was heated by microwave irradiation at 120° C. for 5.5 hours. The suspension was concentrated in vacuo. The crude product was purified by reverse phase preparative HPLC eluting with acetonitrile/water (with 0.1% ammonia). The product was freeze dried to afford 5-({3-[4-chloro-2-(trifluoromethyl)phenyl]piperidin-1-yl}carbonyl)-N-methylpyridazin-3-amine (0.085 g, 0.213 mmol, 47.9% yield) as solid.

$^1$H NMR (400 MHz, DMSO-d$_6$) δ ppm 1.48-1.96 (m, 4 H) 2.77-3.05 (m, 5 H) 3.13-3.61 (m, 2 H) 4.38-4.61 (m, 1 H) 6.64-6.82 (m, 1 H) 6.97 (br. s., 1 H) 7.63-7.86 (m, 3 H) 8.30-8.49 (m, 1 H)

MS ES$^+$: 399

Example 77

3-(Azetidin-1-yl)-5-({3-[4-chloro-2-(trifluoromethyl)phenyl]piperidin-1-yl}carbonyl)pyridazine

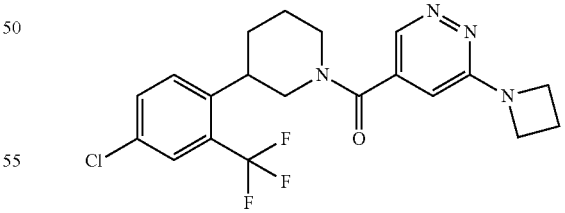

To a stirred solution of 3-chloro-5-({3-[4-chloro-2-(trifluoromethyl)phenyl]piperidin-1-yl}carbonyl)pyridazine (0.060 g, 0.148 mmol) (Intermediate 5) in butan-1-ol (3 mL) was added azetidine (0.100 mL, 1.484 mmol). The reaction vial was purged with nitrogen, sealed and irradiated in a microwave reactor at 135° C. for 45 minutes. The crude product was concentrated in vacuo and then purified by reverse phase preparative HPLC eluting with acetonitrile/water (with 0.1% ammonia) to afford 3-(azetidin-1-yl)-5-

({3-[4-chloro-2-(trifluoromethyl)phenyl]piperidin-1-yl}carbonyl)pyridazine (40.2 mg, 0.095 mmol, 63.7% yield) as a solid.

$^1$H NMR (400 MHz, DMSO-d$_6$) δ ppm 1.49-1.99 (m, 4 H) 2.27-2.46 (m, 2 H) 2.76-3.05 (m, 2 H) 3.10-3.56 (m, 2 H) 3.87-4.17 (m, 4 H) 4.37-4.64 (m, 1 H) 6.64-6.84 (m, 1 H) 7.61-7.88 (m, 3 H) 8.35-8.59 (m, 1 H)

MS ES$^+$: 425

Example 78

5-({3-[2-Methoxy-4-(trifluoromethyl)phenyl]piperidin-1-yl}carbonyl)-N-methylpyridazin-3-amine

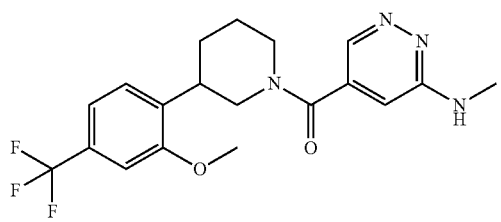 [SMILES: CNc1cc(C(=O)N2CCCC(c3ccc(C(F)(F)F)cc3OC)C2)cnn1]

3-Chloro-5-({3-[2-methoxy-4-(trifluoromethyl)phenyl]piperidin-1-yl}carbonyl)pyridazine (79 mg, 0.198 mmol) (Intermediate 6) was dissolved in THF (30 mL) and treated with methanamine (2M solution in THF) (3 mL, 6.00 mmol). This was heated at 130° C. in the microwave for 24 hours in total. The crude product was purified by column chromatography on basic silica, eluting with 20-100% ethyl acetate/petrol to afford 5-({3-[2-methoxy-4-(trifluoromethyl)phenyl]piperidin-1-yl}carbonyl)-N-methylpyridazin-3-amine (35 mg, 0.089 mmol, 45%).

$^1$H NMR (400 MHz, MeOH-d$_4$) δ ppm 1.62-1.88 (m, 2 H) 1.98-2.02 (m, 2 H) 2.85-3.00 (m, 1 H) 3.20-3.41 (m, 2 H) 3.40 (s, 3H) 3.66-3.82 (m, 2 H) 3.80 (s, 3H) 4.80 (br, 1 H) 6.81-6.83 (m, 1 H) 7.10 (s, 1 H) 7.20-7.31 (m, 1 H) 7.35-7.40 (m, 1 H) 8.40 (m, 1 H)

MS ES$^+$: 395

Example 79

5-{[3-(4-Methoxy-2-methylphenyl)piperidin-1-yl]carbonyl}-N-methylpyridazin-3-amine

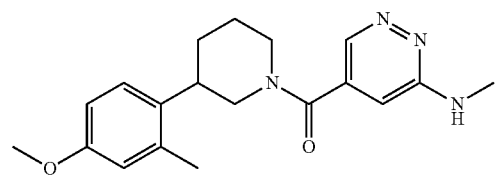

To a stirred solution of 3-chloro-5-{[3-(4-methoxy-2-methylphenyl)piperidin-1-yl]carbonyl}pyridazine (0.067 g, 0.194 mmol) (Intermediate 7) in butan-1-ol (2 mL) and NMP (1 mL) was added methylamine (2.0M in THF) (1.453 mL, 2.91 mmol). The vial was purged with nitrogen, sealed and irradiated in the microwave at 135° C. for 30 minutes. The crude reaction mixture was diluted with EtOAc (20 mL) and washed firstly with water (3×10 mL) and then with brine (10 mL), dried (with what) and then evapourated in vacuo?. The crude product was purified by reverse phase preparative HPLC eluting with acetonitrile/water (with 0.1% ammonia) to afford 5-{[3-(4-methoxy-2-methylphenyl)piperidin-1-yl]carbonyl}-N-methylpyridazin-3-amine (43.1 mg, 0.127 mmol, 65% yield) as a solid.

$^1$H NMR (400 MHz, DMSO-d$_6$) δ ppm 1.44-1.92 (m, 4 H) 1.98-2.38 (m, 3 H) 2.62-3.58 (m, 7 H) 3.62-3.81 (m, 3 H) 4.29-4.63 (m, 1 H) 6.56-7.27 (m, 5 H) 8.44 (d, J=4.55 Hz, 1 H)

MS ES$^+$: 341

Example 80

5-{[3-(4-Methoxy-2-methylphenyl)piperidin-1-yl]carbonyl}-N,N-dimethylpyridazin-3-amine

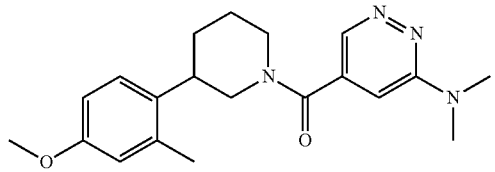

To a stirred solution of 3-chloro-5-{[3-(4-methoxy-2-methylphenyl)piperidin-1-yl]carbonyl}pyridazine (0.067 g, 0.194 mmol) (Intermediate 7) in butan-1-ol (2 mL) was added dimethylamine (2M in THF) (1.453 mL, 2.91 mmol). The vial was purged with nitrogen, sealed and irradiated in the microwave at 135° C. for 30 minutes. The resulting mixture was concentrated in vacuo, diluted with EtOAc (20 mL) and washed with water (3×10 mL) and then with brine (10 mL). The crude product was purified by reverse phase preparative HPLC eluting with acetonitrile/water (with 0.1% ammonia) to afford 5-{[3-(4-methoxy-2-methylphenyl)piperidin-1-yl]carbonyl}-N,N-dimethylpyridazin-3-amine (26.4 mg, 0.073 mmol, 38% yield) as a solid.

$^1$H NMR (400 MHz, DMSO-d$_6$) δ ppm 1.38-1.92 (m, 4 H) 1.96-2.41 (m, 3 H) 2.60-3.55 (m, 10 H) 3.58-3.80 (m, 3 H) 4.32-4.61 (m, 1 H) 6.57-6.83 (m, 2 H) 6.98-7.29 (m, 2 H) 8.50 (d, J=8.34 Hz, 1 H)

MS ES$^+$: 355

Example 81

5-({3-[4-Methoxy-2-(trifluoromethyl)phenyl]piperidin-1-yl}carbonyl)-N-methylpyridazin-3-amine

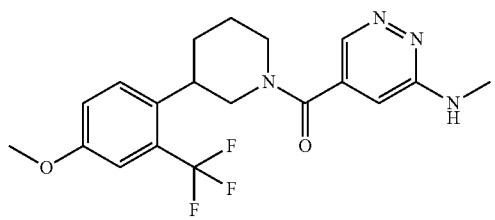

A solution of 3-chloro-5-({3-[4-methoxy-2-(trifluoromethyl)phenyl]piperidin-1-yl}carbonyl)pyridazine (0.072 g, 0.180 mmol) (Intermediate 8) and methylamine (2.0M in THF) (1.351 mL, 2.70 mmol) in NMP (1 mL) and butan-1-ol (2 mL) was irradiated in a sealed tube in a microwave at 135° C. for 150 minutes. The crude product was concentrated in vacuo, re-dissolved in EtOAc (20 mL) and washed with water (3×5 mL) and then brine (5 mL). The organic phase was concentrated in vacuo and purified by reverse phase preparative HPLC eluting with acetonitrile/water (with 0.1% ammonia) to afford 5-({3-[4-methoxy-2-(trifluoromethyl)phenyl]piperidin-1-yl}carbonyl)-N-methylpyridazin-3-amine (36.4 mg, 0.092 mmol, 51% yield) as a solid.

$^1$H NMR (400 MHz, DMSO-$d_6$) δ ppm 1.43-1.97 (m, 4 H) 2.73-2.99 (m, 5 H) 3.10-3.60 (m, 2 H) 3.70-3.90 (m, 3 H) 4.36-4.66 (m, 1 H) 6.54-6.83 (m, 1 H) 6.96 (br. s., 1 H) 7.05-7.32 (m, 2 H) 7.48-7.74 (m, 1 H) 8.23-8.52 (m, 1 H)

MS ES$^+$: 395

Example 82

5-({3-[4-Methoxy-2-(trifluoromethyl)phenyl]piperidin-1-yl}carbonyl)-N,N-dimethylpyridazin-3-amine

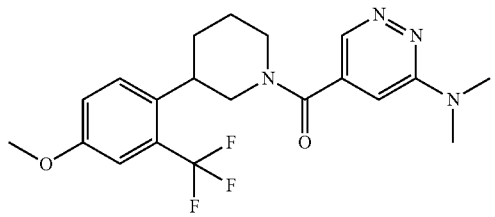

A solution of 3-chloro-5-({3-[4-methoxy-2-(trifluoromethyl)phenyl]piperidin-1-yl}carbonyl)pyridazine (0.072 g, 0.180 mmol) (Intermediate 8) and dimethylamine (2M in THF) (1.351 mL, 2.70 mmol) in NMP (1 mL) and butan-1-ol (2 mL) was irradiated in a sealed tube in a microwave at 135° C. for 30 minutes. The resulting mixture was concentrated in vacuo, re-dissolved in EtOAc (20 mL) and washed with water (3×5 mL) and brine (5 mL). The organic phase was concentrated in vacuo and purified by reverse phase preparative HPLC eluting with acetonitrile/water (with 0.1% ammonia) to afford 5-({3-[4-methoxy-2-(trifluoromethyl)phenyl]piperidin-1-yl}carbonyl)-N,N-dimethylpyridazin-3-amine (36.6 mg, 0.090 mmol, 50% yield) as a solid.

$^1$H NMR (400 MHz, DMSO-$d_6$) δ ppm 1.43-2.00 (m, 4 H) 2.76-3.01 (m, 2 H) 3.03-3.19 (m, 6 H) 3.21-3.56 (m, 2 H) 3.68-3.89 (m, 3 H) 4.38-4.69 (m, 1 H) 6.89-7.34 (m, 3 H) 7.50-7.74 (m, 1 H) 8.31-8.56 (m, 1 H)

MS ES$^+$: 409

Example 83

5-{[3-(4-Chloro-2-ethoxyphenyl)piperidin-1-yl]carbonyl}-N-methylpyridazin-3-amine

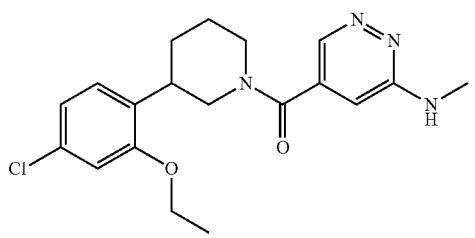 [SMILES: CCOc1cc(Cl)ccc1C1CCCN(C(=O)c2cnnc(NC)c2)C1]

To a solution of 3-chloro-5-{[3-(4-chloro-2-ethoxyphenyl)piperidin-1-yl]carbonyl}pyridazine (0.050 g, 0.131 mmol) (Intermediate 9) in butan-1-ol (2 mL) and NMP (1 mL) was added methylamine (2.0M in THF) (0.986 mL, 1.972 mmol). The vial was sealed and irradiated in the microwave at 135° C. for 60 minutes. The reaction was concentrated in vacuo. The crude product was purified by reverse phase preparative HPLC eluting with acetonitrile/water (with 0.1% ammonia) to afford 5-{[3-(4-chloro-2-ethoxyphenyl)piperidin-1-yl]carbonyl}-N-methylpyridazin-3-amine (36 mg, 0.096 mmol, 73.0% yield) as a solid.

$^1$H NMR (400 MHz, DMSO-$d_6$) δ ppm 1.05-1.44 (m, 3 H) 1.47-1.96 (m, 4 H) 2.65-3.18 (m, 6 H) 3.44-3.63 (m, 1 H) 3.84-4.20 (m, 2 H) 4.51 (br. s., 1 H) 6.62-6.82 (m, 1 H) 6.89-7.10 (m, 3 H) 7.13-7.32 (m, 1 H) 8.32-8.49 (m, 1 H)

MS ES$^+$: 375

Example 84

5-{[3-(4-Chloro-2-ethoxyphenyl)piperidin-1-yl]carbonyl}-N,N-dimethylpyridazin-3-amine

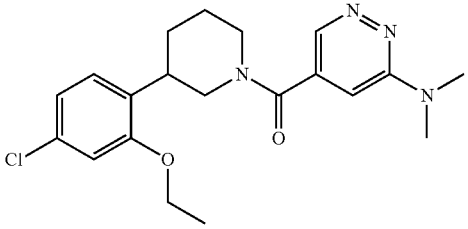 [SMILES: CCOc1cc(Cl)ccc1C1CCCN(C(=O)c2cnnc(N(C)C)c2)C1]

To a solution of 3-chloro-5-{[3-(4-chloro-2-ethoxyphenyl)piperidin-1-yl]carbonyl}pyridazine (0.050 g, 0.131 mmol) (Intermediate 9) in butan-1-ol (2 mL) and NMP (1 mL) was added dimethylamine (2M in THF) (0.986 mL, 1.972 mmol). The vial was sealed and irradiated in the microwave at 135° C. for 90 minutes. The resulting mixture was concentrated in vacuo and then purified by reverse phase preparative HPLC eluting with acetonitrile/water (with 0.1% ammonia) to afford 5-{[3-(4-chloro-2-ethoxyphenyl)piperidin-1-yl]carbonyl}-N,N-dimethylpyridazin-3-amine (40.5 mg, 0.104 mmol, 79% yield) as a solid.

$^1$H NMR (400 MHz, DMSO-$d_6$) δ ppm 1.04-1.46 (m, 3 H) 1.51-1.96 (m, 4 H) 2.70-2.86 (m, 1 H) 2.92-3.20 (m, 8 H) 3.40-3.58 (m, 1 H) 3.80-4.23 (m, 2 H) 4.52 (m, 1 H) 6.76-7.11 (m, 3 H) 7.15-7.36 (m, 1 H) 8.38-8.58 (m, 1 H)

MS ES$^+$: 389

Example 85

5-{[3-(4-Chloro-2-methylphenyl)piperidin-1-yl]carbonyl}-3-methylpyridazine

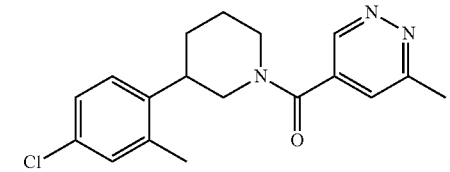 [SMILES: Cc1cc(C(=O)N2CCCC(c3ccc(Cl)cc3C)C2)cnn1]

A solution of 3-chloro-4-{[3-(4-chloro-2-methylphenyl)piperidin-1-yl]carbonyl}-6-methylpyridazine (0.1 g, 0.275 mmol) (Intermediate 10) in MeOH (10 mL) was eluted through a hydrogen flow reactor (Thales H-cube) fitted with 5% palladium on carbon catalyst cartridge at 20° C., 1.5 mL/min and atmospheric pressure. After 90 mins the solvent was removed in vacuo and the crude product was purified by reverse phase preparative HPLC eluting with acetonitrile/water (with 0.1% ammonia) to afford 5-{[3-(4-chloro-2-methylphenyl)piperidin-1-yl]carbonyl}-3-methylpyridazine as a colourless solid.

$^1$H NMR (400 MHz, CHCl$_3$-d) δ ppm 1.44-2.53 (m, 7 H) 2.58-3.28 (m, 6 H) 3.33-3.78 (m, 1 H) 4.68-4.93 (m, 1 H) 6.94-7.45 (m, 4 H) 8.98-9.15 (m, 1 H)

MS ES$^+$: 330

Example 86

5-{[3-(2-Methoxyphenyl)piperidin-1-yl]carbonyl}-N-methylpyridazin-3-amine

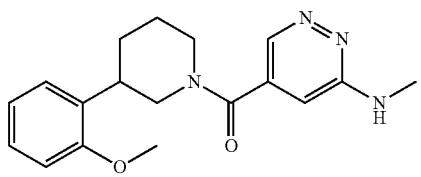 [SMILES: CNc1cc(C(=O)N2CCCC(c3ccccc3OC)C2)cnn1]

A sealed microwave tube containing 3-chloro-5-{[3-(2-methoxyphenyl)piperidin-1-yl]carbonyl}pyridazine (7.2 mg, 0.022 mmol) (Intermediate 11) and methylamine (2.0M in THF) (0.271 mL, 0.543 mmol) dissolved in butan-1-ol (1 mL) and NMP (0.2 mL), this was irradiated in the microwave at 135° C. for 150 minutes. The crude product was purified by reverse phase preparative HPLC eluting with acetonitrile/water (with 0.1% ammonia) and lyophilised to afford 5-{[3-(2-methoxyphenyl)piperidin-1-yl]carbonyl}-N-methylpyridazin-3-amine (3.3 mg, 10.11 μmol, 47% yield) as a solid.

$^1$H NMR (400 MHz, MeCN-d$_3$) δ ppm 1.46-1.88 (m, 3 H) 2.07-2.26 (m, 1 H) 2.68-3.02 (m, 5 H) 3.03-3.26 (m, 1 H) 3.53-3.94 (m, 4 H) 4.48-4.69 (m, 1 H) 5.52 (br. s., 1 H) 6.54-6.74 (m, 1 H) 6.76-7.11 (m, 2 H) 7.14-7.38 (m, 2 H) 8.34-8.55 (m, 1 H)

MS ES$^-$: 325

Example 87

3-(4-Chloro-2-methylphenyl)-1-[(1,3-dimethyl-1H-pyrazol-4-yl)carbonyl]piperidine

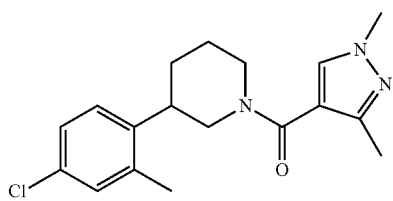 [SMILES: Cc1cc(Cl)ccc1C1CCCN(C(=O)c2cn(C)nc2C)C1]

A solution of 3-(4-chloro-2-methylphenyl)piperidine hydrochloride (50 mg, 0.203 mmol) (Intermediate 1a5) in DCM (10 mL) was treated with 1,3-dimethyl-1H-pyrazole-4-carboxylic acid (31.3 mg, 0.223 mmol), 1-ethyl-3-(3-dimethylaminopropyl)carbodiimide hydrochloride (48.7 mg, 0.254 mmol), 1-hydroxybenzotriazole hydrate (34.8 mg, 0.227 mmol) and triethylamine (0.057 mL, 0.406 mmol). The mixture was stirred at room temperature for 17 hours. Water was added to the reaction mixture which was stirred vigorously for 30 minutes before the phases were separated using a phase separation cartridge. The organic phase was concentrated in vacuo. The crude product was purified by preparative LCMS (basic conditions) to give the title compound 3-(4-chloro-2-methylphenyl)-1-[(1,3-dimethyl-1H-pyrazol-4-yl)carbonyl]piperidine (42 mg, 62%).

$^1$H NMR (400 MHz, DCM-d$_2$) δ ppm 1.57-2.07 (m, 4 H) 2.32 (s, 6 H) 2.78-3.07 (m, 3 H) 3.87 (s, 3 H) 4.12-4.52 (m, 2 H) 7.14-7.22 (m, 3 H) 7.45 (s, 1 H)

MS ES$^+$: 332

Example 88

3-(4-Chlorophenyl)-1-[(1,3-dimethyl-1H-pyrazol-4-yl)carbonyl]piperidine

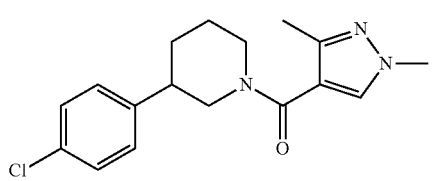 [SMILES: Cc1nn(C)cc1C(=O)N1CCCC(c2ccc(Cl)cc2)C1]

Prepared as described for 3-(4-chloro-2-methylphenyl)-1-[(1,3-dimethyl-1H-pyrazol-4-yl)carbonyl]piperidine (Example 87) from 3-(4-chlorophenyl)piperidine and 1,3-dimethyl-1H-pyrazole-4-carboxylic acid.

$^1$H NMR (400 MHz, DCM-d$_2$) δ ppm 1.53-1.93 (m, 3 H) 2.09 (m, 1 H) 2.24-2.39 (m, 3 H) 2.75 (m, 1 H) 2.92 (br. s., 2 H) 3.88 (s, 3 H) 4.34 (br. s., 2 H) 7.22 (m, 2 H) 7.33 (m, 2 H) 7.45 (s, 1 H)

MS ES$^+$: 318

Example 89

3-(4-Chlorophenyl)-1-[(1-methyl-1H-pyrazol-4-yl)carbonyl]piperidine

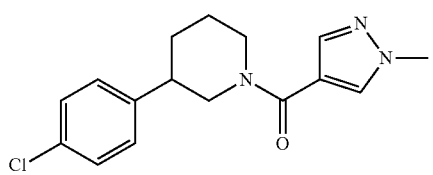 [SMILES: Cn1cc(C(=O)N2CCCC(c3ccc(Cl)cc3)C2)cn1]

Prepared as described for 3-(4-chloro-2-methylphenyl)-1-[(1,3-dimethyl-1H-pyrazol-4-yl)carbonyl]piperidine (Example 87) from 3-(4-chlorophenyl)piperidine and 1-methyl-1H-pyrazole-4-carboxylic acid.

$^1$H NMR (400 MHz, CHCl$_3$-d) δ ppm 1.62-1.82 (m, 2 H) 1.83-1.94 (m, 1 H) 2.07-2.16 (m, 1 H) 2.69-3.23 (m, 3 H) 3.94 (s, 3 H) 4.22-4.89 (m, 2 H) 7.13-7.23 (m, 2 H) 7.25-7.35 (m, 2 H) 7.63 (s, 1 H) 7.71 (s, 1 H)

MS ES$^+$: 304

Example 90

3-(4-Chlorophenyl)-1-[(1-ethyl-1H-pyrazol-4-yl)carbonyl]piperidine

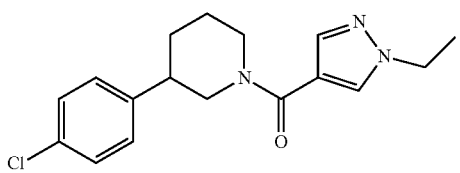 [SMILES: CCn1cc(C(=O)N2CCCC(c3ccc(Cl)cc3)C2)cn1]

Prepared as described for 3-(4-chloro-2-methylphenyl)-1-[(1,3-dimethyl-1H-pyrazol-4-yl)carbonyl]piperidine (Example 87) from 3-(4-chlorophenyl)piperidine and 1-ethyl-1H-pyrazole-4-carboxylic acid.

$^1$H NMR (CHCl$_3$-d) δ ppm 1.43-1.82 (m, 7 H) 1.85-1.94 (m, 1 H) 2.07-2.16 (m, 2 H) 2.78-2.30 (m, 2 H) 4.20-4.25 (m, 2 H) 7.14-7.25 (m, 2 H) 7.25-7.34 (m, 2 H) 7.64 (s, 1 H) 7.76 (s, 1 H)

MS ES$^+$: 318

Example 91

3-(4-Chlorophenyl)-1-{[1-(propan-2-yl)-1H-pyrazol-4-yl]carbonyl}piperidine

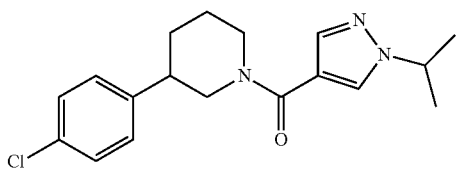 [SMILES: CC(C)n1cc(C(=O)N2CCCC(c3ccc(Cl)cc3)C2)cn1]

Prepared as described for 3-(4-chloro-2-methylphenyl)-1-[(1,3-dimethyl-1H-pyrazol-4-yl)carbonyl]piperidine (Example 87) from 3-(4-chlorophenyl)piperidine and 1-isopropyl-1H-pyrazole-4-carboxylic acid.

$^1$H NMR (CHCl$_3$-d) δ ppm 1.47-1.83 (m, 10 H) 1.83-1.94 (m, 1 H) 2.07-2.16 (m, 2 H) 2.71-2.85 (m, 2 H) 4.45-4.56 (m, 1 H) 7.13-7.22 (m, 2 H) 7.27-7.38 (m, 2 H) 7.64 (s, 1 H) 7.80 (s, 1 H)

MS ES$^+$: 332

Example 92

3-(4-Chloro-2-methylphenyl)-1-[(1-ethyl-1H-pyrazol-4-yl)carbonyl]piperidine

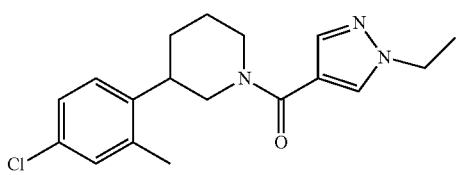 [SMILES: CCn1cc(C(=O)N2CCCC(c3ccc(Cl)cc3C)C2)cn1]

Propylphosphonic anhydride (50 wt % solution in EtOAc; 0.257 mL, 0.404 mmol) was added to a suspension of 3-(4-chloro-2-methylphenyl)piperidine hydrochloride (0.065 g, 0.264 mmol) (Intermediate 1a5), 1-ethyl-1H-pyrazole-4-carboxylic acid and triethylamine (0.092 mL, 0.660 mmol) in DCM (1 mL). The reaction was stirred at room temperature for 18 hours. The reaction was concentrated in vacuo and the crude product was purified by reverse phase preparative HPLC eluting with acetonitrile/water (with 0.1% ammonia) to afford 3-(4-chloro-2-methylphenyl)-1-[(1-ethyl-1H-pyrazol-4-yl)carbonyl]piperidine (52 mg, 0.149 mmol, 68% yield) as a solid.

$^1$H NMR (400 MHz, CHCl$_3$-d) δ ppm 1.52 (t, J=7.33 Hz, 3 H) 1.57-1.84 (m, 2 H) 1.85-1.96 (m, 1 H) 1.97-2.09 (m, 1 H) 2.14-2.51 (m, 3 H) 2.61-3.30 (m, 3 H) 4.20 (q, J=7.30 Hz, 2 H) 4.28-4.89 (m, 2 H) 7.08-7.22 (m, 3 H) 7.57-7.83 (m, 2 H)

MS ES$^+$: 332

Example 93

3-(4-Chloro-2-methylphenyl)-1-{[1-(propan-2-yl)-1H-pyrazol-4-yl]carbonyl}piperidine

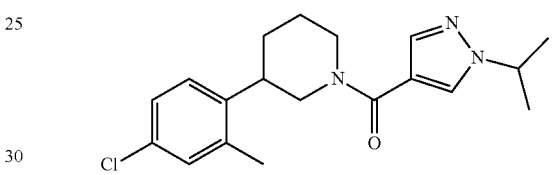

Propylphosphonic anhydride (50 wt % solution in EtOAc; 0.257 mL, 0.404 mmol) was added to a suspension of 3-(4-chloro-2-methylphenyl)piperidine hydrochloride (0.065 g, 0.264 mmol) (Intermediate 1a5), 1-isopropyl-1H-pyrazole-4-carboxylic acid (41 mg, 0.264) in DCM (1 mL). The reaction was stirred at room temperature for 18 hours was and then reduced in vacuo. The crude product was purified by reverse phase preparative HPLC eluting with acetonitrile/water (with 0.1% ammonia) to afford 3-(4-chloro-2-methylphenyl)-1-{[1-(propan-2-yl)-1H-pyrazol-4-yl]carbonyl}piperidine (55 mg, 0.151 mmol, 69% yield) as a solid.

$^1$H NMR (400 MHz, CHCl$_3$-d) δ ppm 1.54 (d, J=6.82 Hz, 6 H) 1.65-1.85 (m, 2 H) 1.85-1.95 (m, 1 H) 1.97-2.08 (m, 1 H) 2.14-2.50 (m, 3 H) 2.58-3.30 (m, 3 H) 4.07-4.42 (m, 1 H) 4.44-4.57 (m, 1 H) 4.60-4.85 (m, 1 H) 7.08-7.24 (m, 3 H) 7.56-7.87 (m, 2 H)

MS ES$^+$: 346

Example 94

3-(4-Chloro-2-methylphenyl)-1-[(1-methyl-1H-pyrazol-4-yl)carbonyl]piperidine

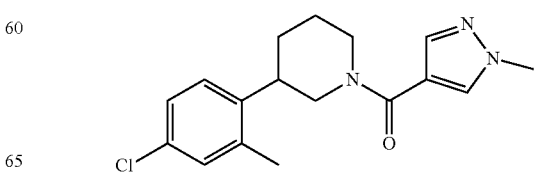

Propylphosphonic anhydride (50 wt % solution in EtOAc; 0.257 mL, 0.440 mmol) was added to a suspension of 3-(4-chloro-2-methylphenyl)piperidine hydrochloride (0.065 g, 0.264 mmol) (Intermediate 1a5), 1-methyl-1H-pyrazole-4-carboxylic acid (33 mg, 0.264) in DCM (1 mL). The reaction was stirred at room temperature for 18 hours. The reaction was concentrated in vacuo and the crude product was purified by reverse phase preparative HPLC eluting with acetonitrile/water (with 0.1% ammonia) to afford 3-(4-chloro-2-methylphenyl)-1-[(1-methyl-1H-pyrazol-4-yl)carbonyl]piperidine (58 mg, 0.173 mmol, 79% yield) as a solid.

$^1$H NMR (400 MHz, CHCl$_3$-d) δ ppm 1.63-1.83 (m, 2 H) 1.84-1.96 (m, 1 H) 1.97-2.08 (m, 1 H) 2.12-2.48 (m, 3 H) 2.60-3.33 (m, 3 H) 3.94 (s, 3 H) 4.08-4.88 (m, 2 H) 7.06-7.23 (m, 3 H) 7.56-7.80 (m, 2 H)

MS ES$^+$: 318

Example 95

4-{[3-(4-Chloro-2-methylphenyl)piperidin-1-yl]carbonyl}-1-methyl-1H-pyrazol-5-amine

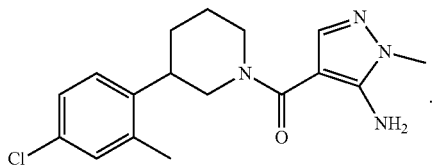 [SMILES: Cc1cc(Cl)ccc1C1CCCN(C(=O)c2cnn(C)c2N)C1]

A solution of 3-(4-chloro-2-methylphenyl)-1-[(1-methyl-5-nitro-1H-pyrazol-4-yl)carbonyl]piperidine (205 mg, 0.565 mmol) (Intermediate 2a1) in MeOH (10 mL) was cycled through a hydrogen flow cell (Thales H-Cube) at 1.0 mL/min, 20° C., fitted with 10% Pt/C catalyst cartridge. After 1 hour the reactor was washed through with additional MeOH (3 mL). The solvent was removed in vacuo to give 4-{[(3-(4-chloro-2-methylphenyl)piperidin-1-yl]carbonyl}-1-methyl-1H-pyrazol-5-amine (0.195 g, 0.557 mmol, 99% yield) as a gum that partially crystallised on standing to give a solid.

$^1$H NMR (400 MHz, DMSO-d$_6$) δ ppm 1.43-1.93 (m, 4 H) 2.20-2.38 (m, 3 H) 2.67-3.09 (m, 3 H) 3.53 (s, 3 H) 4.14-4.39 (m, 2 H) 6.05 (s, 2 H) 7.14-7.40 (m, 4 H)

MS ES$^+$: 333

Example 96

3-[4-Chloro-2-(trifluoromethyl)phenyl]-1-[(1H-pyrazol-4-yl)carbonyl]piperidine

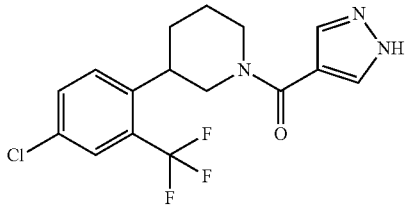 [SMILES: O=C(c1cn[nH]c1)N1CCCC(c2ccc(Cl)cc2C(F)(F)F)C1]

Method 1:

Triethylamine (0.836 mL, 6.00 mmol) was added to a suspension of 3-[4-chloro-2-(trifluoromethyl)phenyl]piperidine hydrochloride (0.6 g, 1.999 mmol) (Intermediate 1a6), 1H-pyrazole-4-carboxylic acid (0.246 g, 2.199 mmol), EDC (0.575 g, 3.00 mmol) and 1-hydroxybenzotriazole hydrate (0.408 g, 3.00 mmol) in DCM (10 mL). The reaction was stirred at room temperature for 48 hours. The mixture was diluted with DCM, washed with saturated aqueous NaHCO$_3$ (1×50 mL), 5% aqueous citric acid (1×50 mL), water (1×50 mL) and the organic phase was isolated using a phase separator cartridge and concentrated in vacuo. The crude product was purified by column chromatography on silica, eluting with 0-100% ethyl acetate/petrol to afford 3-[4-chloro-2-(trifluoromethyl)phenyl]-1-[(1H-pyrazol-4-yl)carbonyl]piperidine (0.473 g, 1.322 mmol, 66% yield) as a colourless glass.

Method 2:

Triethylamine (1.776 mL, 12.75 mmol) was added to a suspension of 3-[4-chloro-2-(trifluoromethyl)phenyl]piperidine (1.120 g, 4.25 mmol) (Intermediate 1a6), 1H-pyrazole-4-carboxylic acid (0.5 g, 4.46 mmol). EDC (1,222 g, 6.37 mmol) and HOAt (0.867 g, 6.37 mmol) in DCM (30 mL). The reaction was stirred at room temperature for 3 hours. The mixture was diluted with DCM, washed with saturated aqueous NaHCO$_3$ (1×100 mL), 5% aqueous citric acid (1×100 mL), water (1×100 mL) and the organic phase was isolated using a phase separator cartridge and concentrated in vacuo. The crude product was purified by column chromatography on silica, eluting with 0-100% ethyl acetate/petrol to afford 3-[4-chloro-2-(trifluoromethyl)phenyl]-1-[(1H-pyrazol-4-yl)carbonyl]piperidine (1.25 g, 3.49 mmol, 82% yield) as a foam.

$^1$H NMR (400 MHz, DMSO-d$_6$) δ ppm 1.44-1.59 (m, 1 H) 1.70-1.94 (m, 3 H) 2.54-3.23 (m, 3 H) 4.15-4.74 (m, 2 H) 7.69-7.81 (m, 5 H) 13.15 (br. s., 1 H)

MS ES$^+$: 358

Example 97

3-[4-Chloro-2-(trifluoromethyl)phenyl]-1-[(1-methyl-1H-pyrazol-4-yl)carbonyl]piperidine

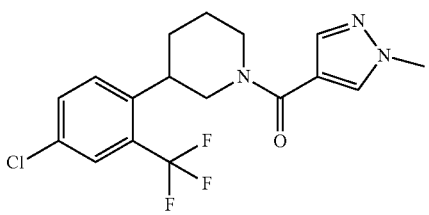 [SMILES: Cn1cc(C(=O)N2CCCC(c3ccc(Cl)cc3C(F)(F)F)C2)cn1]

Sodium hydride (0.011 g, 0.280 mmol) was added to a solution of 3-[4-chloro-2-(trifluoromethyl)phenyl]-1-[(1H-pyrazol-4-yl)carbonyl]piperidine (0.1 g, 0.280 mmol) (Example 96) in DMF (2 mL) under nitrogen. The reaction was stirred at room temperature for 10 minutes then methyl iodide (0.0.017 mL, 0.280 mmol) was added and the reaction stirred for 1 hour. The mixture was partitioned between ethyl acetate and water. The phases were separated and the aqueous extracted with ethyl acetate (3×25 mL). The combined organics were concentrated in vacuo. The crude product was purified by reverse phase preparative HPLC eluting with acetonitrile/water (with 0.1% ammonia) to afford 3-[4-chloro-2-(trifluoromethyl)phenyl]-1-[(1-methyl-1H-pyrazol-4-yl)carbonyl]piperidine (0.048 g, 0.129 mmol, 46% yield) as a solid.

$^1$H NMR (400 MHz, DMSO-d$_6$) δ ppm 1.53 (br. s., 1 H) 1.75-1.92 (m, 3 H) 2.90 (br. s., 2H) 3.83 (s, 3 H) 4.00-4.40 (m, 3 H) 7.62 (br. s., 1 H) 7.72-7.82 (m, 3 H) 8.03 (br. s., 1 H) MS ES$^+$: 372

Example 98

3-[4-Chloro-2-(trifluoromethyl)phenyl]-1-[(1-ethyl-1H-pyrazol-4-yl)carbonyl]piperidine

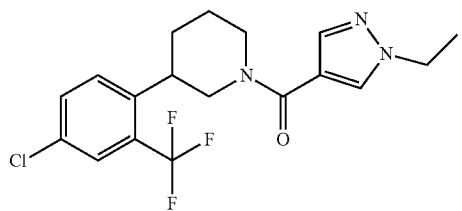 [SMILES: CCn1cc(C(=O)N2CCCC(c3ccc(Cl)cc3C(F)(F)F)C2)cn1]

Sodium hydride (0.056 g, 1.398 mmol) was added to a solution of 3-[4-chloro-2-(trifluoromethyl)phenyl]-1-[(1H-pyrazol-4-yl)carbonyl]piperidine (0.5 g, 1.398 mmol) (Example 96) in THF (10 mL) under nitrogen. The reaction mixture was stirred at room temperature for 10 minutes. Ethyl iodide (0.113 mL, 1.398 mmol) was added and the suspension stirred at room temperature overnight. The mixture was partitioned between ethyl acetate and water. The phases were separated and the aqueous phase was extracted with ethyl acetate (2×50 mL). The combined organics were washed with saturated brine (1×75 mL) and concentrated in vacuo. The crude product was purified by reverse phase chromatography on C18 silica eluting with 40-70% acetonitrile/water (with 0.05% NH$_4$OH) and freeze dried to afford 3-[4-chloro-2-(trifluoromethyl)phenyl]-1-[(1-ethyl-1H-pyrazol-4-yl)carbonyl]piperidine (0.368 g, 0.954 mmol, 68% yield) as a glass.

$^1$H NMR (400 MHz, DMSO-d$_6$) δ ppm 1.36 (t, J=6.82 Hz, 3 H) 1.52 (m, 1 H) 1.70-1.97 (m, 3 H) 2.6-3.6 (br. m, 3 H), 3.9-4.6 (br. m, 2 H) 4.13 (q. J=6.82 Hz, 2 H) 7.48-7.86 (m, 4 H) 8.06 (br. m., 1 H)

MS ES$^+$: 386

Example 99

3-[4-Chloro-2-(trifluoromethyl)phenyl]-1-{[1-(propan-2-yl)-1H-pyrazol-4-yl]carbonyl}piperidine

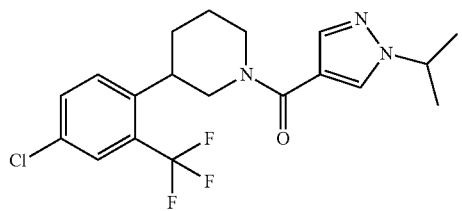 [SMILES: CC(C)n1cc(C(=O)N2CCCC(c3ccc(Cl)cc3C(F)(F)F)C2)cn1]

Sodium hydride (0.011 g, 0.280 mmol) was added to a solution of 3-[4-chloro-2-(trifluoromethyl)phenyl]-1-[(1H-pyrazol-4-yl)carbonyl]piperidine (0.1 g, 0.280 mmol) (Example 96) in THF (2 mL) under nitrogen. The reaction mixture was stirred at room temperature for 10 minutes then 2-iodopropane (0.048 g, 0.280 mmol) was added and the reaction mixture was stirred overnight. Additional portions of sodium hydride (0.011 g, 0.280 mmol) and 2-iodopropane (0.288 g, 1.680 mmol) were added and the reaction mixture was stirred overnight and then heated to reflux for 24 hours. The mixture was partitioned between ethyl acetate and water. The phases were separated and the aqueous phase was extracted with ethyl acetate (3×25 mL). The combined organics were washed with saturated brine (25 mL) separated and concentrated in vacuo. The crude product was purified by reverse phase preparative HPLC eluting with acetonitrile/water (with 0.1% ammonia) and freeze dried to afford 3-[4-chloro-2-(trifluoromethyl)phenyl]-1-[1-(propan-2-yl)-1H-pyrazol-4-yl]carbonyl)piperidine (0.046 g, 0.115 mmol, 41% yield) as a solid.

$^1$H NMR (400 MHz, DMSO-d$_6$) δ ppm 1.31-1.46 (m, 6 H) 1.54 (br. s., 1 H) 1.73-1.96 (m, 3 H) 2.65-3.12 (m, 3 H) 4.22-4.91 (m, 3 H) 7.62 (br. s., 1 H) 7.70-7.82 (m, 3 H) 8.08 (br. s., 1 H)

MS ES$^+$: 400

Example 100

4-({3-[4-Chloro-2-(trifluoromethyl)phenyl]piperidin-1-yl}carbonyl)-1-methyl-1H-pyrazol-3-amine

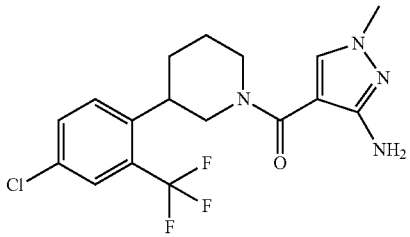 [SMILES: Cn1cc(C(=O)N2CCCC(c3ccc(Cl)cc3C(F)(F)F)C2)c(N)n1]

Hydrogen chloride (4M in dioxane) (0.770 mL, 3.08 mmol) was added to a solution of tert-butyl N-[4-((3-[4-chloro-2-(trifluoromethyl)phenyl]piperidin-1-yl carbonyl)-1-methyl-1H-pyrazol-3-yl]carbamate (0.5 g, 1.027 mmol) (Intermediate 2a2) in MeOH (5 mL). The reaction mixture was stirred at room temperature for 48 hours. A further portion of hydrogen chloride (4M in dioxane) (0.770 mL, 3.08 mmol) was added and the reaction mixture stirred at room temperature for 24 hours. The mixture was concentrated in vacuo and azeotroped with toluene. The crude product was purified by reverse phase chromatography on C18 silica eluting with 25-50% acetonitrile/water (with 0.05% ammonia) to afford 4-({3-[4-chloro-2-(trifluoromethyl)phenyl]piperidin-1-yl}carbonyl)-1-methyl-1H-pyrazol-3-amine (0.269 g, 0.695 mmol, 67.7% yield) as a solid.

$^1$H NMR (400 MHz, DMSO-d$_6$) δ ppm 1.42-1.63 (m, 1 H) 1.72-1.93 (m, 3 H) 2.82-3.11 (m, 3 H) 3.59 (s, 3 H) 4.19-4.36 (m, 2 H) 5.16 (s, 2 H) 7.63-7.83 (m, 4 H)

MS ES$^+$: 387

Example 101

1-[(1,3-Dimethyl-1H-pyrazol-4-yl)carbonyl]-3-(4-methoxy-2-methylphenyl)piperidine

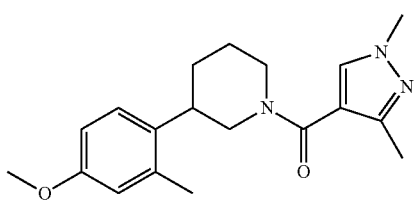 [SMILES: COc1ccc(C2CCCN(C(=O)c3cn(C)nc3C)C2)c(C)c1]

Propylphosphonic anhydride (50% solution in EtOAc) (0.448 mL, 0.511 mmol) was added to a solution of 1,3-dimethyl-1H-pyrazole-4-carboxylic acid (0.057 g, 0.409 mmol), 3-(4-methoxy-2-methylphenyl)piperidine (0.07 g, 0.341 mmol) (Intermediate 1a22), and triethylamine (0.143 mL, 1.023 mmol) in DCM (2 mL). The reaction mixture was stirred at room temperature for 1 hour. The mixture was diluted with DCM, washed with saturated NaHCO$_3$ (1×25 mL), and concentrated in vacuo. The crude product was purified by reverse phase preparative HPLC eluting with acetonitrile/water (with 0.1% ammonia) to afford 1-[(1,3-dimethyl-1H-pyrazol-4-yl)carbonyl]-3-(4-methoxy-2-methylphenyl)piperidine (0.029 g, 0.089 mmol, 26% yield) as a glass.

$^1$H NMR (400 MHz, DMSO-d$_6$) δ ppm 1.46-1.59 (m, 1 H) 1.68-1.89 (m, 3H) 2.12-2.27 (m, 6 H) 2.64-2.77 (m, 1 H) 2.78-3.04 (m, 2 H) 3.71 (s, 3 H) 3.75 (s, 3 H) 4.05-4.47 (m, 2 H) 6.68-6.78 (m, 2 H) 7.12-7.18 (m, 1 H) 7.80 (s, 1 H)

MS ES$^+$: 328

Example 102

4-{[3-(4-Methoxy-2-methylphenyl)piperidin-1-yl]carbonyl}-1-methyl-1H-pyrazol-3-amine

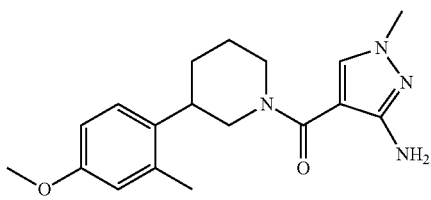 [SMILES: COc1ccc(C2CCCN(C(=O)c3cn(C)nc3N)C2)c(C)c1]

Prepared as described for 4-({3-[4-chloro-2-(trifluoromethyl)phenyl]piperidin-1-yl}carbonyl)-1-methyl-1H-pyrazol-3-amine (Example 100) from ethyl 3-{[(tert-butoxy)carbonyl]amino}-1-methyl-1H-pyrazole-4-carboxylate (Intermediate 2a2, step (ii)) and 3-(4-methoxy-2-methylphenyl)piperidine (Intermediate 1a22).

$^1$H NMR (400 MHz, DMSO-d$_6$) δ ppm 1.51-1.62 (m, 1 H) 1.67-1.89 (m, 3 H) 2.25 (s, 3 H) 2.65-2.84 (m, 2 H) 2.97 (br. s., 1 H) 3.60 (s, 3 H) 3.71 (s, 3 H) 4.16-4.34 (m, 2 H) 5.14 (s, 2 H) 6.70-6.78 (m, 2 H) 7.12-7.20 (m, 1 H) 7.71 (s, 1 H)

MS ES$^+$: 329

Example 103

3-[4-Chloro-2-(trifluoromethyl)phenyl]-1-[(1,3-dimethyl-1H-pyrazol-4-yl)carbonyl]piperidine

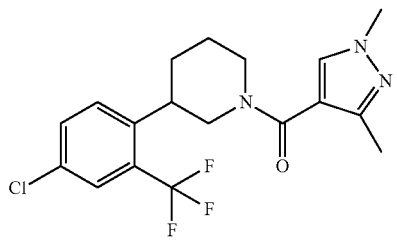 [SMILES: Cc1nn(C)cc1C(=O)N1CCCC(c2ccc(Cl)cc2C(F)(F)F)C1]

Propylphosphonic anhydride (50% in ethyl acetate) (0.499 mL, 0.569 mmol) was added to a solution of 1,3-dimethyl-1H-pyrazole-4-carboxylic acid (0.058 g, 0.417 mmol), 3-[4-chloro-2-(trifluoromethyl)phenyl]piperidine (0.1 g, 0.379 mmol) (Intermediate 1a6) and triethylamine (0.159 mL, 1.138 mmol) in dichloromethane (2 mL). The reaction mixture was stirred at room temperature overnight. The mixture was diluted with DCM, washed with saturated aqueous NaHCO$_3$ (1×25 mL) and concentrated in vacuo. The crude product was purified by reverse phase preparative HPLC eluting with acetonitrile/water (with 0.1% ammonia) and then freeze-dried to afford 3-[4-chloro-2-(trifluoromethyl)phenyl]-1-[(1,3-dimethyl-1H-pyrazol-4-yl)carbonyl]piperidine as a solid.

$^1$H NMR (400 MHz, DMSO-d$_6$) δ ppm 1.42-1.59 (m, 1 H) 1.72-1.91 (m, 3 H) 2.15 (s, 3 H) 2.89 (br. s., 1 H) 3.02 (br. s., 2 H) 3.74 (s, 3 H) 4.00-4.42 (m, 2 H) 7.69-7.80 (m, 4 H)

MS ES$^+$: 386

Example 104

4-{[5-(4-Chlorophenyl)-1,2,3,4-tetrahydropyridin-1-yl]carbonyl}-N,N-dimethylpyridin-2-amine

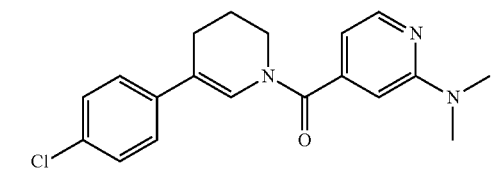 [SMILES: CN(C)c1cc(C(=O)N2C=C(c3ccc(Cl)cc3)CCC2)ccn1]

A microwave vial containing 1-{[2-(dimethylamino)pyridin-4-yl]carbonyl}-1,4,5,6-tetrahydropyridin-3-yl 1,1,2,2,3,3,4,4,4-nonafluorobutane-1-sulfonate (0.1 g, 0.189 mmol) (Intermediate 3a2), (4-chlorophenyl)boronic acid (0.032 g, 0.208 mmol), tetrakis(triphenylphosphine) palladium (0) (10.91 mg, 9.45 μmol) and cesium carbonate (0.129 g, 0.397 mmol) in dioxane (2 mL)/water (0.5 mL) was purged with nitrogen, sealed and irradiated at 100° C. for 10 mins in the microwave. The reaction was diluted in EtOAc (20 mL) and washed with water (5 mL) and brine (5 mL), dried over MgSO$_4$, filtered and reduced in vacuo. The crude product was purified by reverse phase preparative HPLC eluting with acetonitrile/water (with 0.1% ammonia) to afford 4-{[5-(4-chlorophenyl)-1,2,3,4-tetrahydropyridin-1-yl]carbonyl}-N,N-dimethylpyridin-2-amine (30 mg, 0.088 mmol, 46.5% yield) as a solid.

$^1$H NMR (400 MHz, DMSO-d$_6$) δ ppm 1.81-2.07 (m, 2 H) 2.48 (m, 2 H) 3.05 (s, 6 H) 3.51 (br. s., 1 H) 3.76 (br. s., 1 H) 6.52-6.73 (m, 2 H) 7.14-7.53 (m, 4 H) 7.60-7.79 (m, 1 H) 8.18 (d, J=4.80 Hz, 1 H)

MS ES$^+$: 342

Example 105

4-{[5-(4-Chloro-2-methylphenyl)-1,2,3,4-tetrahydropyridin-1-yl]carbonyl}-N,N-dimethylpyridin-2-amine

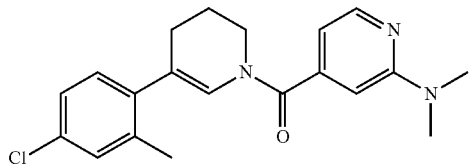 [SMILES: Cc1cc(Cl)ccc1C1=CN(C(=O)c2ccnc(N(C)C)c2)CCC1]

Prepared as described for 4-{[5-(4-chlorophenyl)-1,2,3,4-tetrahydropyridin-1-yl]carbonyl}-N,N-dimethylpyridin-2-amine (Example 104) from 1-{[2-(dimethylamino)pyridin-4-yl]carbonyl}-1,4,5,6-tetrahydropyridin-3-yl 1,1,2,2,3,3,4,4,4-nonafluorobutane-1-sulfonate (Intermediate 3a2) and (4-chloro-2-methylphenyl)boronic acid.

$^1$H NMR (400 MHz, DMSO-d$_6$) δ ppm 1.77-2.08 (m, 2 H) 2.18 (br. s, 2 H) 2.31 (br. s, 3 H) 2.93-3.10 (m, 6 H) 3.46-3.58 (m, 1 H) 3.78 (br. s., 1 H) 6.21 (s, 1 H) 6.48-6.71 (m, 2 H) 7.03-7.36 (m, 3 H) 8.07-8.23 (m, 1 H)

MS ES$^+$: 356

Example 106

4-{[5-(2,4-Dichlorophenyl)-1,2,3,4-tetrahydropyridin-1-yl]carbonyl}-N,N-dimethylpyridin-2-amine

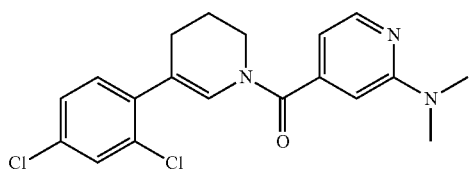 [SMILES: CN(C)c1cc(C(=O)N2C=C(c3ccc(Cl)cc3Cl)CCC2)ccn1]

Prepared as described for 4-{[5-(4-chlorophenyl)-1,2,3,4-tetrahydropyridin-1-yl]carbonyl}-N,N-dimethylpyridin-2-amine (Example 104) from 1-{[2-(dimethylamino)pyridin-4-yl]carbonyl}-1,4,5,6-tetrahydropyridin-3-yl 1,1,2,2,3,3,4,4,4-nonafluorobutane-1-sulfonate (Intermediate 3a2) and (2,4-dichlorophenyl)boronic acid.

$^1$H NMR (400 MHz, DMSO-d$_6$) δ ppm 2.00 (m, 2 H) 2.29-2.44 (m, 2 H) 2.92-3.10 (m, 6 H) 3.43-3.86 (m, 2 H) 6.38-6.74 (m, 3 H) 7.19-7.69 (m, 3 H) 8.06-8.25 (m, 1H)

MS ES$^+$: 376

Example 107

N,N-Dimethyl-4-[(3-phenylazepan-1-yl)carbonyl]pyridin-2-amine

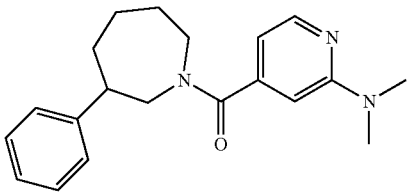 [SMILES: CN(C)c1cc(C(=O)N2CCCCC(c3ccccc3)C2)ccn1]

Prepared as described for 4-{[3-(2-fluorophenyl)piperidin-1-yl]carbonyl}-N,N-dimethylpyridin-2-amine (Example 1) from 2-(dimethylamino)isonicotinic acid hydrochloride and 3-phenylazepane.

$^1$H NMR (400 MHz, DMSO-d$_6$) δ ppm 1.24-2.14 (m, 6 H) 2.70-3.09 (m, 7 H) 3.14-3.27 (m, 1 H) 3.36-3.51 (m, 2 H) 3.82-4.13 (m, 1 H) 6.42-6.60 (m, 2 H) 6.94-7.41 (m, 5 H) 8.12 (m, 1 H)

MS ES$^+$: 324

Example 108

4-{[3-(4-Chlorophenyl)azepan-1-yl]carbonyl}-N,N-dimethylpyridin-2-amine

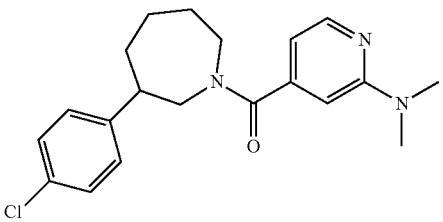 [SMILES: CN(C)c1cc(C(=O)N2CCCCC(c3ccc(Cl)cc3)C2)ccn1]

To a stirred solution of 2-(dimethylamino)isonicotinic acid hydrochloride (62.8 mg, 0.31 mmol) and 3-(4-chlorophenyl)azepane hydrochloride (76 mg, 0.310 mmol) in DCM (2 mL) was added triethylamine (0.130 mL, 0.930 mmol) and propylphosphonic anhydride (50% solution in EtOAc) (0.219 mL, 0.372 mmol).

The reaction was quenched by addition of saturated aqueous NaHCO$_3$ (2 mL). The mixture was diluted in EtOAc (15 mL) and washed with water (2×5 mL). The crude product was purified by reverse phase preparative HPLC eluting with acetonitrile/water (with 0.1% formic acid) and lyophilised to afford 4-{[3-(4-chlorophenyl)azepan-1-yl]carbonyl}-N,N-dimethylpyridin-2-amine (29.5 mg, 0.082 mmol, 27% yield).

$^1$H NMR (400 MHz, DMSO-d$_6$) δ ppm 1.30-2.10 (m, 6 H) 2.81-3.09 (m, 1 H) 3.14-3.55 (m, 9 H) 3.79-4.09 (m, 1 H) 6.77-7.00 (m, 1 H) 7.05-7.47 (m, 5 H) 7.90-8.12 (m, 1 H)

MS ES$^+$: 358

Example 109

4-{[3-(4-Methoxyphenyl)azepan-1-yl]carbonyl}-N,N-dimethylpyridin-2-amine

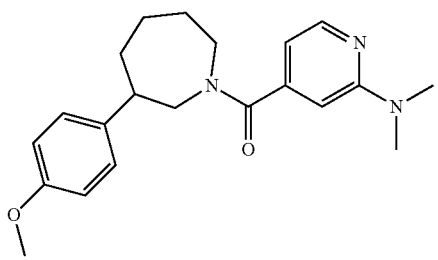 [SMILES: COc1ccc(C2CCCCN(C(=O)c3ccnc(N(C)C)c3)C2)cc1]

Prepared as described for 4-{[3-(4-chlorophenyl)azepan-1-yl]carbonyl}-N,N-dimethylpyridin-2-amine (Example 108) from 2-(dimethylamino)isonicotinic acid hydrochloride and 3-(4-methoxyphenyl)azepane hydrochloride.

$^1$H NMR (400 MHz, DMSO-$d_6$) δ ppm 1.32-2.06 (m, 6 H) 2.70-3.52 (m, 10 H) 3.58-3.78 (m, 3 H) 3.82-4.11 (m, 1 H) 6.58-6.71 (m, 1 H) 6.72-6.84 (m, 2 H) 6.86-7.00 (m, 2 H) 7.16-7.27 (m, 1 H) 7.98-8.12 (m, 1 H)

MS ES$^+$: 354

Example 110

4-{[3-(4-Methoxyphenyl)azepan-1-yl]carbonyl}-N-methylpyridin-2-amine

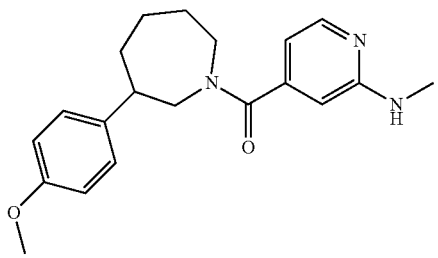 [SMILES: CNc1cc(C(=O)N2CCCCC(c3ccc(OC)cc3)C2)ccn1]

To a stirred solution of 2-(methylamino)isonicotinic acid hydrochloride (70 mg, 0.354 mmol) and triethylamine (0.148 mL, 1.063 mmol) in DCM (2 mL) was added propylphosphonic anhydride (50% solution in EtOAc) (0.522 mL, 0.886 mmol), then 3-(4-methoxyphenyl)azepane hydrochloride (86 mg, 0.354 mmol). The reaction was quenched with saturated aqueous NaHCO$_3$ (2 mL). The mixture was diluted with EtOAc (10 mL), washed with saturated aqueous NaHCO$_3$ (3×5 mL) and brine (5 mL). The crude product was purified by reverse phase preparative HPLC eluting with acetonitrile/water (with 0.1% ammonia) to afford 4-{[3-(4-methoxyphenyl)azepan-1-yl]carbonyl}-N-methylpyridin-2-amine (73.3 mg, 0.216 mmol, 61% yield) as a solid.

$^1$H NMR (400 MHz, DMSO-$d_6$) δ ppm 1.29-2.05 (m, 6 H) 2.67-2.97 (m, 4 H) 3.09-3.23 (m, 1 H) 3.35-3.45 (m, 2 H) 3.55-3.78 (m, 3 H) 3.80-4.09 (m, 1 H) 6.24-6.50 (m, 2 H) 6.55-6.68 (m, 1 H) 6.70-7.01 (m, 3 H) 7.12-7.26 (m, 1 H) 7.92-8.09 (m, 1 H)

MS ES$^+$: 340

Example 111

4-{[3-(4-Chlorophenyl)azepan-1-yl]carbonyl}-N-methylpyridin-2-amine

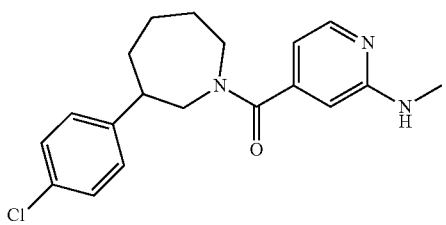 [SMILES: CNc1cc(C(=O)N2CCCCC(c3ccc(Cl)cc3)C2)ccn1]

Prepared as for 4-{[3-(4-methoxyphenyl)azepan-1-yl]carbonyl}-N-methylpyridin-2-amine (Example 110) from 2-(methylamino)isonicotinic acid hydrochloride and 3-(4-chlorophenyl)azepane hydrochloride.

$^1$H NMR (400 MHz, DMSO-$d_6$) δ ppm 1.31-2.06 (m, 6 H) 2.72-3.02 (m, 4 H) 3.16-3.29 (m, 1 H) 3.34-3.46 (m, 2 H) 3.78-4.09 (m, 1 H) 6.24-6.51 (m, 2 H) 6.55-6.72 (m, 1 H) 6.97-7.16 (m, 1 H) 7.20-7.45 (m, 3 H) 7.91-8.08 (m, 1 H)

MS ES$^+$: 344

Example 112

5-{[3-(4-Methoxyphenyl)azepan-1-yl]carbonyl}-N-methylpyridazin-3-amine

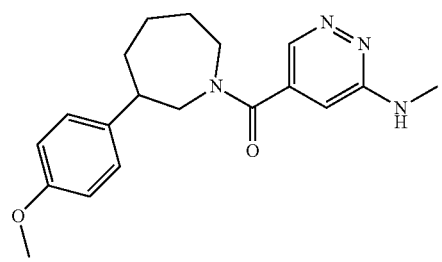 [SMILES: CNc1cc(C(=O)N2CCCCC(c3ccc(OC)cc3)C2)cnn1]

To a stirred solution of 1-[(6-chloropyridazin-4-yl)carbonyl]-3-(4-methoxyphenyl)azepane (108 mg, 0.311 mmol) (Intermediate 12) in butan-1-ol (4 mL) and NMP (2 mL) was added methylamine (2.0M in THF; 2.333 mL, 4.67 mmol). The vial was purged with nitrogen, sealed and irradiated in the microwave at 135° C. for 110 minutes. Additional methylamine (2.0M in THF; 0.77 mL, 1.56 mmol) was added and the reaction mixture was irradiated in the microwave at 135° C. for another 30 minutes, followed by irradiation in the microwave at 150° C. for 60 minutes. The reaction mixture was concentrated in vacuo and the crude product was purified by reverse phase preparative HPLC eluting with acetonitrile/water (with 0.1% ammonia) to afford 5-{[3-(4-methoxyphenyl)azepan-1-yl]carbonyl}-N-methylpyridazin-3-amine (72.9 mg, 0.214 mmol, 69% yield) as a solid.

$^1$H NMR (400 MHz, DMSO-$d_6$) δ ppm 1.34-2.05 (m, 6 H) 2.65-2.96 (m, 4 H) 3.13-3.51 (m, 3 H) 3.61-3.79 (m, 3 H) 3.82-4.09 (m, 1 H) 6.64-7.05 (m, 5 H) 7.14-7.29 (m, 1 H) 8.33-8.50 (m, 1 H)

MS ES$^+$: 341

Example 113

5-{[3-(4-Chlorophenyl)azepan-1-yl]carbonyl}-N-methylpyridazin-3-amine

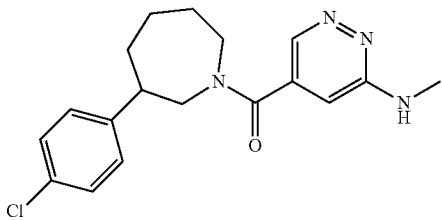 [SMILES: CNc1cc(C(=O)N2CCCCC(c3ccc(Cl)cc3)C2)cnn1]

To a stirred solution of 3-(4-chlorophenyl)-1-[(6-chloropyridazin-4-yl)carbonyl]azepane (109 mg, 0.311 mmol) (Intermediate 13) in butan-1-ol (4 mL) and NMP (2 mL) was added methylamine (2.0M in THF; 2.333 mL, 4.67 mmol). The vial was purged with nitrogen, sealed and irradiated in the microwave at 135° C. for 110 minutes. Additional methylamine (2.0M in THF; 0.77 mL, 1.56 mmol) was added and the reaction mixture was irradiated in the microwave at 135° C. for a further 30 minutes, followed by irradiation in the microwave at 150° C. for 60 minutes. The reaction was concentrated in vacuo and the crude product was purified by reverse phase preparative HPLC eluting with acetonitrile/water (with 0.1% ammonia) to afford 5-{[3-(4-chlorophenyl)azepan-1-yl]carbonyl}-N-methylpyridazin-3-amine (63.7 mg, 0.185 mmol, 59% yield) as a solid.

$^1$H NMR (400 MHz, DMSO-$d_6$) δ ppm 1.21-2.12 (m, 6 H) 2.75-3.03 (m, 4 H) 3.15-3.52 (m, 3 H) 3.77-4.09 (m, 1 H) 6.64-6.82 (m, 1 H) 6.87-7.04 (m, 1 H) 7.07-7.18 (m, 1 H) 7.23-7.45 (m, 3 H) 8.33-8.54 (m, 1 H)

MS ES$^+$: 345

Example 114

5-{[3-(4-Methoxyphenyl)azepan-1-yl]carbonyl}-N,N-dimethylpyridazin-3-amine

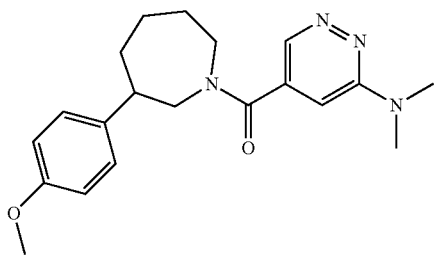 [SMILES: COc1ccc(C2CCCCN(C(=O)c3cnnc(N(C)C)c3)C2)cc1]

Prepared as described for 5-{[3-(4-chlorophenyl)azepan-1-yl]carbonyl}-N-methylpyridazin-3-amine (Example 113) from 1-[(6-chloropyridazin-4-yl)carbonyl]-3-(4-methoxyphenyl)azepane (Intermediate 12) and dimethylamine (2M in THF).

$^1$H NMR (400 MHz, DMSO-$d_6$) δ ppm 1.21-2.05 (m, 6 H) 3.03-3.16 (m, 6 H) 3.17-3.51 (m, 4 H) 3.62-3.77 (m, 3 H) 3.81-4.13 (m, 1 H) 6.69-6.83 (m, 1 H) 6.86-6.99 (m, 2 H) 7.00-7.10 (m, 1 H) 7.16-7.31 (m, 1 H) 8.42-8.58 (m, 1 H)

MS ES$^+$: 355

Example 115

5-{[3-(4-Chlorophenyl)azepan-1-yl]carbonyl}-N,N-dimethylpyridazin-3-amine

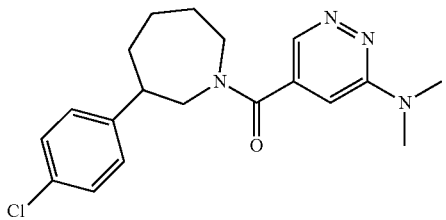 [SMILES: CN(C)c1cc(C(=O)N2CCCCC(c3ccc(Cl)cc3)C2)cnn1]

Prepared as described for 5-{[3-(4-chlorophenyl)azepan-1-yl]carbonyl}-N-methylpyridazin-3-amine (Example 113) from 3-(4-chlorophenyl)-1-[(6-chloropyridazin-4-yl)carbonyl]azepane (Intermediate 13) and dimethylamine (2M in THF).

$^1$H NMR (400 MHz, DMSO-$d_6$) δ ppm 1.34-2.10 (m, 6 H) 2.80-3.55 (m, 10 H) 3.79-4.14 (m, 1 H) 6.90-7.15 (m, 2 H) 7.21-7.45 (m, 3 H) 8.40-8.58 (m, 1 H) MS ES$^+$: 359

Example 116

3-(4-Chloro-2-methylphenyl)-1-{[2-(dimethylamino)pyridin-4-yl]carbonyl}piperidin-3-ol

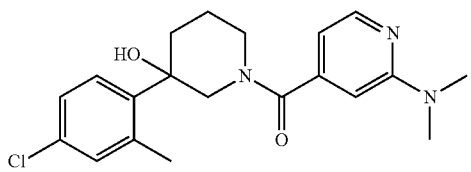 [SMILES: Cc1cc(Cl)ccc1C1(O)CCCN(C(=O)c2ccnc(N(C)C)c2)C1]

To a stirred solution of 1-{[2-(dimethylamino)pyridin-4-yl]carbonyl}piperidin-3-one (250 mg, 1.011 mmol) (Intermediate 3a1) in anhydrous THF (1 mL), cooled in an ice bath, was added a solution of (4-chloro-2-methylphenyl)magnesium bromide (0.5M in THF) (3.03 mL, 1.516 mmol) drop wise over 5 minutes under a nitrogen gas atmosphere. The ice bath was removed and the reaction mixture was stirred at ambient temperature for 6 hours. The reaction mixture was quenched with a saturated ammonium chloride solution (10 mL), ethyl acetate was added (10 mL) and the mixture was stirred vigorously for 18 hours before being diluted with water (10 mL). The phases were separated, the aqueous phase was extracted with ethyl acetate (2×10 mL) and the combined organic phases were concentrated in vacuo. The crude product was purified by reverse phase preparative HPLC eluting with acetonitrile/water (with 0.1% ammonia) to afford the title compound 3-(4-chloro-2-methylphenyl)-1-{[2-(dimethylamino)pyridin-4-yl]carbonyl}piperidin-3-ol (10.8 mg, 0.028 mmol, 2.77% yield) as a colourless gum.

$^1$H NMR (400 MHz, CHCl$_3$-d) δ ppm 1.41-2.36 (m, 7 H) 2.54-2.90 (m, 2 H) 2.98-3.17 (m, 6 H) 3.18-3.42 (m, 1 H) 3.68-4.00 (m, 1 H) 4.63-4.90 (m, 1 H) 6.47-6.61 (m, 2 H) 7.04-7.38 (m, 3 H) 8.07-8.34 (m, 1 H)

MS ES$^+$: 374

Example 117

1-{[2-(Dimethylamino)pyridin-4-yl]carbonyl}-3-(4-fluorophenyl)piperidin-3-ol

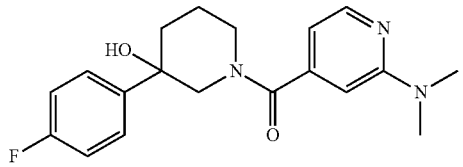 [SMILES: CN(C)c1cc(C(=O)N2CCCC(O)(c3ccc(F)cc3)C2)ccn1]

Prepared as described for 3-(4-chloro-2-methylphenyl)-1-{[2-(dimethylamino)pyridin-4-yl]carbonyl}piperidin-3-ol (Example 116) from 1-{[2-(dimethylamino)pyridin-4-yl]carbonyl}piperidin-3-one (Intermediate 3a1) and (4-fluorophenyl)magnesium bromide.

$^1$H NMR (400 MHz, CHCl$_3$-d) δ ppm 1.16-2.85 (m, 6 H) 2.97-3.13 (m, 6 H) 3.15-3.25 (m, 1 H) 3.61-3.82 (m, 1 H) 4.55-4.83 (m, 1 H) 6.47-6.73 (m, 2 H) 6.93-7.11 (m, 2 H) 7.32-7.53 (m, 2 H) 8.08-8.26 (m, 1 H)

MS ES$^+$: 344

Example 118

4-({3-[4-Chloro-2-(trifluoromethyl)phenyl]piperidin-1-yl}carbonyl)-1-methyl-1H-pyrazol-3-amine (Enantiomer 1)

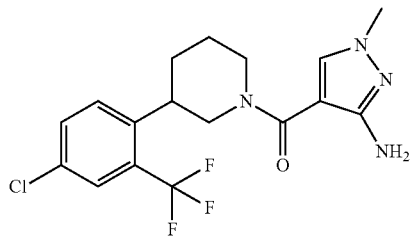 [SMILES: Cn1cc(C(=O)N2CCCC(c3ccc(Cl)cc3C(F)(F)F)C2)c(N)n1]

A solution of propylphosphonic anhydride (50 wt % in EtOAc, 0.219 ml, 0.250 mmol) was added to a solution of 3-((tert-butoxycarbonyl)amino)-1-methyl-1H-pyrazole-4-carboxylic acid (Intermediate 2a2 step ii)) (0.044 g, 0.183 mmol), 3-[4-chloro-2-(trifluoromethyl)phenyl]piperidine hydrochloride (Intermediate 1a6A, 0.05 g, 0.167 mmol) and triethylamine (0.070 ml, 0.500 mmol) in DCM (2 ml). The reaction was stirred at room temperature for 1 hour. The mixture was diluted with DCM, washed with saturated NaHCO$_3$ (1×15 ml), dried (phase separator) and concentrated. The residue was taken up in methanol (2 ml). HCl (4M in dioxane) (0.208 ml, 0.833 mmol) was added and the reaction was stirred for 3 hours. Additional HCl (4M in dioxane) (0.208 ml, 0.833 mmol) was added and the reaction was stirred overnight. The solution was concentrated in vacuo. The crude product was purified by reverse phase preparative HPLC eluted with acetonitrile/water (with 0.1% ammonia) to afford (4-({3-[4-chloro-2-(trifluoromethyl)phenyl]piperidin-1-yl}carbonyl)-1-methyl-1H-pyrazol-3-amine (Enantiomer 1; 0.033 g, 0.085 mmol, 51% yield) as a foam.

$^1$H NMR (300 MHz, DMSO-d$_6$) δ ppm 1.42-1.64 (m, 1 H) 1.71-1.92 (m, 3 H) 2.66-3.16 (m, 3 H) 3.59 (s, 3 H) 4.17-4.36 (m, 2 H) 5.16 (s, 2 H) 7.70 (s, 1 H) 7.73-7.81 (m, 3 H)

MS ES$^+$: 387

Example 119

4-({3-[4-Chloro-2-(trifluoromethyl)phenyl]piperidin-1-yl}carbonyl)-1-methyl-1H-pyrazol-3-amine (Enantiomer 2)

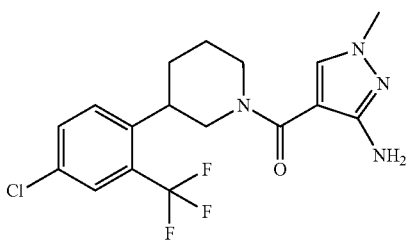 [SMILES: Cn1cc(C(=O)N2CCCC(c3ccc(Cl)cc3C(F)(F)F)C2)c(N)n1]

Prepared as described for Example 118 using 3-[(4-chloro-2-(trifluoromethyl)phenyl]piperidine hydrochloride (Intermediate 1a6B, 0.05 g, 0.167 mmol) to afford (4-({3-[4-chloro-2-(trifluoromethyl)phenyl]piperidin-1-yl}carbonyl)-1-methyl-1H-pyrazol-3-amine (Enantiomer 2; 0.036 g, 0.093 mmol, 56% yield) as a solid.

$^1$H NMR (400 MHz, DMSO-d$_6$) δ ppm 1.45-1.61 (m, 1 H) 1.75-1.91 (m, 3 H) 2.83-3.13 (m, 3 H) 3.59 (s, 3 H) 4.22-4.34 (m, 2 H) 5.16 (s, 2 H) 7.70 (s, 1 H) 7.74-7.81 (m, 3 H)

MS ES$^+$: 387

3. Biological Assay

Prokineticin receptor 1 (PKR1) antagonists may be functionally assessed by measurement of change in intracellular calcium levels induced by Gq mediated increase in inositol triphosphate (IP3) levels. The ability of a compound to block the intracellular release of calcium mediated by PK1 in RBL2H3 cells expressing human PKR1 receptors is determined as a measure of the compound's antagonist activity in vitro.

Approximately 10,000 cells per assay well are seeded in normal culture medium in a 384 well plate (Corning). Twenty-four hours after seeding, the cells are loaded with a calcium sensitive fluorescent dye by replacing the culture medium with assay buffer (1× Hanks buffered saline, 25 mM HEPES, 0.1% w/v fatty acid free BSA (bovine serum albumin), pH 7.4) containing 1 mM probenecid and 1× Calcium 5 Reagent (Molecular Devices). Cells are incubated at 37° C. for 1 hour to allow for dye uptake.

To test for antagonist activity, test compounds at a final concentration range between 0.32 nM-10 μM (diluted in assay buffer) are added to the assay wells and allowed to incubate for 10 minutes prior to stimulation with PK1. After incubation with test compounds the assay plate is placed in a FLIPR Tetra (Molecular Devices) and PK1 (diluted in assay buffer) is added at the determined EC80 concentration (final). Ligand-dependent changes in intracellular calcium levels are determined by measuring changes in fluorescence of the dye at 525 nM following excitation at 485 nM. Readings from wells that do not contain antagonist enable percentage inhibition curves to be plotted using 4-parameter fit algorithm and IC$_{50}$ values are calculated for each test compound.

Results

| Compound of Example No. | Mean IC$_{50}$ (μM) | Compound of Example No. | Mean IC$_{50}$ (μM) |
|---|---|---|---|
| 1 | 1.82 | 2 | 0.19 |
| 3 | 1.74 | 4 | 0.07 |
| 5 | 0.45 | 6 | 0.28 |
| 7 | 0.1 | 8 | 3.27 |
| 9 | 1.37 | 10 | 1.17 |
| 11 | 0.29 | 12 | 2.8 |
| 13 | 1.92 | 14 | 0.19 |
| 15 | 1.14 | 16 | 0.27 |
| 17 | 0.84 | 18 | 0.18 |
| 19 | 1.22 | 20 | 1.21 |
| 21 | 1.2 | 22 | 1.04 |
| 23 | 0.96 | 24 | 0.03 |
| 25 | 0.53 | 26 | 0.47 |
| 27 | 0.13 | 28 | 1.33 |
| 29 | 3.29 | 30 | 0.83 |
| 31 | 0.03 | 32 | 0.49 |
| 33 | 0.09 | 34 | 5.27 |
| 35 | 8.82 | 36 | 5.51 |
| 37 | 5.53 | 38 | 6.5 |
| 39 | 8.22 | 40 | 7.03 |
| 41 | 8.46 | 42 | 8.35 |
| 43 | 7.05 | 44 | 4.4 |
| 45 | 0.22 | 46 | 7.79 |
| 47 | 0.46 | 48 | 0.41 |
| 49 | 0.42 | 50 | 0.99 |
| 51 | 0.31 | 52 | 0.51 |
| 53 | 2.92 | 54 | 0.23 |
| 55 | 0.35 | 56 | 0.44 |
| 57 | 0.05 | 58 | 0.82 |
| 59 | 1.6 | 60 | 1.6 |
| 61 | 0.1 | 62 | 0.1 |
| 63 | 0.04 | 64 | 0.05 |
| 65 | 0.07 | 66 | 0.7 |
| 67 | 2.26 | 68 | 1.54 |
| 69 | 0.81 | 70 | 0.12 |
| 71 | 0.07 | 72 | 0.03 |
| 73 | 1.18 | 74 | 0.35 |
| 75 | 0.11 | 76 | 0.08 |
| 77 | 0.73 | 78 | 3 |
| 79 | 0.13 | 80 | 0.16 |
| 81 | 0.13 | 82 | 0.21 |
| 83 | 0.17 | 84 | 0.09 |
| 85 | 1.14 | 86 | 1.26 |
| 87 | 0.2 | 88 | 1.82 |
| 89 | 1.28 | 90 | 0.66 |
| 91 | 0.96 | 92 | 0.11 |
| 93 | 0.18 | 94 | 0.17 |
| 95 | 0.15 | 96 | 2.44 |
| 97 | 0.10 | 98 | 0.17 |
| 99 | 0.33 | 100 | 0.54 |
| 101 | 1.03 | 102 | 1.54 |
| 103 | 0.49 | 104 | 0.42 |
| 105 | 0.27 | 106 | 1.23 |
| 107 | 2.97 | 108 | 3.23 |
| 109 | 0.96 | 110 | 0.45 |
| 111 | 0.43 | 112 | 1.27 |
| 113 | 0.93 | 114 | 1.43 |
| 115 | 1.44 | 116 | 1.36 |
| 117 | 3.94 | 118 | >10 |
| 119 | 0.33 | | |

The compounds tested above exhibit IC$_{50}$ values significantly less than 10 μM, with the most potent compounds showing antagonist activity at the prokineticin receptor with IC$_{50}$ values <1 μM. Accordingly, the compounds of the invention are expected to be useful in the prevention or treatment of conditions in which prokineticin receptor modulation is implicated.

The invention claimed is:

1. A pharmaceutical composition comprising a compound selected from the group consisting of:
racemic 5-{[3-(4-Chloro-2-methylphenyl)piperidin-1-yl]carbonyl}-N-methylpyridazin-3-amine;
a mixture of R and S enantiomers of 5-{[3-(4-Chloro-2-methylphenyl)piperidin-1-yl]carbonyl}-N-methyl-pyridazin-3-amine;
5-{[(3R)-3-(4-Chloro-2-methylphenyl)piperidin-1-yl]carbonyl}-N-methylpyridazin-3-amine;
racemic 4-({3-[4-Chloro-2-(trifluoromethyl)phenyl]piperidin-1-yl}carbonyl)-1-methyl-1H-pyrazol-3-amine;
a mixture of R and S enantiomers of 4-({3-[4-Chloro-2-(trifluoromethyl)phenyl]piperidin-1-yl} carbonyl)-1-methyl-1H-pyrazol-3-amine;
4-({(3R)-3-[4-Chloro-2-(trifluoromethyl)phenyl]piperidin-1-yl}carbonyl)-1-methyl-1H-pyrazol-3-amine;
4-({(3S)-3-[4-Chloro-2-(trifluoromethyl)phenyl]piperidin-1-yl}carbonyl)-1-methyl-1H-pyrazol-3-amine; and
pharmaceutically acceptable salts thereof,
in association with a pharmaceutically acceptable adjuvant, diluent or carrier, and optionally one or more other therapeutic agents.

2. The pharmaceutical composition according to claim 1, wherein the compound is racemic 5-{[3-(4-Chloro-2-methylphenyl)piperidin-1-yl]carbonyl}-N-methylpyridazin-3-amine or pharmaceutically acceptable salts thereof.

3. The pharmaceutical composition according to claim 1, wherein the compound is a mixture of R and S enantiomers of 5-{[3-(4-Chloro-2-methylphenyl)piperidin-1-yl]carbonyl}-N-methylpyridazin-3-amine or pharmaceutically acceptable salts thereof.

4. The pharmaceutical composition according to claim 1, wherein the compound is 5-{[(3R)-3-(4-Chloro-2-methylphenyl)piperidin-1-yl]carbonyl}-N-methylpyridazin-3-amine or a pharmaceutically acceptable salt thereof.

5. The pharmaceutical composition according to claim 1, wherein the compound is racemic 4-({3-[4-Chloro-2-(trifluoromethyl)phenyl]piperidin-1-yl}carbonyl)-1-methyl-1H-pyrazol-3-amine or pharmaceutically acceptable salts thereof.

6. The pharmaceutical composition according to claim 1, wherein the compound is a mixture of R and S enantiomers of 4-({3-[4-Chloro-2-(trifluoromethyl)phenyl]piperidin-1-yl}carbonyl)-1-methyl-1H-pyrazol-3-amine or pharmaceutically acceptable salts thereof.

7. The pharmaceutical composition according to claim 1, wherein the compound is 4-({(3R)-3-[4-Chloro-2-(trifluoromethyl)phenyl]piperidin-1-yl}carbonyl)-1-methyl-1H-pyrazol-3-amine or a pharmaceutically acceptable salt thereof.

8. The pharmaceutical composition according to claim 1, wherein the compound is 4-({(3S)-3-[4-Chloro-2-(trifluoromethyl)phenyl]piperidin-1-yl}carbonyl)-1-methyl-1H-pyrazol-3-amine or a pharmaceutically acceptable salt thereof.

9. A method for treatment of schizophrenia, comprising administering to a patient in need thereof, a pharmaceutical composition according to claim 1.

10. A method for treatment of schizophrenia, comprising administering to a patient in need thereof, a pharmaceutical composition according to claim 2.

11. A method for treatment of schizophrenia, comprising administering to a patient in need thereof, a pharmaceutical composition according to claim 3.

12. A method for treatment of schizophrenia, comprising administering to a patient in need thereof, a pharmaceutical composition according to claim 4.

13. A method for treatment of schizophrenia, comprising administering to a patient in need thereof, a pharmaceutical composition according to claim 5.

14. A method for treatment of schizophrenia, comprising administering to a patient in need thereof, a pharmaceutical composition according to claim 6.

15. A method for treatment of schizophrenia, comprising administering to a patient in need thereof, a pharmaceutical composition according to claim 7.

16. A method for treatment of schizophrenia, comprising administering to a patient in need thereof, a pharmaceutical composition according to claim 8.

17. A method for treatment of dementia or impaired learning, comprising administering to a patient in need thereof, a pharmaceutical composition according to claim 1.

18. A method for treatment of dementia or impaired learning, comprising administering to a patient in need thereof, a pharmaceutical composition according to claim 2.

19. A method for treatment of dementia or impaired learning, comprising administering to a patient in need thereof, a pharmaceutical composition according to claim 3.

20. A method for treatment of dementia or impaired learning, comprising administering to a patient in need thereof, a pharmaceutical composition according to claim 4.

21. A method for treatment of dementia or impaired learning, comprising administering to a patient in need thereof, a pharmaceutical composition according to claim 5.

22. A method for treatment of dementia or impaired learning, comprising administering to a patient in need thereof, a pharmaceutical composition according to claim 6.

23. A method for treatment of dementia or impaired learning, comprising administering to a patient in need thereof, a pharmaceutical composition according to claim 7.

24. A method for treatment of dementia or impaired learning, comprising administering to a patient in need thereof, a pharmaceutical composition according to claim 8.

25. A method for treatment of pain, comprising administering to a patient in need thereof, a pharmaceutical composition according to claim 1.

26. A method for treatment of pain, comprising administering to a patient in need thereof, a pharmaceutical composition according to claim 2.

27. A method for treatment of pain, comprising administering to a patient in need thereof, a pharmaceutical composition according to claim 3.

28. A method for treatment of pain, comprising administering to a patient in need thereof, a pharmaceutical composition according to claim 4.

29. A method for treatment of pain, comprising administering to a patient in need thereof, a pharmaceutical composition according to claim 5.

30. A method for treatment of pain, comprising administering to a patient in need thereof, a pharmaceutical composition according to claim 6.

31. A method for treatment of pain, comprising administering to a patient in need thereof, a pharmaceutical composition according to claim 7.

32. A method for treatment of pain, comprising administering to a patient in need thereof, a pharmaceutical composition according to claim 8.

* * * * *